(12) United States Patent
Guilford et al.

(10) Patent No.: US 11,130,789 B2
(45) Date of Patent: *Sep. 28, 2021

(54) URINE MARKERS FOR DETECTION OF BLADDER CANCER

(75) Inventors: Parry John Guilford, Dunedin (NZ); Natalie Jane Kerr, Dunedin (NZ); Robert Craig Pollock, Dunedin (NZ)

(73) Assignee: Pacific Edge Limited, Dunedin (NZ)

( * ) Notice: Subject to any disclaimer, the term of this patent is extended or adjusted under 35 U.S.C. 154(b) by 1958 days.

This patent is subject to a terminal disclaimer.

(21) Appl. No.: 11/658,220

(22) PCT Filed: Jul. 22, 2005

(86) PCT No.: PCT/US2005/026055
§ 371 (c)(1),
(2), (4) Date: Mar. 30, 2009

(87) PCT Pub. No.: WO2006/012522
PCT Pub. Date: Feb. 2, 2006

(65) Prior Publication Data
US 2010/0273148 A1  Oct. 28, 2010

Related U.S. Application Data

(60) Provisional application No. 60/692,619, filed on Jun. 20, 2005.

(30) Foreign Application Priority Data

Jul. 23, 2004 (NZ) ........................................ 534289
Apr. 4, 2005 (NZ) ........................................ 539219

(51) Int. Cl.
| | |
|---|---|
| *C07K 14/47* | (2006.01) |
| *G01N 33/574* | (2006.01) |
| *C12Q 1/6886* | (2018.01) |

(52) U.S. Cl.
CPC .......... *C07K 14/47* (2013.01); *C07K 14/4748* (2013.01); *C12Q 1/6886* (2013.01); *G01N 33/57407* (2013.01); *G01N 33/57488* (2013.01); *C12Q 2600/112* (2013.01); *C12Q 2600/158* (2013.01); *G01N 2800/52* (2013.01)

(58) Field of Classification Search
CPC .......... C12Q 1/00; C12Q 1/68; C12Q 1/6844; C12Q 1/6846; C12Q 1/686; C12Q 1/6886; C12Q 2600/112; C12Q 2600/158; G01N 1/00; G01N 33/48; G01N 33/483; G01N 33/487; G01N 33/493; G01N 33/57407; G01N 33/57488; G01N 2800/52; G01N 2333/47; G01N 33/6854; C07K 1/00; C07K 14/00; C07K 14/435; C07K 14/47; C07K 14/4748; C07K 16/00
See application file for complete search history.

(56) References Cited

U.S. PATENT DOCUMENTS

| | | | |
|---|---|---|---|
| 6,251,638 B1 | 6/2001 | Umansky et al. | |
| 6,287,820 B1 | 9/2001 | Umansky et al. | |
| 6,335,170 B1 | 1/2002 | Orntoft | |
| 6,433,155 B1 | 8/2002 | Umansky et al. | |
| 6,492,144 B1 | 12/2002 | Umansky et al. | |
| 6,495,532 B1 | 12/2002 | Bathurst et al. | |
| 2003/0023061 A1 | 1/2003 | Umansky | |
| 2003/0054387 A1 | 3/2003 | Chen | |
| 2003/0224374 A1 | 12/2003 | Dai | |
| 2004/0038207 A1* | 2/2004 | Orntoft ............... | C12Q 1/6809 435/6.14 |
| 2004/0039184 A1 | 2/2004 | Umansky et al. | |
| 2004/0043436 A1* | 3/2004 | Vlahou ............ | G01N 33/57407 435/7.23 |
| 2005/0014165 A1 | 1/2005 | Lee et al. | |
| 2005/0032065 A1 | 2/2005 | Afar | |

(Continued)

FOREIGN PATENT DOCUMENTS

| | | | |
|---|---|---|---|
| EP | 0 556 344 | | 8/2003 |
| WO | WO 92/12243 | * | 7/1992 |

(Continued)

OTHER PUBLICATIONS

EP Search Rpt 11188990.3, dated Sep. 6, 2014, Pacific Edge Limited.
EP Search Report, dated Jul. 24, 2009, EP 07715981.2.
Ying-Hao, Sun, et al., Monitoring gene expression profile changes in bladder transitional cell carcinoma using cDNA microarray; Urologic Oncology (2002) Elsevier Science Inc., pp. 207-212.
Thykjaer, Thomas, et al., Identification of gene expression patterns in superficial and invasive human bladder cancer; Cancer Research 61, 2492-2499, Mar. 15, 2001.
Kawakami, Kazumori, et al., Identification of differentially expressed genes in human bladder cancer through genome-wide gene expression profiling; Oncology Reports 16: 521-531, 2006.
Osman, Iman, et al., Novel blood biomarkers of human urinary bladder cancer; Imaging, Diagnosis, Prognosis, Clin Cancer Res 2006:12(11) Jun. 1, 2006 pp. 3374-3380.

(Continued)

*Primary Examiner* — Alana Harris Dent
(74) *Attorney, Agent, or Firm* — D. Benjamin Borson; Borson Law Group PC

(57) ABSTRACT

Early detection of tumors is a major determinant of survival of patients suffering from tumors, including bladder tumors. Members of the BTM or UBTM family can be highly and consistently accumulated in bladder tumor tissue and other tumor tissue, and/or can be accumulated in urine of patients, and thus are markers for bladder and other types of cancer. In certain embodiments, BTMs or UBTMs can accumulate in the urine, and detection of UBTM family members can be an effective diagnostic approach. In some embodiments, quantitative PCR methods have advantages over microarray methods. In other embodiments, detection and quantification of a plurality of BTMs or UBTMs can increase the sensitivity and specificity of detection of bladder cancer, and therefore provides methods for determining the stage and type of bladder cancer. Kits provide easy, convenient ways for carrying out the methods of this invention.

5 Claims, 73 Drawing Sheets

Specification includes a Sequence Listing.

(56) References Cited

U.S. PATENT DOCUMENTS

| | | | | |
|---|---|---|---|---|
| 2006/0019256 | A1* | 1/2006 | Clarke | C12N 5/0695 435/6.14 |
| 2009/0098553 | A1 | 4/2009 | Guilford | |
| 2009/0175844 | A1* | 7/2009 | Nakamura | C12Q 1/6886 424/130.1 |

FOREIGN PATENT DOCUMENTS

| WO | WO 01/22864 | 4/2001 |
|---|---|---|
| WO | WO 02/27329 | 4/2002 |
| WO | WO 02/86084 | 10/2002 |
| WO | WO 03/03906 | 1/2003 |
| WO | WO 04/33541 | 4/2004 |
| WO | WO 04/48938 | 6/2004 |
| WO | WO 04/70062 | 8/2004 |
| WO | WO 05/05601 | 1/2005 |
| WO | WO 05/08213 | 1/2005 |
| WO | WO 2005000087 A2 * | 1/2005 |
| WO | WO 2006/012522 | 2/2006 |

OTHER PUBLICATIONS

Lars Dyrskjet, Identifying distinct classes of bladder carcinoma using microarrays, Nature Genetics, vol. 33, Jan. 2003, Nature Publishing Group, pp. 90-96.

Non-Final Office Action dated Aug. 28, 2009, U.S. Appl. No. 12/221,626, filed Aug. 5, 2008.

Reply to Office Action dated Oct. 28, 2009, U.S. Appl. No. 12/221,626, filed Aug. 5, 2008.

Supplemental Reply to Office Action dated Oct. 28, 2009, U.S. Appl. No. 12/221,626, filed Aug. 5, 2008.

* cited by examiner

| Sample | Series 1 | Series 2 |
|---|---|---|
| TCC patients | | |
| superficial | 7 | 13 |
| invasive | 10 | 4 |
| carcinoma in situ | 2 | 1 |
| unknown stage | 2 | 2 |
| Non-malignant controls | | |
| Neurogenic bladder | | 6 |
| Prostate hyperplasia | | 9 |
| Urolithiasis | | 9 |
| Infection | | 2 |
| | | |
| Healthy controls | 10 | 13 |

Figure 1

| Name | Aliases | Symbol | Forward Primer | Seq ID # | Reverse Primer | Seq ID # | Probe | Seq ID # |
|---|---|---|---|---|---|---|---|---|
| sperm associated antigen 5 | MAP126; DEEPEST; hMAP126 | SPAG5 | AATTCAGAGGCTTCTGAAGGA | 1 | TCTGCTGAACCAGCTCTTCTTG | 14 | ACCCAACTGGTAGGGCTTCATGCCA | 27 |
| topoisomerase (DNA) II alpha 170kDa | TOP2; TP2A | TOP2A | CCGGCCCAGACACACCTACATTG | 2 | CCCTATAGTTAATGCCAACATCTTC | 15 | TTCTGTGGAATTAGTGACCCAGCAAATGTG | 28 |
| cell division cycle 2, G1 to S and G2 to M | | CDC2 | GCCGCCGGCGGAATAAT | 3 | ACCTTCTCCAATTTTCTCTATTTTGC | 16 | AGCCGGGATTCACCATACCCATTGACTAACT | 29 |
| endoglin (Osler-Rendu-Weber syndrome 1) | END; ORW; HHT1; ORW1; CD105 | ENG | GCAGGTGTCAGCAAGTATGATCA | 4 | ATGTTGAGGCAGTGCACCTTT | 17 | AATGAGGCGGTGGTCAATATCCTGTCG | 30 |
| insulin-like growth factor binding protein 5 | IBP5 | IGFBP5 | AATTGTGACCGGCAAAGGATTCT | 5 | CAGCAGATGCCACGCTTG | 18 | AAGAGAAAGCAGTGCAAACCTTCCCGT | 31 |
| nephroblastoma overexpressed gene | CCN3; NOVH; IGFBP9 | NOV | CGGACCCCAGCAACCA | 6 | CCCCATCGAACACACAGTTATCT | 19 | TGGCATCTGCACGGCGGTAGAG | 32 |
| neuropilin 1 | NRP; VEGF165R | NRP1 | GGAGTGTGTTGACCAGCAAGAC | 7 | CGTCAGCTTGGGAATAGATGAAG | 20 | CCCATTCAGGATCACACAGGAGATGGC | 33 |
| sema domain, immunoglobulin domain (Ig), short basic domain, secreted, (semaphorin) 3F | SEMA4; SEMAK; SEMA-IV; sema IV | SEMA3F | CCTGTCATTTACGTGTCTTTACC | 8 | GCGAATATCAGCCATGGAGTAGA | 21 | CTCTGGCTCCGTGTTCCGAGGC | 34 |
| EGF-like-domain, multiple 6 | W80; MAEG; DKFZP564P2063; DKFZp564P2063 | EGFL6 | TGCTCTCCTGGGTGGCAG | 9 | TAGTGACAGACCCCAGGCTGA | 22 | ACGCGGCCAGTGCAAGGCAT | 35 |
| matrix Gla protein | NTI; MGLAP | MGP | TTCATATCCCCTCAGCAGAGATG | 10 | TTGAGCTCGTGGACAGGCTTA | 23 | AGAGGTAAAGTCCAAGAGAGGATCCGAGAAC | 36 |
| semaphorin sem2 | LOC56920; FLJ00014 | SEM2 | CTCGAGGTGTACGCGCTGT | 11 | GCCCGTTGAAAACCTCCC | 24 | CACCGTCAGTGCCGTGTTCCAGG | 37 |
| chromogranin A (parathyroid secretory protein 1) | CGA | CHGA | TACAAGGAGATCCGAAAGGC | 12 | CAGGCTTCCCAGCTCCATC | 25 | AGAGTGGGTCGGAGGCTCTGGCTG | 38 |
| Thy-1 cell surface antigen | CD90 | THY1 | TGAACCTGGCCATCAGCAT | 13 | CGTTAGGCGTGGTCACCTTCTG | 26 | TGCTAACAGTCTTGCAGGTCTCCCGAG | 39 |
| ubiquitin-conjugating enzyme E2C | UBCH10; dJ447F3.2 | UBE2C | Taqman(R) Gene Expression Assay Hs00964100_g1 | | | | | |
| homeo box A13 | HOX1; HOX1J | HOXA13 | Taqman(R) Gene Expression Assay Hs00426284_m1 | | | | | |
| midkine (neurite growth-promoting factor 2) | NEGF2 | MDK | Taqman(R) Gene Expression Assay Hs00171084_m1 | | | | | |
| baculoviral IAP repeat-containing 5 (survivin) | API4; EPR-1 | BIRC5 | Taqman(R) Gene Expression Assay Hs00153353_m1 | | | | | |
| SMC4 structural maintenance of chromosomes 4-like 1 (yeast) | CAPC; hCAP-C | SMC4L1 | Taqman(R) Gene Expression Assay Hs00908709_g1 | | | | | |

| Gene Name | HUGO | MWG oligo # | NCBI mRNA ref seq | Protein ref seq | mean fold change | max fold change | T-test | Wilcoxen test | Summated rank | Serum | new? |
|---|---|---|---|---|---|---|---|---|---|---|---|
| MAX dimerization protein 4 | MXD4 | mwghuman30K6A3062_96 | NM_006454.2 | NP_006445.1 | 1.7 | 4.1 | 1.1E-05 | 0.0000134 | 1719.5 | | |
| phosphatidyl 4-phosphate adaptor protein-2 | FAPP2 | mwghuman30K6A3069_04 | NM_022932.2 | NP_116028.1 | 1.5 | 3.3 | 1.6E-05 | 3.67781E-05 | 1725.5 | | new |
| nucleoporin 210 | NUP210 | mwghuman30K6B-741 | NM_024923.2 | NP_079199.2 | 1.9 | 2.9 | 6.5E-05 | 0.000104262 | 1726.5 | | new |
| beta trypsin kinase | C6K | mwghuman30K6A3016_29 | NM_004363.1 | NP_004574.1 | 1.5 | 5.1 | 7.3E-06 | 8.56149E-07 | 3601 | | |
| neuropilin 1 | NRP1 | mwghuman30K6A3030_91 | NM_003873.2 | NP_003884.2 | 2.3 | 17.2 | 0.00276 | 0.004728544 | 6358 | | |

| Gene Name | HUGO | MWG oligo # | NCBI mRNA ref seq | Protein ref seq | mean fold change | max fold change | T-test | Wilcoxon test | Summated rank | Serum | new? |
|---|---|---|---|---|---|---|---|---|---|---|---|
| hypothetical protein DKFZp434G1415 | | mwghuman30k6C-3525 | NM_031292.2 | NP_112582.2 | 1.4 | 2.9 | 6.3E-05 | 0.000159 | 1501 | | new |
| WD repeat and SOCS box-containing 2A | WSB2 | mwghuman30k6B-1353 | NM_018639.3 | NP_061109.1 | 1.4 | 2.5 | 6.5E-05 | 0.000523 | 1506 | | |
| cytidine deaminase | CDA | mwghuman30k4A-07490 | NM_001785.1 | NP_001776.1 | 1.8 | 3.0 | 4.8E-05 | 0.000271 | 1539.5 | | |
| phosphoribosylglycinamide formyltransferase | GART | mwghuman30k4A-10142 | NM_000819.3 | NP_000810.1 | 1.4 | 2.2 | 4.3E-05 | 0.000146 | 1550 | | |
| histone 1, h1b | HIST1H1B | mwghuman30k4A-05718 | NM_005322.2 | NP_005313.1 | 1.8 | 3.9 | 9.3E-05 | 0.000236 | 1678.5 | | |
| zinc metallopeptidase (STE24 homolog, yeast) | ZMPSTE24 | mwghuman30k4A-09558 | NM_005857.2 | NP_005848.2 | 1.5 | 4.0 | 0.00017 | 0.000239 | 1653.5 | | new |
| transmembrane protein 33 | TMEM33 | mwghuman30k4A-01542 | NM_018126.1 | NP_060595.1 | 2.9 | 31.9 | 0.00037 | 0.002513 | 1669.5 | | |
| glucose phosphate isomerase | GPI | mwghuman30k6B-1465 | NM_000175.2 | NP_000166.2 | 1.4 | 2.8 | 0.00015 | 0.002238 | 1670.5 | | new |
| hypothetical protein FLJ11000 | | mwghuman30k6B-4538 | NM_018295.1 | NP_060785 | 1.6 | 5.1 | 0.0002 | 0.000448 | 1887.5 | | new |
| hypothetical protein MGC5576 | | mwghuman30k4A-09788 | NM_024052.2 | NP_076961.1 | 1.8 | 11.7 | 0.00074 | 0.000312 | 1710 | | new |
| calcium/calmodulin-dependent protein kinase ID | CAMK1D | mwghuman30k4A-00327 | NM_020397.1 | NP_065130.1 | 1.4 | 2.0 | 0.00034 | 0.000423 | 1719 | | new |
| protein tyrosine phosphatase, non-receptor type 21 | PTPN21 | mwghuman30k4A-09269 | NM_007039.2 | NP_008970.1 | 1.4 | 2.4 | 0.00057 | 0.000259 | 1723.5 | | |
| eukaryotic translation initiation factor 2C | EIF2C2 | mwghuman30k6C-2287 | NM_012154.2 | NP_036289.2 | 1.4 | 2.6 | 0.00011 | 0.000743 | 1730 | | |
| WD repeat domain 18 | WDR18 | mwghuman30k4B-3546 | NM_024100.2 | NP_077055.2 | 1.4 | 3.2 | 5.1E-05 | 0.000592 | 1748.5 | | |
| tensin | TNS | mwghuman30k6B-8493 | NM_022648.2 | NP_072174.2 | 1.3 | 2.0 | 3.8E-05 | 0.00017 | 1783.5 | | new |
| c-src tyrosine kinase | CSK | mwghuman30k4A-01629 | NM_004383.1 | NP_004374.1 | 1.4 | 1.9 | 1.1E-06 | 0.000107 | 1935.5 | | |
| ubiquitin-conjugating enzyme E2C | UBE2C | mwghuman30k4A-01776 | NM_181803.1 | NP_861519.1 | 2.1 | 8.9 | 0.00115 | 0.003908 | 2155 | | |
| neuropilin 1 | NRP1 | mwghuman30k4A-03991 | NM_003873.2 | NP_003864.2 | 1.9 | 6.0 | 0.00029 | 0.003639 | 2241 | | |

Figure 4 (cont.)

| Name | Aliases | Symbol | INVASIVE | | | SUPERFICIAL | | |
|---|---|---|---|---|---|---|---|---|
| | | | Median T:N fold change | Max T:N fold change | %T > 95th percentile of Normal | Median T:N fold change | Max T:N fold change | %T > 95th percentile of Normal |
| sperm associated antigen 5 | MAP126; DEEPEST; hMAP126 | SPAG5 | 40 | 516 | 93 | 8 | 60 | 83 |
| topoisomerase (DNA) II alpha 170kDa | TOP2; TP2A | TOP2A | 128 | 1136 | 93 | 39 | 417 | 88 |
| cell division cycle 2, G1 to S and G2 to M | CDC2 | CDK1 | 121 | 2526 | 93 | 27 | 152 | 88 |
| endoglin (Osler-Rendu-Weber syndrome 1) | END; ORW; HHT1; ORW1; CD105 | ENG | 4 | 32 | 57 | 8 | 35 | 84 |
| insulin-like growth factor binding protein 5 | IBP5 | IGFBP5 | | | | 7 | 164 | 60 |
| nephroblastoma overexpressed gene | CCN3; NOVH; IGFBP9 | NOV | | | | 4 | 16 | 65 |
| neuropilin 1 | NRP; VEGF165R | NRP1 | 7 | 195 | 89 | 10 | 37 | 80 |
| sema domain, immunoglobulin domain (Ig), short basic domain, secreted, (semaphorin) 3F | SEMA4; SEMAK; SEMA-IV; sema IV | SEMA3F | | | | 2 | 6 | 68 |
| EGF-like-domain, multiple 6 | W80; MAEG; DKFZP564P2063; DKFZp564P2063 | EGFL6 | 4 | 37 | 55 | 4 | 59 | 67 |
| matrix Gla protein | NTI; MGLAP | MGP | 3 | 1303 | 59 | | | |
| semaphorin sem2 | LOC56920; FLJ00014 | SEM2 | 6 | 54 | 72 | 9 | 38 | 75 |
| chromogranin A (parathyroid secretory protein 1) | CGA | CHGA | 0 | 4096 | 48 | 5 | >10,000 | 36 |
| ubiquitin-conjugating enzyme E2C | UBCH10; dJ447F3.2 | UBE2C | 44 | 219 | 47 | 11 | 619 | 14 |
| homeo box A13 | HOX1; HOX1J | HOXA13 | 4 | 58 | 46 | 11 | 117 | 67 |
| midkine (neurite growth-promoting factor 2) | NEGF2 | MDK | 2 | 56 | 59 | 2 | 8 | 68 |
| Thy-1 cell surface antigen | CD90 | THY1 | 48 | 481 | 89 | 21 | 79 | 86 |

Figure 5

| Name | Aliases | Symbol | INVASIVE | | | SUPERFICIAL | | |
|---|---|---|---|---|---|---|---|---|
| | | | Median T:N fold change | Max T:N fold change | %T > 95th percentile of Normal | Median T:N fold change | Max T:N fold change | %T > 95th percentile of Normal |
| baculoviral IAP repeat-containing 5 (survivin) | API4; EPR-1 | BIRC5 | 28 | 140 | 12 | 9 | 293 | 14 |
| SMC4 structural maintenance of chromosomes 4-like 1 (yeast) | CAPC; hCAP-C | SMC4L1 | 6 | 24 | 59 | 3 | 16 | 43 |

Figure 5 (cont.)

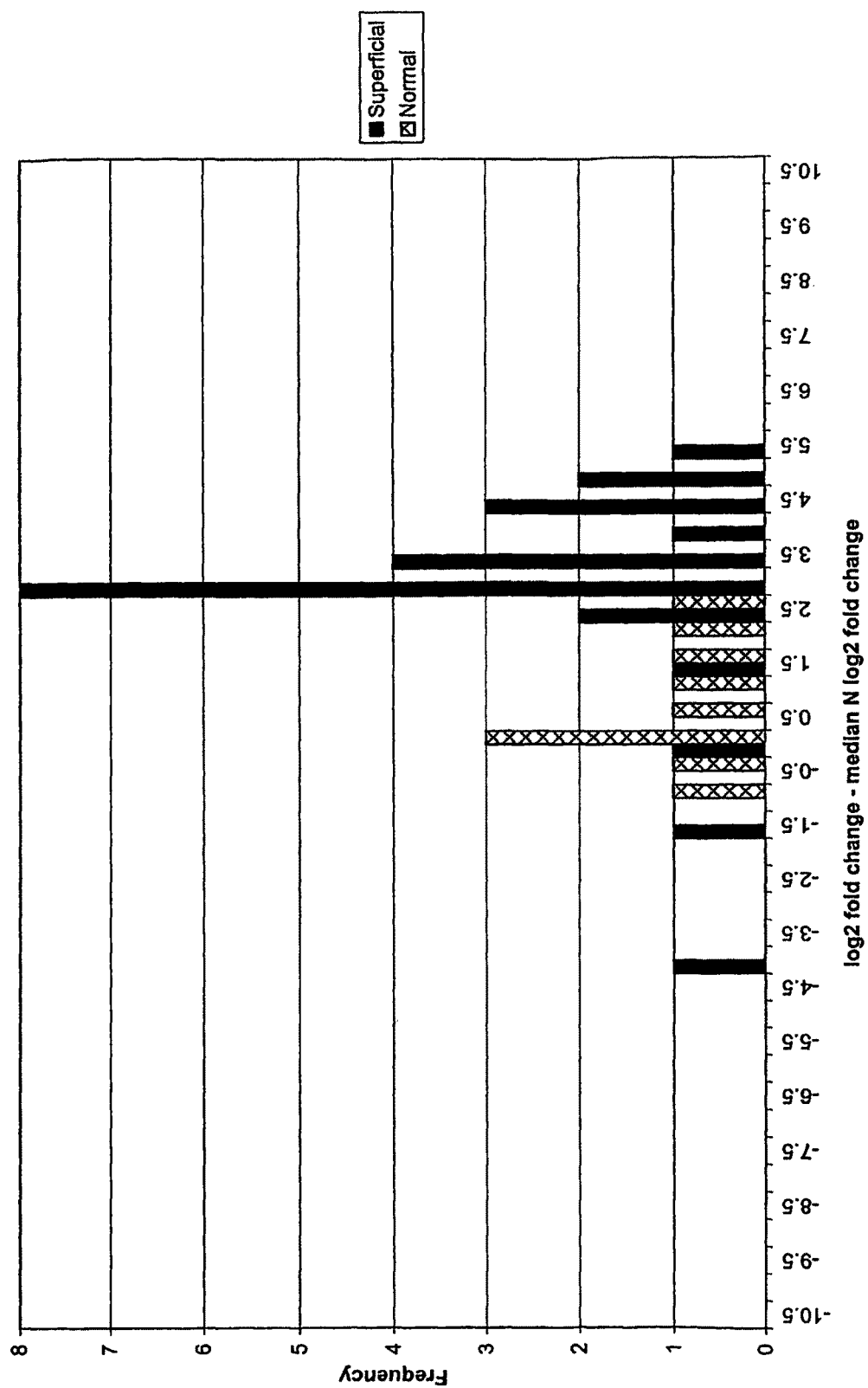

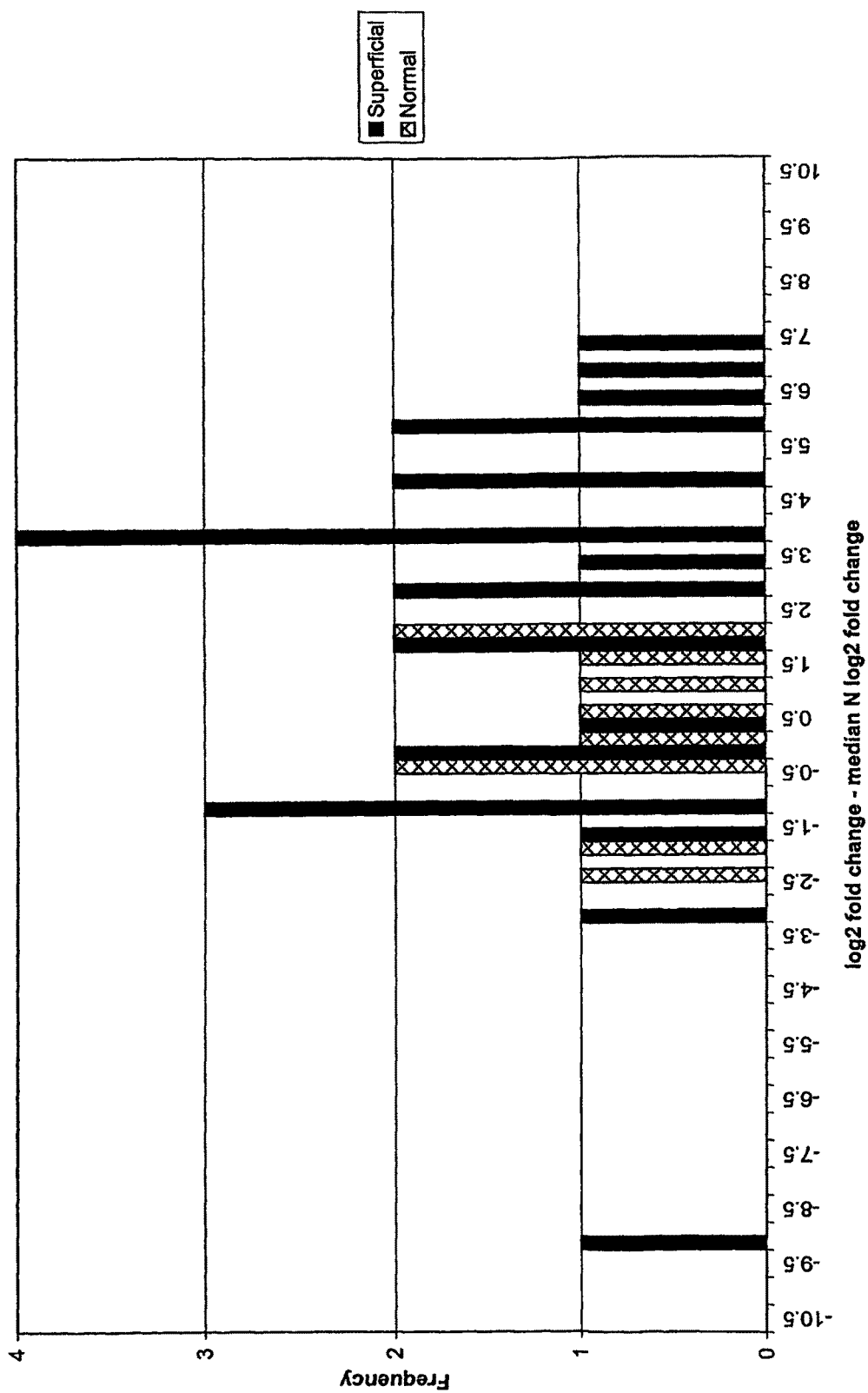

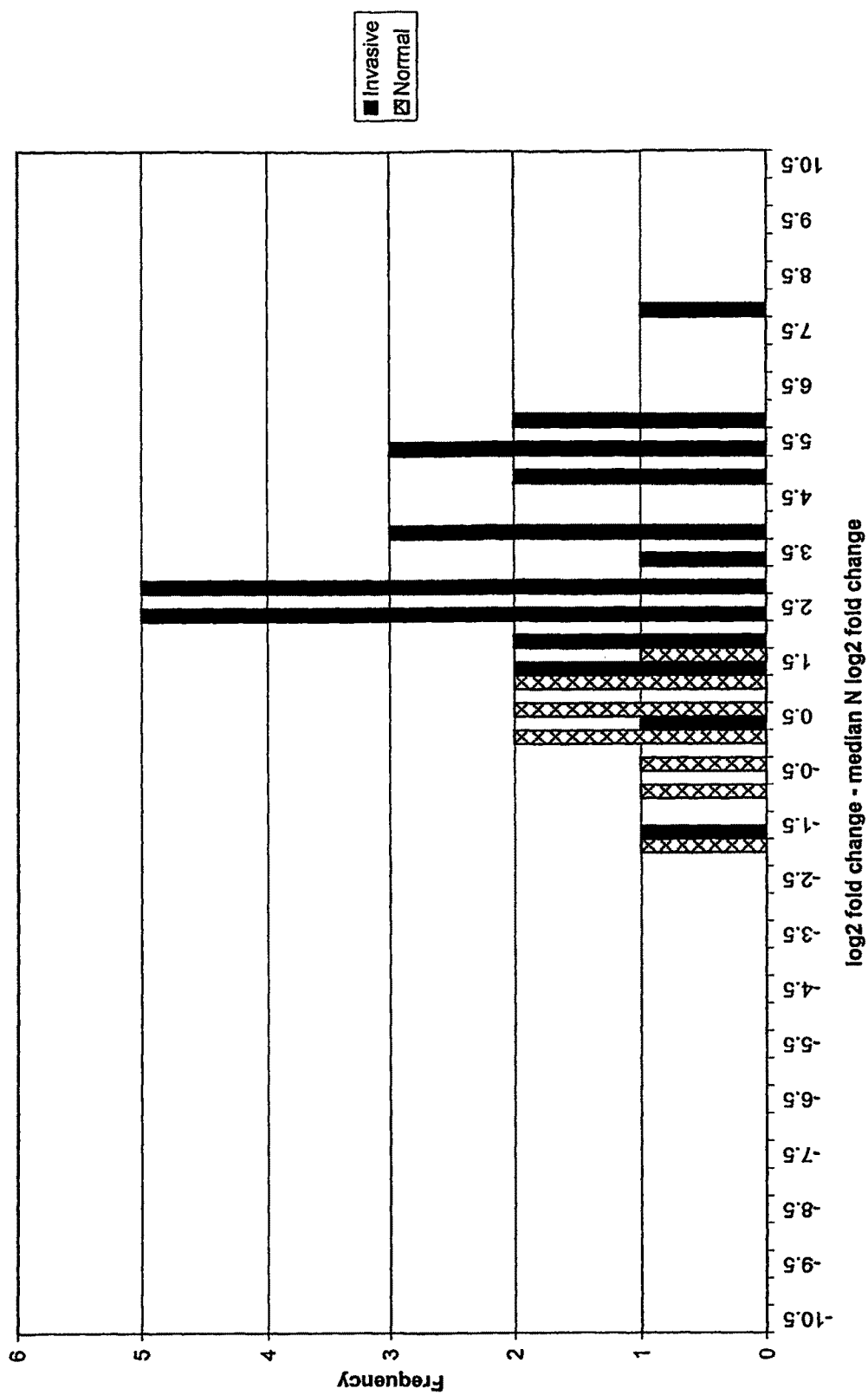

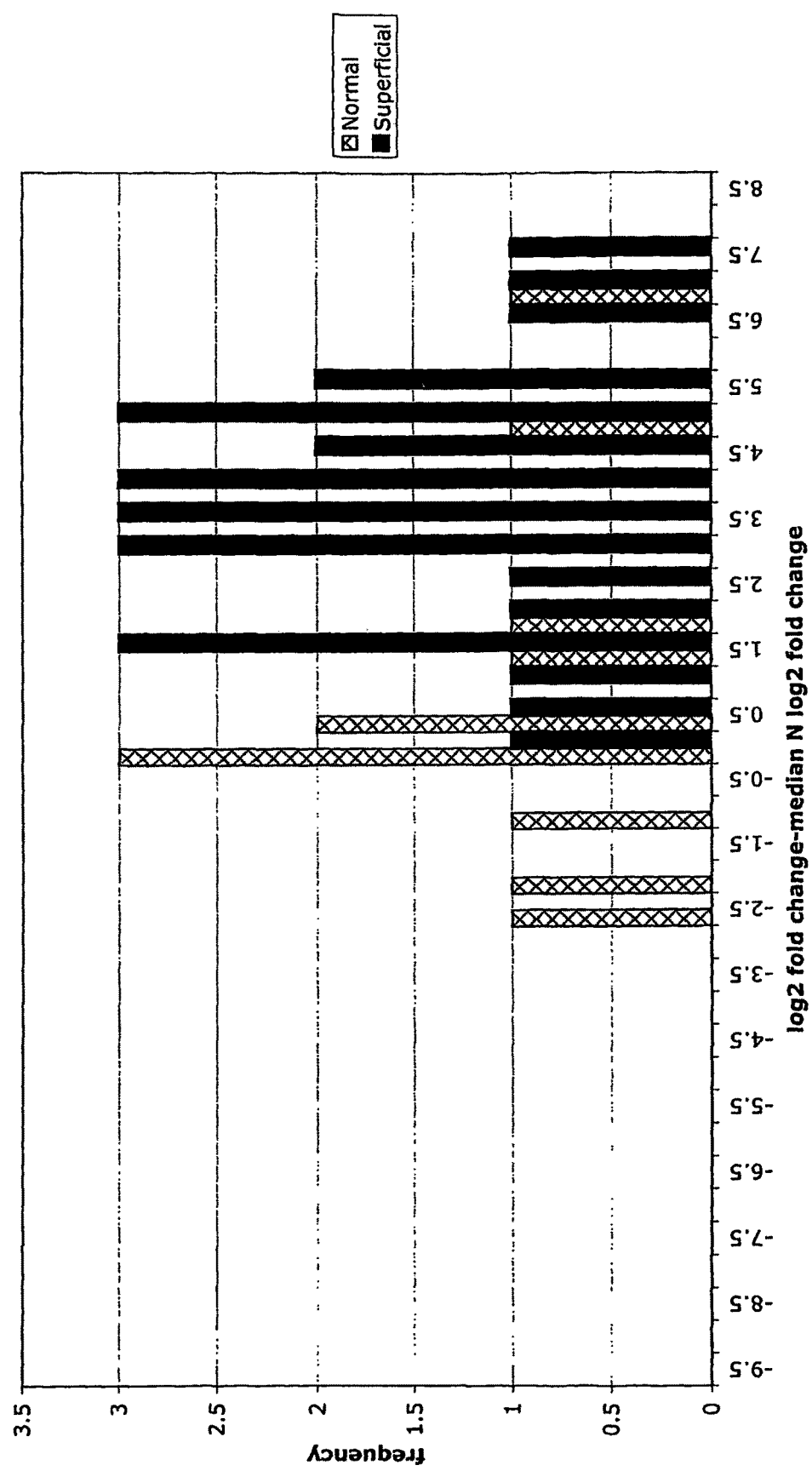

| Name | Symbol | Median patient:control fold change | Maximum patient:control fold change |
|---|---|---|---|
| sperm associated antigen 5 | SPAG5 | 8 | 304 |
| topoisomerase (DNA) II alpha 170kDa | TOP2A | 165 | 5716 |
| cell division cycle 2, G1 to S and G2 to M | CDC2 | 5 | 2370 |
| endoglin (Osler-Rendu-Weber syndrome 1) | ENG | 12 | 240 |
| insulin-like growth factor binding protein 5 | IGFBP5 | 85 | 14,862 |
| nephroblastoma overexpressed gene | NOV | 6 | 730 |
| neuropilin 1 | NRP1 | 43 | 380 |
| sema domain, immunoglobulin domain (Ig), short basic domain, secreted, (semaphorin) 3F | SEMA3F | 35 | 567 |
| EGF-like-domain, multiple 6 | EGFL6 | 1 | 1 |
| matrix Gla protein | MGP | 17 | 1147 |
| semaphorin sem2 | SEM2 | 5 | 501 |
| chromogranin A (parathyroid secretory protein 1) | CHGA | NT | NT |
| ubiquitin-conjugating enzyme E2C | UBE2C | 63 | 1461 |
| homeo box A13 | HOXA13 | 20 | 1221 |
| midkine (neurite growth-promoting factor 2) | MDK | 265 | 4188 |
| Thy-1 cell surface antigen | THY1 | 2 | 26 |
| baculoviral IAP repeat-containing 5 (survivin) | BIRC5 | 81 | 3524 |
| SMC4 structural maintenance of chromosomes 4-l | SMC4L1 | 13 | 232 |

Figure 7

| Marker | Median log2 difference | Median log2 difference |
|---|---|---|
| | patient : healthy control | patient : non malignant control |
| HoxA13 | 8 | 7.2 |
| IGFBP5 | 10.4 | 10.1 |
| NRP1 | 6.2 | 4.9 |
| Sema3F | 8.3 | 7.4 |
| Top2a | 6.3 | 6 |
| UBE2c | 6.4 | 4.6 |
| SMC4L1 | 5.4 | 4 |
| MDK | 10.1 | 7.7 |
| MGP | 7.1 | 7.2 |

Figure 10

| Number of markers in test | Total possible tests | Number of tests with sensitivity | | | Proportion of tests with sensitivity | | |
|---|---|---|---|---|---|---|---|
| | | >=90% | >=95% | >=99% | >=90% | >=95% | >=99% |
| 1 | 15 | 3 | 2 | 0 | 20% | 13% | 0% |
| 2 | 105 | 42 | 13 | 3 | 40% | 13% | 3% |
| 3 | 455 | 247 | 233 | 62 | 54% | 51% | 14% |

Figure 13a

| Number of markers in test | Total possible tests | Number of tests with sensitivity | | | Proportion of tests with sensitivity | | |
|---|---|---|---|---|---|---|---|
| | | >=90% | >=95% | >=99% | >=90% | >=95% | >=99% |
| 1 | 17 | 0 | 0 | 0 | 0% | 0% | 0% |
| 2 | 136 | 11 | 1 | 0 | 8% | 1% | 0% |
| 3 | 680 | 136 | 22 | 0 | 20% | 3% | 0% |

Figure 13b

Single marker

| Marker | Sensitivity |
|---|---|
| TOP2a | 96.6% |
| SPAG5 | 96.2% |
| CDC2 | 94.8% |
| NRP1 | 79.2% |
| CHGA | 70.6% |
| SEM2 | 55.2% |
| THY1 | 52.9% |
| SMC4L1 | 50.3% |
| MGP | 49.4% |
| MDK | 48.7% |
| ENG | 47.7% |
| UBE2c | 45.3% |
| EGFL6 | 39.2% |
| BIRC5 | 36.1% |
| HOXA13 | 32.6% |

Two marker combination

| Marker 1 | Marker 2 | Sensitivity |
|---|---|---|
| TOP2a | CDC2 | 99.4% |
| SPAG5 | TOP2A | 99.3% |
| SPAG5 | CDC2 | 99.3% |
| NRP1 | UBE2c | 98.1% |
| SPAG5 | MDK | 96.8% |
| TOP2a | THY1 | 96.7% |
| SPAG5 | CHGA | 96.6% |
| TOP2a | CHGA | 96.5% |
| SPAG5 | THY1 | 96.5% |
| TOP2a | MDK | 96.2% |
| CDC2 | CHGA | 95.4% |
| TOP2a | ENG | 95.3% |
| TOP2a | MGP | 95.1% |
| SPAG5 | NRP1 | 95.0% |
| SPAG5 | BIRC5 | 94.9% |
| TOP2a | NRP1 | 94.9% |
| SPAG5 | MGP | 94.8% |
| SPAG5 | EGFL6 | 94.8% |
| TOP2a | HOXA13 | 94.7% |
| TOP2a | EGFL6 | 94.7% |

Figure 14a

Two marker combination (cont.)

| Marker 1 | Marker 2 | Sensitivity |
|---|---|---|
| TOP2a | BIRC5 | 94.7% |
| SPAG5 | ENG | 94.6% |
| SPAG5 | HOXA13 | 94.4% |
| CDC2 | THY1 | 94.4% |
| CDC2 | MDK | 93.9% |
| SPAG5 | SEM2 | 93.8% |
| TOP2a | SMC4L1 | 93.7% |
| TOP2a | SEM2 | 93.6% |
| CDC2 | NRP1 | 93.6% |
| CDC2 | MGP | 93.3% |
| CDC2 | ENG | 93.1% |
| TOP2a | UBE2c | 92.8% |
| SPAG5 | UBE2c | 92.7% |
| CDC2 | EGFL6 | 92.4% |
| CDC2 | BIRC5 | 92.4% |
| SPAG5 | SMC4L1 | 92.4% |
| CDC2 | HOXA13 | 92.3% |
| CDC2 | SEM2 | 91.2% |
| NRP1 | MDK | 91.2% |
| NRP1 | THY1 | 90.6% |
| CDC2 | SMC4L1 | 90.6% |
| CDC2 | UBE2c | 90.0% |

Three marker combination

| Marker 1 | Marker 2 | Marker 3 | sensitivity |
|---|---|---|---|
| SPAG5 | TOP2a | CDC2 | 100.0% |
| SPAG5 | TOP2a | NRP1 | 99.9% |
| TOP2a | CDC2 | NRP1 | 99.9% |
| SPAG5 | TOP2a | CHGA | 99.9% |
| SPAG5 | CDC2 | NRP1 | 99.9% |
| TOP2a | CDC2 | CHGA | 99.9% |
| SPAG5 | TOP2a | SEM2 | 99.9% |
| SPAG5 | CDC2 | CHGA | 99.9% |
| SPAG5 | TOP2a | THY1 | 99.8% |
| SPAG5 | TOP2a | SMC4L1 | 99.8% |
| SPAG5 | TOP2a | MGP | 99.9% |
| SPAG5 | TOP2a | MDK | 99.9% |
| SPAG5 | TOP2a | ENG | 99.9% |
| SPAG5 | TOP2a | UBE2c | 99.8% |
| SPAG5 | TOP2a | EGFL6 | 99.8% |
| TOP2a | CDC2 | SEM2 | 99.8% |

Figure 14a (cont.)

Three marker combination (cont.)

| Marker 1 | Marker 2 | Marker 3 | sensitivity |
|---|---|---|---|
| SPAG5 | TOP2a | BIRC5 | 99.8% |
| TOP2a | CDC2 | THY1 | 99.7% |
| SPAG5 | TOP2a | HOXA13 | 99.8% |
| TOP2a | CDC2 | SMC4L1 | 99.8% |
| SPAG5 | CDC2 | SEM2 | 99.8% |
| TOP2a | CDC2 | MGP | 99.8% |
| TOP2a | CDC2 | MDK | 99.8% |
| TOP2a | CDC2 | ENG | 99.8% |
| SPAG5 | CDC2 | THY1 | 99.7% |
| TOP2a | CDC2 | UBE2c | 99.7% |
| SPAG5 | CDC2 | SMC4L1 | 99.8% |
| SPAG5 | CDC2 | MGP | 99.8% |
| SPAG5 | CDC2 | MDK | 99.8% |
| SPAG5 | CDC2 | ENG | 99.8% |
| TOP2a | CDC2 | EGFL6 | 99.7% |
| SPAG5 | CDC2 | UBE2c | 99.7% |
| TOP2a | CDC2 | BIRC5 | 99.7% |
| TOP2a | CDC2 | HOXA13 | 99.7% |
| SPAG5 | CDC2 | EGFL6 | 99.7% |
| SPAG5 | CDC2 | BIRC5 | 99.7% |
| SPAG5 | CDC2 | HOXA13 | 99.7% |
| TOP2a | NRP1 | CHGA | 99.5% |
| SPAG5 | NRP1 | CHGA | 99.5% |
| TOP2a | NRP1 | SEM2 | 99.2% |
| CDC2 | NRP1 | CHGA | 99.3% |
| TOP2a | NRP1 | THY1 | 98.9% |
| TOP2a | NRP1 | SMC4L1 | 99.1% |
| SPAG5 | NRP1 | SEM2 | 99.2% |
| TOP2a | NRP1 | MGP | 99.2% |
| TOP2a | NRP1 | MDK | 99.2% |
| TOP2a | ENG | NRP1 | 99.1% |
| SPAG5 | NRP1 | THY1 | 98.9% |
| TOP2a | NRP1 | UBE2c | 99.0% |
| SPAG5 | NRP1 | SMC4L1 | 99.1% |
| SPAG5 | NRP1 | MGP | 99.2% |
| SPAG5 | NRP1 | MDK | 99.2% |
| SPAG5 | ENG | NRP1 | 99.1% |
| TOP2a | NRP1 | EGFL6 | 99.0% |
| SPAG5 | NRP1 | UBE2c | 99.0% |
| TOP2a | SEM2 | CHGA | 99.1% |
| TOP2a | NRP1 | BIRC5 | 98.8% |

Figure 14a (cont.)

Three marker combination (cont.)

| Marker 1 | Marker 2 | Marker 3 | sensitivity |
|---|---|---|---|
| TOP2a | CHGA | THY1 | 98.8% |
| TOP2a | NRP1 | HOXA13 | 98.9% |
| SPAG5 | NRP1 | EGFL6 | 99.0% |
| CDC2 | NRP1 | SEM2 | 98.7% |
| TOP2a | CHGA | SMC4L1 | 99.0% |
| SPAG5 | SEM2 | CHGA | 99.1% |
| SPAG5 | NRP1 | BIRC5 | 98.8% |
| TOP2a | MGP | CHGA | 99.1% |
| CDC2 | NRP1 | THY1 | 98.3% |
| TOP2a | CHGA | MDK | 99.1% |
| TOP2a | ENG | CHGA | 99.0% |
| SPAG5 | CHGA | THY1 | 98.8% |
| SPAG5 | NRP1 | HOXA13 | 98.9% |
| CDC2 | NRP1 | SMC4L1 | 98.6% |
| TOP2a | CHGA | UBE2c | 98.9% |
| CDC2 | NRP1 | MGP | 98.7% |
| SPAG5 | CHGA | SMC4L1 | 99.0% |
| CDC2 | NRP1 | MDK | 98.7% |
| SPAG5 | MGP | CHGA | 99.1% |
| CDC2 | ENG | NRP1 | 98.6% |
| SPAG5 | CHGA | MDK | 99.1% |
| SPAG5 | ENG | CHGA | 99.0% |
| CDC2 | NRP1 | UBE2c | 98.5% |
| TOP2a | EGFL6 | CHGA | 98.9% |
| SPAG5 | CHGA | UBE2c | 98.9% |
| TOP2a | CHGA | BIRC5 | 98.7% |
| CDC2 | NRP1 | EGFL6 | 98.4% |
| TOP2a | CHGA | HOXA13 | 98.8% |
| SPAG5 | EGFL6 | CHGA | 98.9% |
| CDC2 | SEM2 | CHGA | 98.6% |
| CDC2 | NRP1 | BIRC5 | 98.1% |
| SPAG5 | CHGA | BIRC5 | 98.7% |
| TOP2a | SEM2 | THY1 | 97.8% |
| CDC2 | CHGA | THY1 | 98.1% |
| CDC2 | NRP1 | HOXA13 | 98.3% |
| SPAG5 | CHGA | HOXA13 | 98.8% |
| TOP2a | SEM2 | SMC4L1 | 98.2% |
| CDC2 | CHGA | SMC4L1 | 98.4% |
| TOP2a | MGP | SEM2 | 98.3% |
| CDC2 | MGP | CHGA | 98.5% |
| TOP2a | SEM2 | MDK | 98.4% |

Figure 14a (cont.)

Three marker combination (cont.)

| Marker 1 | Marker 2 | Marker 3 | sensitivity |
|---|---|---|---|
| CDC2 | CHGA | MDK | 98.6% |
| TOP2a | THY1 | SMC4L1 | 97.5% |
| TOP2a | ENG | SEM2 | 98.3% |
| SPAG5 | SEM2 | THY1 | 97.8% |
| CDC2 | ENG | CHGA | 98.5% |
| TOP2a | MGP | THY1 | 97.7% |
| TOP2a | MDK | THY1 | 97.8% |
| TOP2a | SEM2 | UBE2c | 98.1% |
| TOP2a | ENG | THY1 | 97.6% |
| CDC2 | CHGA | UBE2c | 98.3% |
| SPAG5 | SEM2 | SMC4L1 | 98.2% |
| TOP2a | MGP | SMC4L1 | 98.2% |
| SPAG5 | MGP | SEM2 | 98.3% |
| TOP2a | MDK | SMC4L1 | 98.2% |
| SPAG5 | SEM2 | MDK | 98.4% |
| TOP2a | UBE2c | THY1 | 97.4% |
| TOP2a | MGP | MDK | 98.3% |
| TOP2a | ENG | SMC4L1 | 98.1% |
| SPAG5 | THY1 | SMC4L1 | 97.5% |
| SPAG5 | ENG | SEM2 | 98.3% |
| TOP2a | ENG | MGP | 98.2% |
| SPAG5 | MGP | THY1 | 97.7% |
| TOP2a | ENG | MDK | 98.2% |
| SPAG5 | MDK | THY1 | 97.8% |
| TOP2a | UBE2c | SMC4L1 | 97.8% |
| TOP2a | EGFL6 | SEM2 | 98.0% |
| SPAG5 | SEM2 | UBE2c | 98.1% |
| SPAG5 | ENG | THY1 | 97.6% |
| CDC2 | EGFL6 | CHGA | 98.3% |
| TOP2a | MGP | UBE2c | 98.0% |
| SPAG5 | MGP | SMC4L1 | 98.1% |
| TOP2a | UBE2c | MDK | 98.1% |
| SPAG5 | MDK | SMC4L1 | 98.2% |
| TOP2a | EGFL6 | THY1 | 97.3% |
| TOP2a | ENG | UBE2c | 97.9% |
| TOP2a | SEM2 | BIRC5 | 97.7% |
| SPAG5 | UBE2c | THY1 | 97.3% |
| CDC2 | CHGA | BIRC5 | 97.9% |
| SPAG5 | MGP | MDK | 98.3% |
| SPAG5 | ENG | SMC4L1 | 98.1% |
| SPAG5 | ENG | MGP | 98.2% |

Figure 14a (cont.)

Three marker combination (cont.)

| Marker 1 | Marker 2 | Marker 3 | sensitivity |
|---|---|---|---|
| SPAG5 | ENG | MDK | 98.2% |
| TOP2a | BIRC5 | THY1 | 96.8% |
| TOP2a | SEM2 | HOXA13 | 97.8% |
| TOP2a | EGFL6 | SMC4L1 | 97.8% |
| SPAG5 | UBE2c | SMC4L1 | 97.8% |
| SPAG5 | EGFL6 | SEM2 | 98.0% |
| CDC2 | CHGA | HOXA13 | 98.1% |
| TOP2a | EGFL6 | MGP | 98.0% |
| SPAG5 | MGP | UBE2c | 98.0% |
| TOP2a | EGFL6 | MDK | 98.0% |
| SPAG5 | UBE2c | MDK | 98.1% |
| TOP2a | HOXA13 | THY1 | 97.0% |
| TOP2a | BIRC5 | SMC4L1 | 97.4% |
| TOP2a | ENG | EGFL6 | 97.9% |
| SPAG5 | EGFL6 | THY1 | 97.3% |
| SPAG5 | ENG | UBE2c | 97.9% |
| SPAG5 | SEM2 | BIRC5 | 97.6% |
| TOP2a | MGP | BIRC5 | 97.6% |
| CDC2 | SEM2 | THY1 | 96.6% |
| TOP2a | BIRC5 | MDK | 97.6% |
| TOP2a | EGFL6 | UBE2c | 97.6% |
| TOP2a | ENG | BIRC5 | 97.4% |
| TOP2a | HOXA13 | SMC4L1 | 97.5% |
| SPAG5 | BIRC5 | THY1 | 96.8% |
| SPAG5 | SEM2 | HOXA13 | 97.8% |
| SPAG5 | EGFL6 | SMC4L1 | 97.8% |
| TOP2a | MGP | HOXA13 | 97.7% |
| CDC2 | SEM2 | SMC4L1 | 97.2% |
| SPAG5 | EGFL6 | MGP | 98.0% |
| TOP2a | HOXA13 | MDK | 97.8% |
| SPAG5 | EGFL6 | MDK | 98.0% |
| CDC2 | MGP | SEM2 | 97.4% |
| TOP2a | BIRC5 | UBE2c | 97.2% |
| TOP2a | ENG | HOXA13 | 97.6% |
| SPAG5 | HOXA13 | THY1 | 97.0% |
| CDC2 | SEM2 | MDK | 97.5% |
| SPAG5 | BIRC5 | SMC4L1 | 97.4% |
| SPAG5 | ENG | EGFL6 | 97.9% |
| CDC2 | THY1 | SMC4L1 | 96.2% |
| CDC2 | ENG | SEM2 | 97.3% |
| SPAG5 | MGP | BIRC5 | 97.6% |

Figure 14a (cont.)

Three marker combination (cont.)

| Marker 1 | Marker 2 | Marker 3 | sensitivity |
|---|---|---|---|
| SPAG5 | BIRC5 | MDK | 97.6% |
| CDC2 | MGP | THY1 | 96.4% |
| TOP2a | UBE2c | HOXA13 | 97.4% |
| CDC2 | MDK | THY1 | 96.5% |
| SPAG5 | EGFL6 | UBE2c | 97.6% |
| SPAG5 | ENG | BIRC5 | 97.4% |
| SPAG5 | HOXA13 | SMC4L1 | 97.5% |
| CDC2 | SEM2 | UBE2c | 97.0% |
| CDC2 | ENG | THY1 | 96.3% |
| SPAG5 | MGP | HOXA13 | 97.7% |
| SPAG5 | HOXA13 | MDK | 97.8% |
| CDC2 | MGP | SMC4L1 | 97.1% |
| TOP2a | EGFL6 | BIRC5 | 97.1% |
| SPAG5 | BIRC5 | UBE2c | 97.2% |
| CDC2 | MDK | SMC4L1 | 97.2% |
| SPAG5 | ENG | HOXA13 | 97.6% |
| CDC2 | UBE2c | THY1 | 95.9% |
| CDC2 | MGP | MDK | 97.4% |
| CDC2 | ENG | SMC4L1 | 97.0% |
| CDC2 | ENG | MGP | 97.2% |
| TOP2a | EGFL6 | HOXA13 | 97.3% |
| SPAG5 | UBE2c | HOXA13 | 97.3% |
| CDC2 | ENG | MDK | 97.3% |
| CDC2 | UBE2c | SMC4L1 | 96.6% |
| CDC2 | EGFL6 | SEM2 | 96.9% |
| CDC2 | MGP | UBE2c | 96.9% |
| TOP2a | BIRC5 | HOXA13 | 96.8% |
| CDC2 | UBE2c | MDK | 97.0% |
| SPAG5 | EGFL6 | BIRC5 | 97.1% |
| CDC2 | EGFL6 | THY1 | 95.8% |
| CDC2 | ENG | UBE2c | 96.7% |
| CDC2 | SEM2 | BIRC5 | 96.3% |
| SPAG5 | EGFL6 | HOXA13 | 97.3% |
| CDC2 | BIRC5 | THY1 | 95.0% |
| CDC2 | SEM2 | HOXA13 | 96.6% |
| CDC2 | EGFL6 | SMC4L1 | 96.6% |
| CDC2 | EGFL6 | MGP | 96.8% |
| CDC2 | EGFL6 | MDK | 96.9% |
| SPAG5 | BIRC5 | HOXA13 | 96.8% |
| CDC2 | HOXA13 | THY1 | 95.3% |
| CDC2 | BIRC5 | SMC4L1 | 95.9% |

Figure 14a (cont.)

Three marker combination (cont.)

| Marker 1 | Marker 2 | Marker 3 | sensitivity |
|---|---|---|---|
| CDC2 | ENG | EGFL6 | 96.7% |
| CDC2 | MGP | BIRC5 | 96.2% |
| CDC2 | BIRC5 | MDK | 96.3% |
| CDC2 | EGFL6 | UBE2c | 96.3% |
| CDC2 | ENG | BIRC5 | 96.0% |
| CDC2 | HOXA13 | SMC4L1 | 96.2% |
| CDC2 | MGP | HOXA13 | 96.4% |
| CDC2 | HOXA13 | MDK | 96.5% |
| CDC2 | BIRC5 | UBE2c | 95.6% |
| CDC2 | ENG | HOXA13 | 96.3% |
| CDC2 | UBE2c | HOXA13 | 95.9% |
| CDC2 | EGFL6 | BIRC5 | 95.5% |
| CDC2 | EGFL6 | HOXA13 | 95.8% |
| CDC2 | BIRC5 | HOXA13 | 95.0% |
| NRP1 | SEM2 | CHGA | 94.6% |
| NRP1 | CHGA | THY1 | 92.6% |
| NRP1 | CHGA | SMC4L1 | 94.0% |
| NRP1 | MGP | CHGA | 94.4% |
| NRP1 | CHGA | MDK | 94.6% |
| ENG | NRP1 | CHGA | 94.1% |
| NRP1 | CHGA | UBE2c | 93.5% |
| NRP1 | EGFL6 | CHGA | 93.4% |
| NRP1 | CHGA | BIRC5 | 92.1% |
| NRP1 | CHGA | HOXA13 | 92.6% |
| NRP1 | SEM2 | THY1 | 86.8% |
| NRP1 | SEM2 | SMC4L1 | 89.3% |
| NRP1 | MGP | SEM2 | 90.0% |
| NRP1 | SEM2 | MDK | 90.3% |

Figure 14a (cont.)

Single marker

| Marker | Sensitivity |
|---|---|
| TOP2a | 84.5% |
| CHGA | 63.7% |
| NRP1 | 66.9% |
| ENG | 62.2% |
| SPAG5 | 64.8% |
| SEM2 | 71.0% |
| MDK | 43.4% |
| HOXA13 | 56.8% |
| IGFBP5 | 44.4% |
| SEMA3F | 39.7% |
| EGFL6 | 40.6% |
| SMC4L1 | 35.8% |
| NOV | 26.6% |
| UBE2c | 26.8% |
| BIRC5 | 18.8% |
| THY1 | 30.9% |

Two marker combination

| Marker 1 | Marker 2 | Sensitivity |
|---|---|---|
| CDC2 | TOP2a | 95.4% |
| TOP2a | SEM2 | 91.2% |
| CDC2 | SEM2 | 90.7% |
| TOP2a | NRP1 | 91.9% |
| TOP2a | SPAG5 | 91.2% |
| TOP2a | CHGA | 92.2% |
| CDC2 | NRP1 | 91.5% |
| TOP2a | ENG | 90.9% |
| CDC2 | SPAG5 | 90.7% |
| CDC2 | CHGA | 91.8% |
| CDC2 | ENG | 90.4% |

Three marker combination

| Marker 1 | Marker 2 | Marker 3 | sensitivity |
|---|---|---|---|
| CDC2 | TOP2a | CHGA | 97.8% |
| CDC2 | TOP2a | NRP1 | 97.5% |
| CDC2 | TOP2a | SPAG5 | 97.3% |
| CDC2 | TOP2a | ENG | 97.2% |
| CDC2 | TOP2a | SEM2 | 97.0% |
| HOXA13 | CDC2 | TOP2a | 96.6% |

Figure 14b

Three marker combination (cont.)

| Marker 1 | Marker 2 | Marker 3 | sensitivity |
|---|---|---|---|
| CDC2 | TOP2a | MDK | *96.4%* |
| CDC2 | TOP2a | IGFBP5 | *96.3%* |
| TOP2a | NRP1 | CHGA | *96.2%* |
| CDC2 | TOP2a | SEMA3F | *96.1%* |
| CDC2 | NRP1 | CHGA | *96.1%* |
| CDC2 | TOP2a | EGFL6 | *95.8%* |
| TOP2a | SPAG5 | CHGA | *95.8%* |
| TOP2a | ENG | CHGA | *95.7%* |
| CDC2 | SPAG5 | CHGA | *95.6%* |
| CDC2 | ENG | CHGA | *95.6%* |
| CDC2 | TOP2a | SMC4L1 | *95.4%* |
| TOP2a | SEM2 | CHGA | *95.4%* |
| TOP2a | NRP1 | SPAG5 | *95.3%* |
| CDC2 | SEM2 | CHGA | *95.3%* |
| TOP2a | NRP1 | ENG | *95.2%* |
| CDC2 | NRP1 | SPAG5 | *95.2%* |
| CDC2 | NRP1 | ENG | *95.1%* |
| TOP2a | NRP1 | SEM2 | *94.9%* |
| CDC2 | TOP2a | NOV | *94.9%* |
| CDC2 | NRP1 | SEM2 | *94.8%* |
| UBE2c | CDC2 | TOP2a | *94.8%* |
| TOP2a | ENG | SPAG5 | *94.7%* |
| HOXA13 | TOP2a | CHGA | *94.7%* |
| CDC2 | ENG | SPAG5 | *94.6%* |
| CDC2 | TOP2a | THY1 | *94.6%* |
| HOXA13 | CDC2 | CHGA | *94.5%* |
| BIRC5 | CDC2 | TOP2a | *94.5%* |
| TOP2a | SPAG5 | SEM2 | *94.4%* |
| TOP2a | MDK | CHGA | *94.4%* |
| TOP2a | ENG | SEM2 | *94.3%* |
| CDC2 | SPAG5 | SEM2 | *94.3%* |
| TOP2a | IGFBP5 | CHGA | *94.2%* |
| CDC2 | MDK | CHGA | *94.2%* |
| CDC2 | ENG | SEM2 | *94.2%* |
| HOXA13 | TOP2a | NRP1 | *94.1%* |
| CDC2 | IGFBP5 | CHGA | *94.1%* |
| HOXA13 | CDC2 | NRP1 | *94.0%* |
| TOP2a | SEMA3F | CHGA | *93.9%* |
| TOP2a | NRP1 | MDK | *93.8%* |
| CDC2 | SEMA3F | CHGA | *93.7%* |
| TOP2a | NRP1 | IGFBP5 | *93.6%* |

Figure 14b (cont.)

Three marker combination (cont.)

| Marker 1 | Marker 2 | Marker 3 | sensitivity |
|---|---|---|---|
| CDC2 | NRP1 | MDK | _93.6%_ |
| HOXA13 | TOP2a | SPAG5 | _93.5%_ |
| TOP2a | EGFL6 | CHGA | _93.5%_ |
| CDC2 | NRP1 | IGFBP5 | _93.4%_ |
| HOXA13 | TOP2a | ENG | _93.4%_ |
| HOXA13 | CDC2 | SPAG5 | _93.3%_ |
| CDC2 | EGFL6 | CHGA | _93.3%_ |
| TOP2a | NRP1 | SEMA3F | _93.3%_ |
| HOXA13 | CDC2 | ENG | _93.3%_ |
| TOP2a | SPAG5 | MDK | _93.1%_ |
| CDC2 | NRP1 | SEMA3F | _93.1%_ |
| TOP2a | ENG | MDK | _93.0%_ |
| HOXA13 | TOP2a | SEM2 | _93.0%_ |
| TOP2a | SPAG5 | IGFBP5 | _92.9%_ |
| TOP2a | SMC4L1 | CHGA | _92.9%_ |
| CDC2 | SPAG5 | MDK | _92.9%_ |
| TOP2a | ENG | IGFBP5 | _92.9%_ |
| CDC2 | ENG | MDK | _92.8%_ |
| HOXA13 | CDC2 | SEM2 | _92.8%_ |
| TOP2a | NRP1 | EGFL6 | _92.8%_ |
| CDC2 | SPAG5 | IGFBP5 | _92.7%_ |
| CDC2 | SMC4L1 | CHGA | _92.7%_ |
| CDC2 | ENG | IGFBP5 | _92.7%_ |
| CDC2 | NRP1 | EGFL6 | _92.6%_ |
| TOP2a | SEM2 | MDK | _92.6%_ |
| TOP2a | SPAG5 | SEMA3F | _92.6%_ |
| NRP1 | SPAG5 | CHGA | _92.5%_ |
| TOP2a | ENG | SEMA3F | _92.5%_ |
| NRP1 | ENG | CHGA | _92.5%_ |
| TOP2a | SEM2 | IGFBP5 | _92.4%_ |
| CDC2 | SEM2 | MDK | _92.4%_ |
| CDC2 | SPAG5 | SEMA3F | _92.4%_ |
| CDC2 | ENG | SEMA3F | _92.3%_ |
| TOP2a | NRP1 | SMC4L1 | _92.2%_ |
| CDC2 | SEM2 | IGFBP5 | _92.2%_ |
| TOP2a | NOV | CHGA | _92.1%_ |
| TOP2a | SPAG5 | EGFL6 | _92.0%_ |
| TOP2a | SEM2 | SEMA3F | _92.0%_ |
| CDC2 | NRP1 | SMC4L1 | _92.0%_ |
| NRP1 | SEM2 | CHGA | _92.0%_ |
| UBE2c | TOP2a | CHGA | _91.9%_ |

Figure 14b (cont.)

Three marker combination (cont.)

| Marker 1 | Marker 2 | Marker 3 | sensitivity |
|---|---|---|---|
| TOP2a | ENG | EGFL6 | 91.9% |
| CDC2 | NOV | CHGA | 91.9% |
| CDC2 | SPAG5 | EGFL6 | 91.8% |
| CDC2 | SEM2 | SEMA3F | 91.8% |
| UBE2c | CDC2 | CHGA | 91.7% |
| CDC2 | ENG | EGFL6 | 91.7% |
| ENG | SPAG5 | CHGA | 91.7% |
| TOP2a | THY1 | CHGA | 91.6% |
| BIRC5 | THY1 | CHGA | 91.5% |
| TOP2a | EGFL6 | SEM2 | 91.4% |
| HOXA13 | TOP2a | MDK | 91.4% |
| TOP2a | SPAG5 | SMC4L1 | 91.4% |
| CDC2 | THY1 | CHGA | 91.3% |
| TOP2a | NRP1 | NOV | 91.3% |
| TOP2a | ENG | SMC4L1 | 91.3% |
| BIRC5 | CDC2 | CHGA | 91.2% |
| HOXA13 | TOP2a | IGFBP5 | 91.2% |
| CDC2 | EGFL6 | SEM2 | 91.2% |
| HOXA13 | CDC2 | MDK | 91.2% |
| CDC2 | SPAG5 | SMC4L1 | 91.1% |
| SPAG5 | SEM2 | CHGA | 91.1% |
| UBE2c | TOP2a | NRP1 | 91.1% |
| CDC2 | NRP1 | NOV | 91.0% |
| CDC2 | ENG | SMC4L1 | 91.0% |
| ENG | SEM2 | CHGA | 91.0% |
| HOXA13 | CDC2 | IGFBP5 | 90.9% |
| UBE2c | CDC2 | NRP1 | 90.9% |
| NRP1 | ENG | SPAG5 | 90.8% |
| HOXA13 | TOP2a | SEMA3F | 90.7% |
| TOP2a | SEM2 | SMC4L1 | 90.7% |
| TOP2a | NRP1 | THY1 | 90.7% |
| HOXA13 | NRP1 | CHGA | 90.7% |
| TOP2a | MDK | IGFBP5 | 90.6% |
| BIRC5 | TOP2a | NRP1 | 90.6% |
| HOXA13 | CDC2 | SEMA3F | 90.5% |
| CDC2 | SEM2 | SMC4L1 | 90.4% |
| CDC2 | NRP1 | THY1 | 90.4% |
| CDC2 | MDK | IGFBP5 | 90.4% |
| TOP2a | NOV | SPAG5 | 90.4% |
| BIRC5 | CDC2 | NRP1 | 90.3% |
| TOP2a | ENG | NOV | 90.2% |

Figure 14b (cont.)

Three marker combination (cont.)

| Marker 1 | Marker 2 | Marker 3 | sensitivity |
|---|---|---|---|
| NRP1 | SPAG5 | SEM2 | *90.2%* |
| UBE2c | TOP2a | SPAG5 | *90.2%* |
| TOP2a | MDK | SEMA3F | *90.1%* |
| NRP1 | MDK | CHGA | *90.1%* |
| CDC2 | NOV | SPAG5 | *90.1%* |
| NRP1 | ENG | SEM2 | *90.1%* |
| HOXA13 | TOP2a | EGFL6 | *90.0%* |
| UBE2c | TOP2a | ENG | *90.0%* |
| CDC2 | ENG | NOV | *90.0%* |

Figure 14b (cont.)

| Number of markers in test | Total possible tests | Number of tests with sensitivity | | | Proportion of tests with sensitivity | | |
|---|---|---|---|---|---|---|---|
| | | >=90% | >=95% | >=99% | >=90% | >=95% | >=99% |
| 1 | 9 | 1 | 1 | 0 | 11% | 11% | 0% |
| 2 | 36 | 15 | 8 | 2 | 42% | 22% | 6% |
| 3 | 84 | 59 | 37 | 13 | 70% | 44% | 16% |

Figure 15

Sensitivity of marker combinations in urine for the detection of bladder cancer at a specificity of 95%

Single marker

| Marker | Sensitivity (%) |
|---|---|
| IGFBP5 | 98 |
| HoxA13 | 85 |
| Sema3F | 80 |
| UBE2c | 42 |
| NRP1 | 37 |
| Top2a | 74 |
| SMC4L1 | 34 |
| MDK | 79 |
| MGP | 70 |

Two marker combinations

| Marker 1 | Marker 2 | Sensitivity (%) |
|---|---|---|
| IGFBP5 | HoxA13 | 99.2 |
| IGFBP5 | Sema3F | 99.0 |
| IGFBP5 | MDK | 98.9 |
| IGFBP5 | Top2a | 98.9 |
| IGFBP5 | MGP | 98.6 |
| IGFBP5 | UBE2c | 97.5 |
| IGFBP5 | NRP1 | 97.3 |
| IGFBP5 | SMC4L1 | 97.2 |
| HoxA13 | Sema3F | 94.0 |
| HoxA13 | MDK | 93.5 |
| HoxA13 | Top2a | 93.1 |
| Sema3F | MDK | 92.2 |
| Sema3F | Top2a | 91.7 |
| HoxA13 | MGP | 91.3 |
| Top2a | MDK | 91.0 |

Three marker combinations

| Marker 1 | Marker 2 | Marker 3 | Sensitivity (%) |
|---|---|---|---|
| IGFBP5 | HoxA13 | Sema3F | 99.6 |
| IGFBP5 | HoxA13 | Top2a | 99.6 |
| IGFBP5 | HoxA13 | MDK | 99.6 |
| IGFBP5 | Sema3F | Top2a | 99.5 |
| IGFBP5 | Sema3F | MDK | 99.5 |
| IGFBP5 | Top2a | MDK | 99.5 |

Figure 16A

| | | | |
|---|---|---|---|
| IGFBP5 | HoxA13 | MGP | 99.5 |
| IGFBP5 | Sema3F | MGP | 99.4 |
| IGFBP5 | Top2a | MGP | 99.3 |
| IGFBP5 | MDK | MGP | 99.3 |
| IGFBP5 | HoxA13 | UBE2c | 99.1 |
| IGFBP5 | HoxA13 | NRP1 | 99.0 |
| IGFBP5 | HoxA13 | SMC4L1 | 99.0 |
| IGFBP5 | Sema3F | UBE2c | 99.0 |
| IGFBP5 | UBE2c | Top2a | 98.9 |
| IGFBP5 | Sema3F | NRP1 | 98.9 |
| IGFBP5 | UBE2c | MDK | 98.9 |
| IGFBP5 | Sema3F | SMC4L1 | 98.9 |
| IGFBP5 | NRP1 | Top2a | 98.8 |
| IGFBP5 | NRP1 | MDK | 98.8 |
| IGFBP5 | Top2a | SMC4L1 | 98.8 |
| IGFBP5 | SMC4L1 | MDK | 98.8 |
| IGFBP5 | UBE2c | MGP | 98.5 |
| IGFBP5 | NRP1 | MGP | 98.4 |
| IGFBP5 | SMC4L1 | MGP | 98.4 |
| IGFBP5 | UBE2c | NRP1 | 97.3 |
| IGFBP5 | UBE2c | SMC4L1 | 97.3 |
| HoxA13 | Sema3F | Top2a | 97.2 |
| HoxA13 | Sema3F | MDK | 97.2 |
| IGFBP5 | NRP1 | SMC4L1 | 97.1 |
| HoxA13 | Top2a | MDK | 97.0 |
| Sema3F | Top2a | MDK | 96.5 |
| HoxA13 | Sema3F | MGP | 96.3 |
| HoxA13 | Top2a | MGP | 96.0 |
| HoxA13 | MDK | MGP | 96.0 |
| Sema3F | Top2a | MGP | 95.3 |
| Sema3F | MDK | MGP | 95.3 |
| Top2a | MDK | MGP | 94.9 |
| HoxA13 | Sema3F | UBE2c | 93.9 |
| HoxA13 | UBE2c | Top2a | 93.4 |
| HoxA13 | Sema3F | NRP1 | 93.4 |
| HoxA13 | UBE2c | MDK | 93.3 |
| HoxA13 | Sema3F | SMC4L1 | 93.3 |
| HoxA13 | NRP1 | Top2a | 92.8 |
| HoxA13 | NRP1 | MDK | 92.7 |
| HoxA13 | Top2a | SMC4L1 | 92.7 |
| HoxA13 | SMC4L1 | MDK | 92.7 |
| Sema3F | UBE2c | Top2a | 92.3 |
| Sema3F | UBE2c | MDK | 92.3 |
| Sema3F | NRP1 | Top2a | 91.6 |

Figure 16B

| Marker 1 | Marker 2 | Marker 3 | Sensitivity (%) |
|---|---|---|---|
| UBE2c | Top2a | MDK | 91.6 |
| Sema3F | NRP1 | MDK | 91.6 |
| Sema3F | Top2a | SMC4L1 | 91.6 |
| Sema3F | SMC4L1 | MDK | 91.6 |
| HoxA13 | UBE2c | MGP | 91.2 |
| NRP1 | Top2a | MDK | 90.9 |
| Top2a | SMC4L1 | MDK | 90.8 |
| HoxA13 | NRP1 | MGP | 90.4 |
| HoxA13 | SMC4L1 | MGP | 90.4 |

Figure 16C

SEQUENCE LISTING

```
<160> NUMBER OF SEQ ID NOS: 39

<210> SEQ ID NO 1
<211> LENGTH: 22
<212> TYPE: DNA
<213> ORGANISM: HUMAN
```

```
<400> SEQUENCE: 1
aattcagagg ccttctgaag ga                                       22

<210> SEQ ID NO 2
<211> LENGTH: 20
<212> TYPE: DNA
<213> ORGANISM: HUMAN

<400> SEQUENCE: 2
ccgcccagac acctacattg                                          20

<210> SEQ ID NO 3
<211> LENGTH: 16
<212> TYPE: DNA
<213> ORGANISM: HUMAN

<400> SEQUENCE: 3
gccgccgcgg aataat                                              16

<210> SEQ ID NO 4
<211> LENGTH: 23
<212> TYPE: DNA
<213> ORGANISM: HUMAN

<400> SEQUENCE: 4
gcaggtgtca gcaagtatga tca                                      23

<210> SEQ ID NO 5
<211> LENGTH: 22
<212> TYPE: DNA
<213> ORGANISM: HUMAN

<400> SEQUENCE: 5
aattgtgacc gcaaaggatt ct                                       22

<210> SEQ ID NO 6
<211> LENGTH: 16
<212> TYPE: DNA
<213> ORGANISM: HUMAN

<400> SEQUENCE: 6
cggaccccag caacca                                              16

<210> SEQ ID NO 7
<211> LENGTH: 22
<212> TYPE: DNA
<213> ORGANISM: HUMAN

<400> SEQUENCE: 7
ggagtgtgtt gaccagcaag ac                                       22

<210> SEQ ID NO 8
<211> LENGTH: 25
<212> TYPE: DNA
<213> ORGANISM: HUMAN

<400> SEQUENCE: 8
cctgtcattt acgctgtctt tacct                                    25

<210> SEQ ID NO 9
<211> LENGTH: 18
<212> TYPE: DNA
<213> ORGANISM: HUMAN
```

-continued

<400> SEQUENCE: 9
tgctctcctg ggtggcag                                                  18

<210> SEQ ID NO 10
<211> LENGTH: 23
<212> TYPE: DNA
<213> ORGANISM: HUMAN

<400> SEQUENCE: 10
ttcatatccc ctcagcagag atg                                            23

<210> SEQ ID NO 11
<211> LENGTH: 19
<212> TYPE: DNA
<213> ORGANISM: HUMAN

<400> SEQUENCE: 11
ctcgaggtgt acgcgctgt                                                 19

<210> SEQ ID NO 12
<211> LENGTH: 21
<212> TYPE: DNA
<213> ORGANISM: HUMAN

<400> SEQUENCE: 12
tacaaggaga tccggaaagg c                                              21

<210> SEQ ID NO 13
<211> LENGTH: 19
<212> TYPE: DNA
<213> ORGANISM: HUMAN

<400> SEQUENCE: 13
tgaacctggc catcagcat                                                 19

<210> SEQ ID NO 14
<211> LENGTH: 22
<212> TYPE: DNA
<213> ORGANISM: HUMAN

<400> SEQUENCE: 14
tctgctgaac cagctcttct tg                                             22

<210> SEQ ID NO 15
<211> LENGTH: 26
<212> TYPE: DNA
<213> ORGANISM: HUMAN

<400> SEQUENCE: 15
ccctatagtt aatgccaaca tcttca                                         26

<210> SEQ ID NO 16
<211> LENGTH: 26
<212> TYPE: DNA
<213> ORGANISM: HUMAN

<400> SEQUENCE: 16
accttctcca attttctcta ttttgg                                         26

<210> SEQ ID NO 17
<211> LENGTH: 21
<212> TYPE: DNA

```
<213> ORGANISM: HUMAN

<400> SEQUENCE: 17
atgttgaggc agtgcacctt t                                        21

<210> SEQ ID NO 18
<211> LENGTH: 18
<212> TYPE: DNA
<213> ORGANISM: HUMAN

<400> SEQUENCE: 18
cagcagatgc cacgcttg                                            18

<210> SEQ ID NO 19
<211> LENGTH: 23
<212> TYPE: DNA
<213> ORGANISM: MOUSE

<400> SEQUENCE: 19
ccccatcgaa cacacagtta tct                                      23

<210> SEQ ID NO 20
<211> LENGTH: 23
<212> TYPE: DNA
<213> ORGANISM: HUMAN

<400> SEQUENCE: 20
cgtcagcttg ggaatagatg aag                                      23

<210> SEQ ID NO 21
<211> LENGTH: 23
<212> TYPE: DNA
<213> ORGANISM: HUMAN

<400> SEQUENCE: 21
gcgaatatca gccatggagt aga                                      23

<210> SEQ ID NO 22
<211> LENGTH: 21
<212> TYPE: DNA
<213> ORGANISM: HUMAN

<400> SEQUENCE: 22
tagtgacaga ccccaggctg a                                        21

<210> SEQ ID NO 23
<211> LENGTH: 21
<212> TYPE: DNA
<213> ORGANISM: HUMAN

<400> SEQUENCE: 23
ttgagctcgt ggacaggctt a                                        21

<210> SEQ ID NO 24
<211> LENGTH: 18
<212> TYPE: DNA
<213> ORGANISM: HUMAN

<400> SEQUENCE: 24
gcccgttgaa aacctccc                                            18

<210> SEQ ID NO 25
<211> LENGTH: 19
```

-continued

<212> TYPE: DNA
<213> ORGANISM: HUMAN

<400> SEQUENCE: 25
caggcttccc agctccatc                                                    19

<210> SEQ ID NO 26
<211> LENGTH: 21
<212> TYPE: DNA
<213> ORGANISM: HUMAN

<400> SEQUENCE: 26
cgttaggctg gtcaccttct g                                                 21

<210> SEQ ID NO 27
<211> LENGTH: 25
<212> TYPE: DNA
<213> ORGANISM: HUMAN

<400> SEQUENCE: 27
acccaactgg tagggcttca tgcca                                             25

<210> SEQ ID NO 28
<211> LENGTH: 30
<212> TYPE: DNA
<213> ORGANISM: HUMAN

<400> SEQUENCE: 28
ttctgtggaa ttagtgaccc agcaaatgtg                                        30

<210> SEQ ID NO 29
<211> LENGTH: 31
<212> TYPE: DNA
<213> ORGANISM: HUMAN

<400> SEQUENCE: 29
agccgggatc taccataccc attgactaac t                                      31

<210> SEQ ID NO 30
<211> LENGTH: 27
<212> TYPE: DNA
<213> ORGANISM: HUMAN

<400> SEQUENCE: 30
aatgaggcgg tggtcaatat cctgtcg                                           27

<210> SEQ ID NO 31
<211> LENGTH: 27
<212> TYPE: DNA
<213> ORGANISM: HUMAN

<400> SEQUENCE: 31
aagagaaagc agtgcaaacc ttcccgt                                           27

<210> SEQ ID NO 32
<211> LENGTH: 22
<212> TYPE: DNA
<213> ORGANISM: HUMAN

<400> SEQUENCE: 32
tggcatctgc acggcggtag ag                                                22

<210> SEQ ID NO 33

```
<211> LENGTH: 27
<212> TYPE: DNA
<213> ORGANISM: HUMAN

<400> SEQUENCE: 33
cccattcagg atcacacagg agatggc                                27

<210> SEQ ID NO 34
<211> LENGTH: 22
<212> TYPE: DNA
<213> ORGANISM: HUMAN

<400> SEQUENCE: 34
ctctggctcc gtgttccgag gc                                     22

<210> SEQ ID NO 35
<211> LENGTH: 20
<212> TYPE: DNA
<213> ORGANISM: HUMAN

<400> SEQUENCE: 35
acgcggccag tgcaaggcat                                        20

<210> SEQ ID NO 36
<211> LENGTH: 32
<212> TYPE: DNA
<213> ORGANISM: HUMAN

<400> SEQUENCE: 36
agagctaaag tccaagagag gatccgagaa cg                          32

<210> SEQ ID NO 37
<211> LENGTH: 23
<212> TYPE: DNA
<213> ORGANISM: HUMAN

<400> SEQUENCE: 37
caccgtcagt gccgtgttcc agg                                    23

<210> SEQ ID NO 38
<211> LENGTH: 24
<212> TYPE: DNA
<213> ORGANISM: HUMAN

<400> SEQUENCE: 38
agagtcggtc ggaggctctg gctg                                   24

<210> SEQ ID NO 39
<211> LENGTH: 27
<212> TYPE: DNA
<213> ORGANISM: HUMAN

<400> SEQUENCE: 39
tgctaacagt cttgcaggtc tcccgag                                27
```

URINE MARKERS FOR DETECTION OF BLADDER CANCER

CLAIM OF PRIORITY

This application is a 371 National Phase Application of PCT international Patent Application No. PCT/US05/26055, filed Jul. 22, 2005, which claims priority to New Zealand Provisional Patent Application No: 534,289 filed Jul. 23, 2004 titled "Markers for Detection of Bladder Cancer," Applicant: Pacific Edge Biotechnology Ltd., to New Zealand Provisional Patent Application No: 539,219 filed Apr. 4, 2005 titled "Markers for Detection of Bladder Cancer," Applicant: Pacific Edge Biotechnology Ltd., and to and U.S. Provisional Patent Application No. 60/692,619 filed Jun. 20, 2005 titled "Urine Markers for Detection of Bladder Cancer," Inventors: Parry John Guilford, Natalie Jane Kerr and Robert Pollock. Each of the above applications is incorporated herein fully by reference.

FIELD OF THE INVENTION

This invention relates to detection of cancer. Specifically, this invention relates to the use of markers for the detection of bladder cancer. More specifically, this invention relates to use of urine markers for the detection of bladder cancer. Yet more specifically, this invention relates to use of oligonucleotide, protein, and/or antibody markers in the urine for detection, typing and staging of bladder cancer.

BACKGROUND

Introduction

Survival of cancer patients is greatly enhanced when the cancer is treated early. In the case of bladder cancer, patients diagnosed with early stage disease have 5-year survival rates of >90%, compared to approximately 15-30% for patients diagnosed with advanced disease. Therefore, developments that lead to early diagnosis of bladder cancer can lead to an improved prognosis for the patients. The established method for detecting bladder cancer using urine samples is cytology. However, cytology is known to be only about 75% sensitive for detecting invasive bladder cancer and only about 25% sensitive for detecting superficial bladder cancer (Lotan and Roehrbom, Urology 61, 109-118 (2003)).

Bladder cancer is broadly divided into two classes, invasive and superficial. The invasive type penetrates into the underlying tissue layers, while the superficial type tends to develop primarily as a polyp-like growth into the bladder lumen.

Identification of specific markers for cancer in urine can provide a valuable approach for the early diagnosis of cancer, leading to early treatment and improved prognosis. Specific cancer markers also provide a means for monitoring disease progression, enabling the efficacy of surgical, radiotherapeutic and chemotherapeutic treatments to be monitored. However, for a number of major cancers, the available markers suffer from insufficient sensitivity and specificity.

At present, the most reliable method for detecting bladder cancer is cystoscopy accompanied by histology of biopsied lesions. However, this technique is time consuming, invasive and its sensitivity is only approximately 90%, meaning that about 10 percent of cancers are not detected using these methods. Of the non-invasive methodologies, urine cytology, which detects exfoliated malignant cells microscopically, is the current preferred method. Although cytology has a specificity of about 95%, it has poor sensitivity (9-25%) for low-grade lesions, is extremely dependent on sample quality and suffers from high inter-observer variability.

More recently, attempts have been made to detect genetic markers in biopsies from the bladder. The most commonly used method is microarray analysis, in which an array containing oligonucleotides complementary to portions of a putative genetic marker is exposed to a sample of mRNA or cDNA obtained from a patient sample. Using these methods, several recent reports have identified a number of putative markers for bladder cancer. However, array technology is relatively non-quantitative and is highly variable.

The detection of blood or urine markers that indicate the presence of bladder cancer provides one potential method for the improved detection of this disease. Although little progress has been made developing blood markers for bladder cancer, several urine protein markers are available. Tests for these markers offer better sensitivity than cytology, but tend to suffer from sub-optimal specificity because elevated levels of these markers are also commonly observed in patients with non-malignant diseases including inflammation, urolithiasis and benign prostatic hyperplasia. For example, NMP22, which detects a specific nuclear matrix protein, has a sensitivity of 47-87% and a specificity of 58-91%. The high variability of NMP22 means that it is not ideal for rapid, easy detection of bladder cancer.

Other urine tests include RT-PCR amplification of gene transcripts, such as the telomerase enzyme hTERT from the cellular pellet of urine samples. RT-PCR tests offer the potential of high sensitivity, although the specificity of existing RT-PCR markers remains unclear.

There is a need for further tools for the early detection and diagnosis of cancer. This invention provides further methods, compositions, kits and devices based on cancer markers, specifically bladder cancer markers, to aid in the early detection and diagnosis of cancer.

SUMMARY OF THE INVENTION

Using a combination of microarray analysis and quantitative polymerase chain reaction (qPCR), we have been able to identify specific genetic markers that are selective for bladder cancer. In some embodiments, we have found markers that can be used to differentiate the stage of a bladder tumor, and in other embodiments, we have identified markers that can distinguish types of tumors. In other embodiments, we have unexpectedly found that combinations of two or more markers can provide for a highly reliable and sensitive detection of bladder cancer. In still further embodiments, we have identified markers that are highly expressed in bladder cancer cells and not in blood cells. Thus, in many embodiments, tests for bladder cancer are unexpectedly better than prior art tests.

In certain embodiments, microarray analysis is used to identify genes that are highly expressed in bladder tumor tissue compared to non-malignant bladder tissue. These genes, and the proteins encoded by those genes, are herein termed bladder tumor markers (BTM). It is to be understood that the term BTM does not require that the marker be specific only for bladder tumors. Rather, expression of BTM can be increased in other types of tumors, including malignant tumors. It is also to be understood that BTM includes markers that are not highly expressed in blood cells. By virtue of sampling from the urine, expression of other types of cells commonly present in prior art biopsy samples are not present. The term BTM also includes combinations of individual markers that are useful for detection of bladder cancer.

In other embodiments, methods are provided to identify the presence of markers in samples including immunohistochemistry and quantitative polymerase chain reaction (qPCR). qPCR methods are less prone to artifacts that are common in microarray methods. Such artifacts include differences in the number of ligand oligonucleotides placed on an array dot, uneven and unpredictable binding of dyes to hybridized oligonucleotides on an array spot, uneven washing of non-specific materials from array spots and other problems.

Certain of the genes disclosed herein encode proteins that are secreted by, cleaved from the cell or released from a cell upon cell death. These mRNA transcripts and their proteins have the added utility as markers for the diagnosis of bladder cancer or as markers for monitoring the progression of established disease. These markers can be used either alone or in combination with each other. In addition, other genes, RNA transcripts and the encoded proteins remain within or associated with the cell and can be used either alone or in combination with each other as urine markers.

Strategies for treating superficial and invasive bladder cancer may be different. Invasive bladder cancer requires surgical resection more urgently and allows fewer treatment alternatives than does the superficial type of bladder cancer. In contrast, superficial bladder cancer can be successfully treated with either intravesicular chemotherapy or intravesicular BCG immunotherapy.

At present, however, there are no methods to easily and reliably distinguish between superficial and invasive bladder cancer classes without performing cystoscopy. The ability to distinguish between these classes using a non-invasive method such as a urine test, would allow clinicians to select appropriate treatment strategies without relying on cystoscopy, which is expensive, inconvenient and often poorly accepted by patients.

We have unexpectedly found that certain urine markers, in particular those not found in blood at high levels, when used in combination or alone can provide highly reliable, sensitive and specific diagnosis of bladder cancer.

BRIEF DESCRIPTION OF THE FIGURES

This invention is described with reference to specific embodiments thereof and with reference to the Figures, in which:

FIG. 1 depicts a table depicting the number and origin of samples used in qPCR analysis.

FIG. 2 depicts a table of markers and oligonucleotide probes of markers for qPCR analysis of bladder cancer of this invention.

Figure 3:
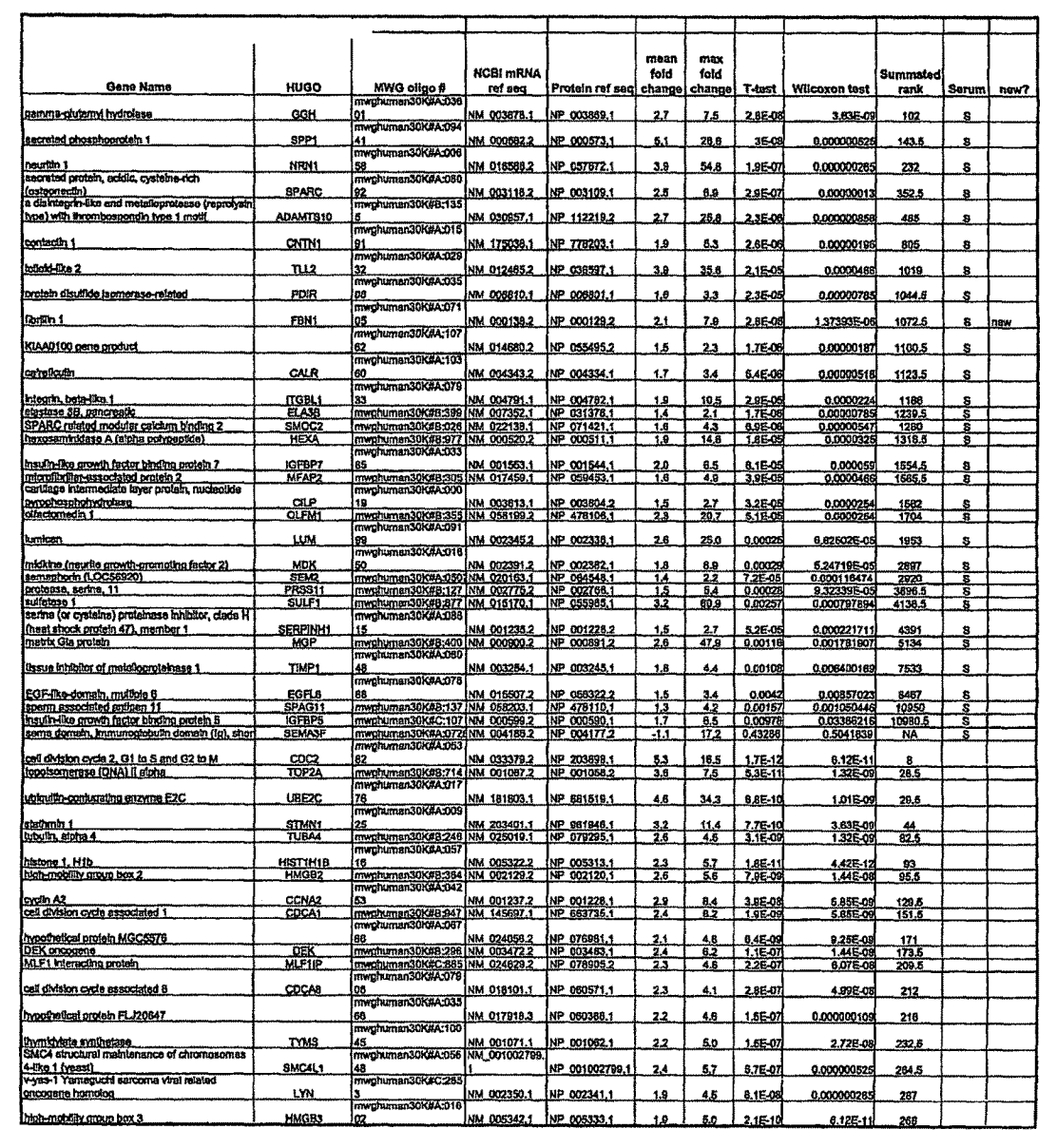
Figure 3:
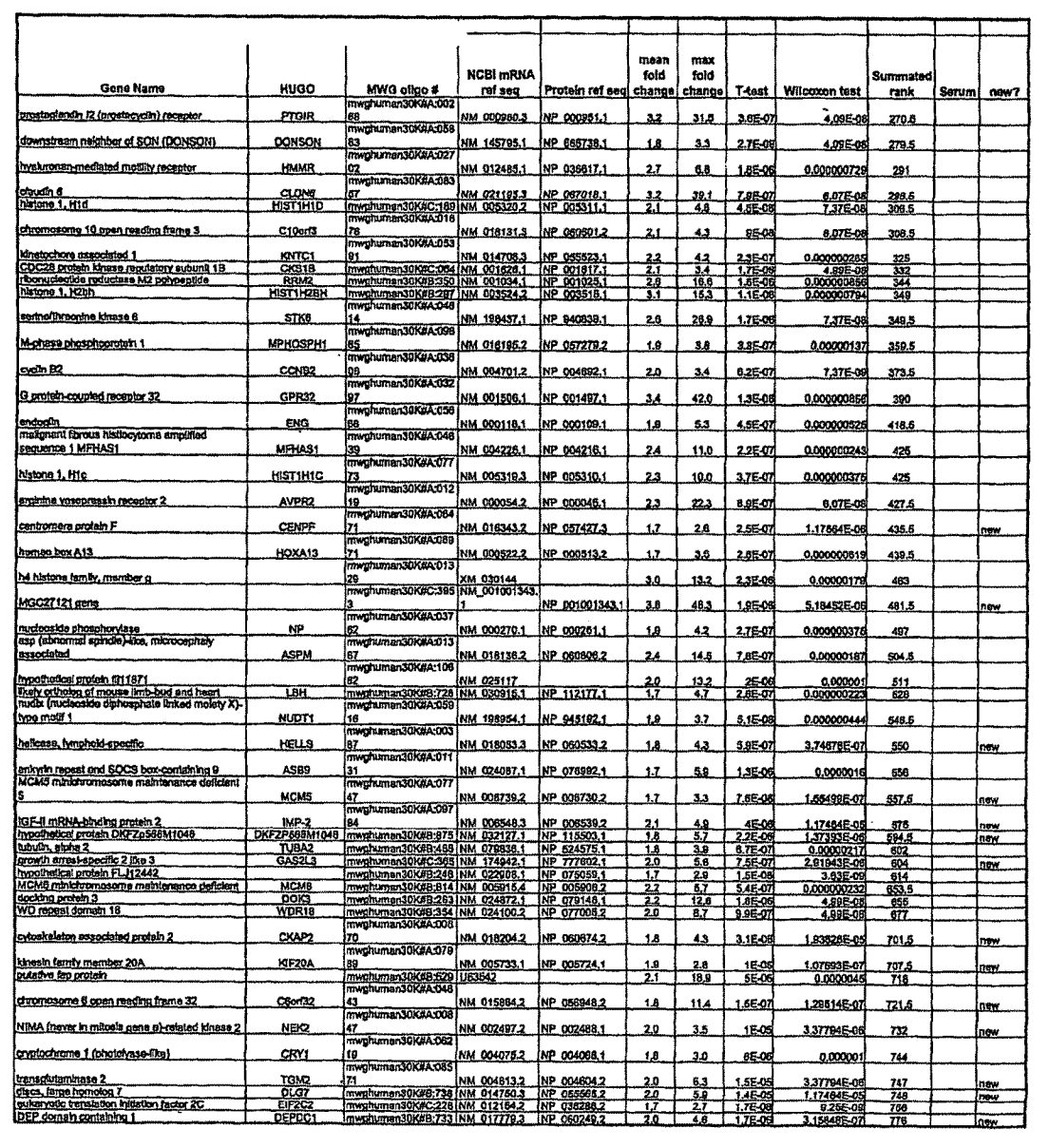
Figure 3:
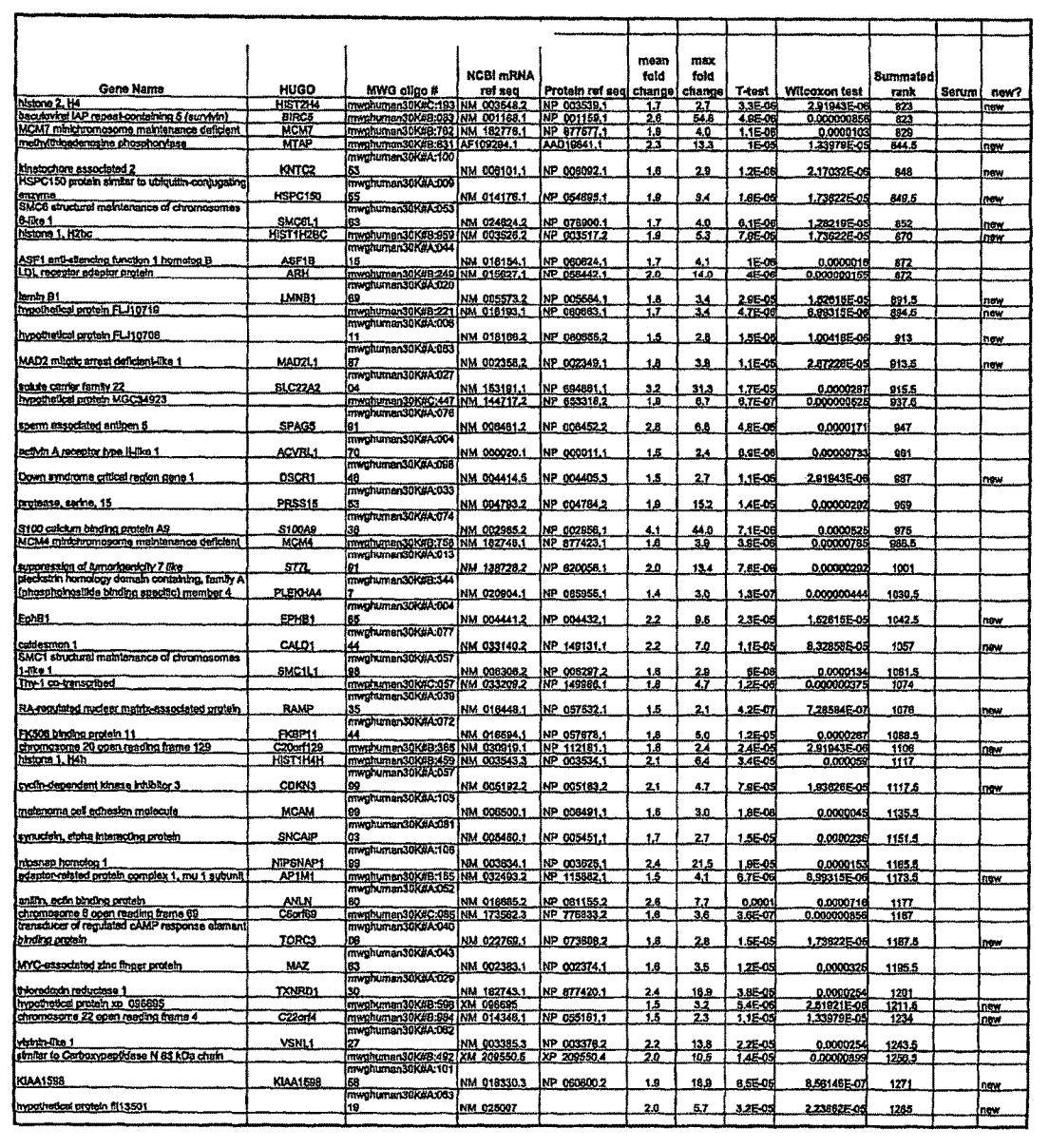
Figure 3:
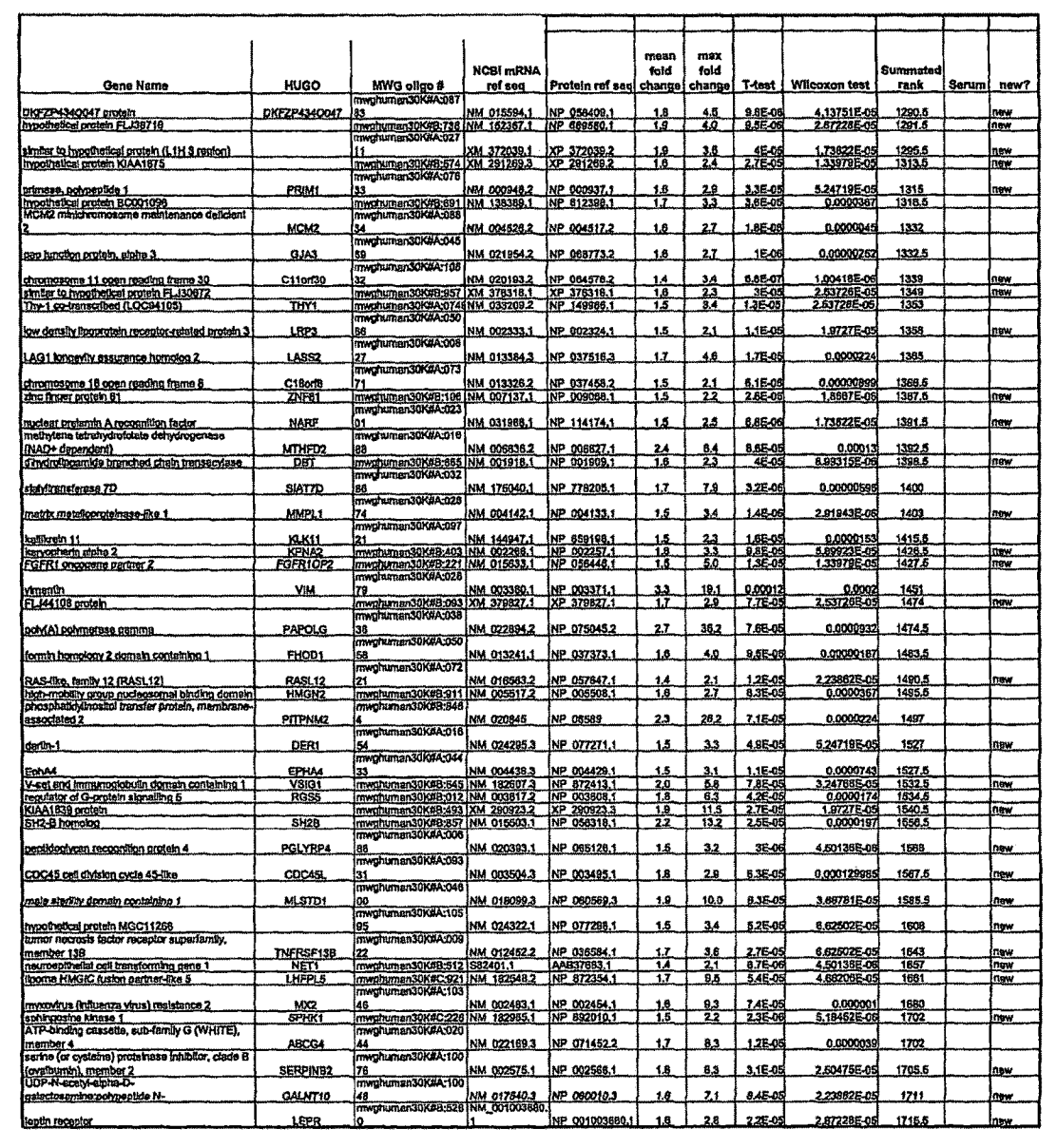

FIG. 3 depicts a table of BTMs identified using microarray methods on samples of invasive bladder cancer.

FIG. 4 depicts a table of BTMs identified using microarray methods on samples of superficial bladder cancer.

FIG. 5 depicts a table of results obtained in studies carried out using quantitative PCR analysis for specific BTMs.

FIG. 6a: SPAG5, invasive.

FIG. 6aa: MDK, invasive; FIG. 6ab: MDK, superficial; FIG. 6ac: Thy1, invasive; Figure bad, Thy1, superficial; FIG. 6ae: SMC4L1, invasive; 6af: SMC4L1, superficial.

FIG. 7 depicts a table of results obtained of studies carried out using quantitative PCR analysis for specific BTMs using urine samples.

FIG. 10 depicts median over-accumulation of marker transcripts in the urine of bladder cancer patients. The log2 difference between patients and healthy controls and patients and non-malignant controls are shown separately.

FIGS. 13a-13b depict tables that show the effect of multiple markers on the ability to accurately discriminate between tumor tissue and non-malignant tissue. The table has been constructed from normal distributions derived from qPCR data. FIG. 13a depicts the effect of multiple markers on the ability to accurately discriminate between invasive bladder cancer tissue and non-malignant tissue at a specificity of 95%. FIG. 13b depicts the effect of multiple markers on the ability to accurately discriminate between superficial bladder cancer tissue and non-malignant tissue at a specificity of 95%.

FIGS. 14a-14b depict tables showing the sensitivity of marker combinations for invasive transitional cell carcinoma (TCC) at 95% specificity, calculated from the normal distributions of the qPCR data. FIG. 14a: invasive transitional cell carcinoma (TCC). FIG. 14b: superficial TCC.

FIG. 15 depicts a table that shows the effect of multiple markers on the ability to accurately discriminate between urine samples obtained from bladder cancer (TCC) patients and urine samples from patients with non-malignant urological diseases. The table has been constructed from the normal distribution of data obtained from the urine qPCR analysis.

FIG. 16 depicts a table showing the sensitivity of marker combinations in urine for the detection of TCC at a specificity of 95%, calculated from the normal distribution of the urine qPCR data. FIG. 16A depicts results for singler marker, two marker, and some three marker combinations. FIG. 16 Depicts additional three marker combinations. FIG. 16C depicts additional three marker combinations.

DETAILED DESCRIPTION

Definitions

Figure 6A:
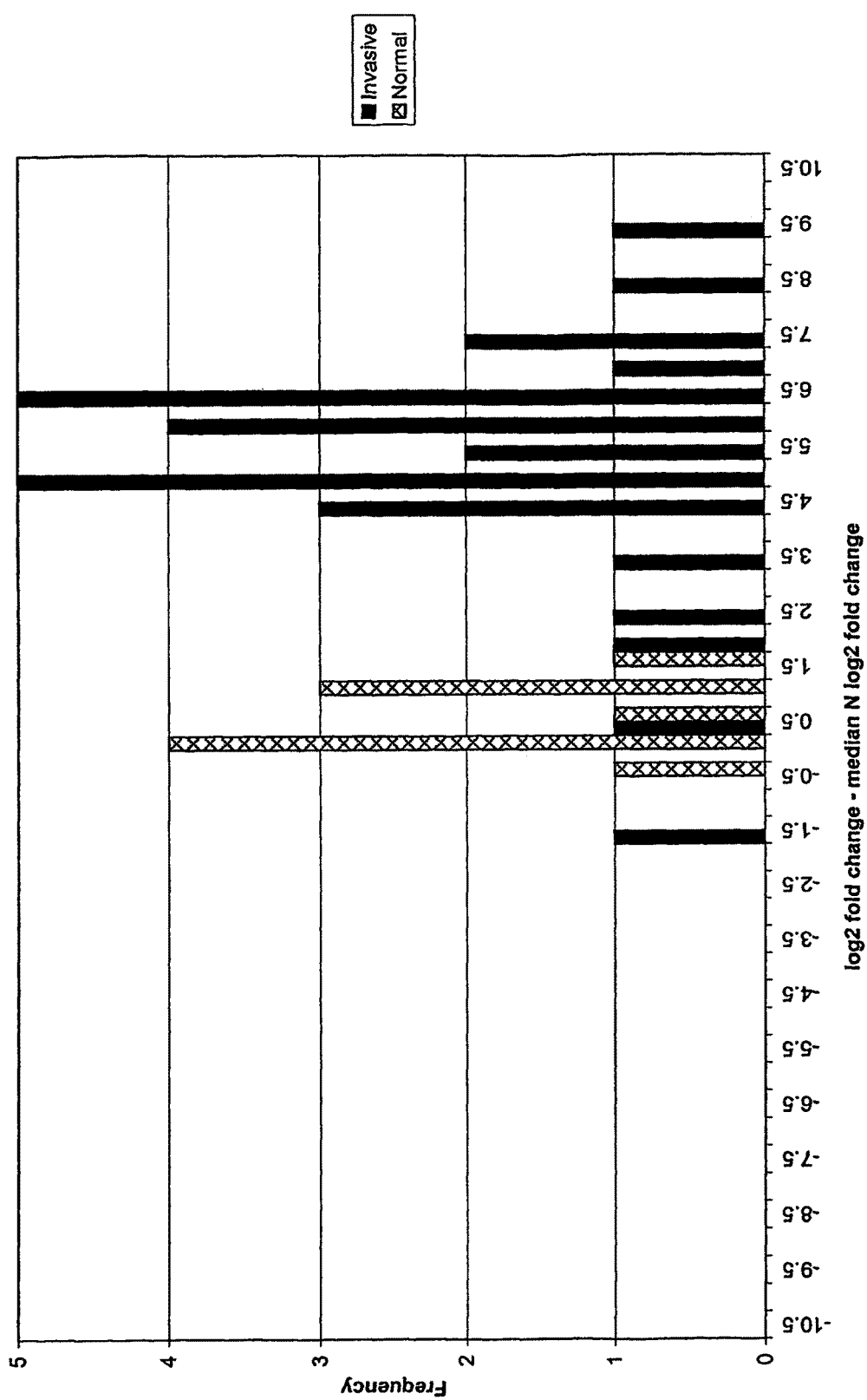
FIGS. 6a-6af depict histograms showing the relative frequency vs. log2 fold change data obtained from quantitative PCR studies of various tumor markers of invasive and superficial bladder tumors.
Figure 6B:
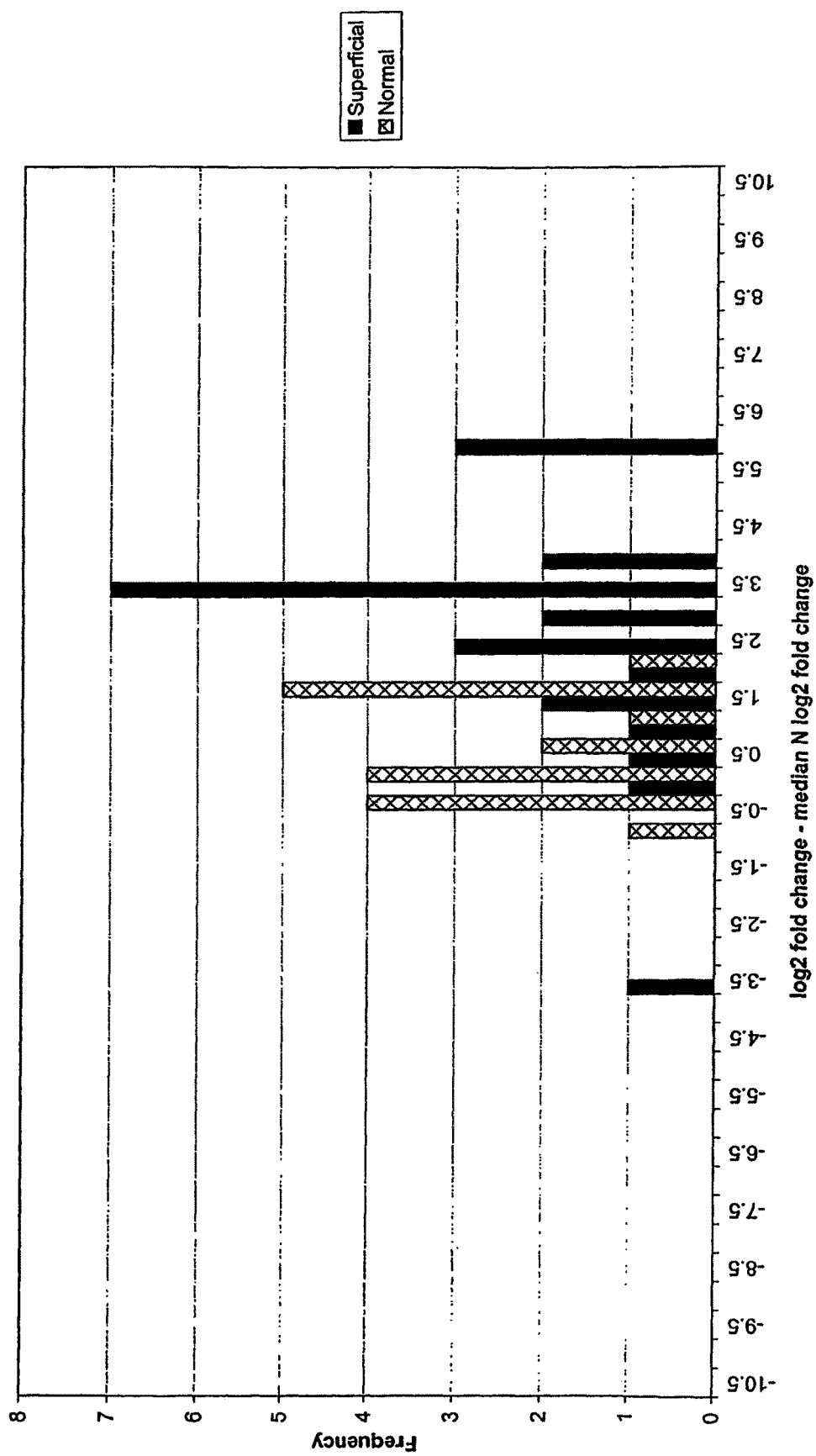
FIG. 6b: SPAG5, superficial.

Before describing embodiments of the invention in detail, it will be useful to provide some definitions of terms as used herein.

The term "marker" means a molecule that is associated quantitatively or qualitatively with the presence of a biological phenomenon. Examples of "markers" include a gene, gene fragment, RNA, RNA fragment, protein or protein fragment, related metabolites, by products or other identifying molecules, whether related directly or indirectly to a mechanism underlying the phenomenon.

The term "sensitivity" means the proportion of individuals with the disease who test positive. Thus, increased sensitivity means fewer false negative test results.

The term "specificity" means the proportion of individuals without the disease who test negative. Thus, increased specificity means fewer false positive test results.

The term "BTM" or "bladder tumor marker" or "BTM family member" means a marker that is associated with bladder cancer. The term BTM also includes combinations of individual markers, whose combination improves the sensitivity and specificity of detecting bladder cancer. In some sections of this application, the term BTM may include UBTM (defined herein) for convenience. Non-limiting examples of BTMs are included in FIGS. 3 and 4 herein.

A BTM can be identified by extracting RNA from a tissue sample from a patient suspected of having bladder cancer, applying the RNA to a microarray having a number of oligonucleotides thereon, permitting the sample RNA to hybridize to the oligonucleotides on the array, and then quantifying the level of measured RNA bound to the each array spot. A marker is considered to be a BTM if its presence is above a threshold of at least about 1.2 times that found in normal, non-malignant tissue using microarray methods. Alternatively, the threshold can be above about 2 times normal, about 3 times more than normal, 4 times or even about 5 times more than normal. By "normal" we mean more than the 90$^{th}$ percentile of the normal population. In other cases, normal can mean a level of presence of the 95$^{th}$ percentile (i.e., about 2 Standard Deviations (SD) from the mean), and in other cases, greater than about 97.5$^{th}$ percentile (i.e., about 3 SD) or the 99$^{th}$ percentile.

In still further cases, a BTM can be selected that is present in tumor tissue but is not present in the blood to a substantial extent. By "substantial extent" we mean that the amount in tumor tissue is at least about 5 cycles more as measured by qPCR than the amount found in blood.

The Term "UBTM" or "urinary bladder tumor marker" or "UBTM family member" means a BTM marker found in the urine that is associated with bladder cancer but does not include TOP2A, MDK or BIRC5. The term UBTM also includes combinations of two markers and combinations of three markers, whose combination improves the sensitivity and selectivity of detecting bladder cancer in urine samples. Non-limiting examples of UBTMs are included in FIGS. 14a and 14b herein.

In other cases, a UBTM can be identified in urine using microarray methods or using qPCR methods using a forward primer, a reverse primer and a probe selected based upon the marker to be evaluated. The threshold for detection of bladder cancer in urine can be greater than the level of the marker in urine of normal subjects having bladder cancer by about 1 cycle (2-fold), 2 cycles (4-fold), 3 cycles (8-fold), 4 cycles (16-fold), 5 cycles (32-fold) or more.

The term "qPCR" means quantitative polymerase chain reaction.

The term "expression" includes production of mRNA from a gene or portion of a gene, and includes the production of a protein encoded by an RNA or gene or portion of a gene, and includes appearance of a detectable material associated with expression. For example, the binding of a binding ligand, such as an antibody, to a gene or other oligonucleotide, a protein or a protein fragment and the visualization of the binding ligand is included within the scope of the term "expression." Thus, increased density of a spot on an immunoblot, such as a Western blot, is included within the term "expression" of the underlying biological molecule.

The term "rate of expression" means a time-dependent change in the amount of a transcript or protein.

The term "over expression" is used where the rate of expression of a marker in one cell, or cell type, is greater than that of another cell, or cell type per a defined time period.

The term "accumulation" means an increased amount of a marker in a sample compared to a normal mean value. By "increased amount" we mean the amount of marker is higher than the $90^{th}$, $95^{th}$, $97.5^{th}$ $99^{th}$ or greater percentile of the normal range by at least about 1.2 fold, 2-fold, 3-fold, 4-fold, or 5-fold when measured using microarray methods. When measured using qPCR, "increased amount" means the amount of marker that is higher than the $90^{th}$, $95^{th}$, $97.5^{th}$ or $99^{th}$ percentile of the normal range by at least about 1 cycle (2-fold), 2 cycles (4-fold), 3 cycles (8-fold), 4 cycles (16-fold), 5 cycles (32-fold) or more.

Accumulation includes an increased amount of marker in a cell (on a per cell basis) or can mean an increased number of cells in a sample that have the particular marker. Thus, accumulation can mean an increased total amount of a marker in the urine (on a per volume basis) compared to a condition not characterized by bladder cancer. Accumulation can also reflect an increase in the rate of expression of a BTM in a given cell type, and/or increase in the number of cells expressing a BTM at a normal rate of expression. Moreover, accumulation can also reflect free mRNA present due to loss of cell membrane integrity or cell death and destruction.

DESCRIPTION OF EMBODIMENTS OF THE INVENTION

Markers for detection and evaluation of tumors including bladder are provided. It has been found that numerous genes and proteins are associated with bladder tumors. Microarray analysis of samples taken from patients with bladder tumors and from non-malignant samples of normal urothelium has led to the surprising discovery that in many bladder tumors, specific patterns of over-expression of certain genes or accumulation of gene products in the urine are associated with the disease. Most surprisingly, markers have been isolated that are present at high levels in urine samples from patients with bladder cancer but are present in low levels in healthy individuals and, in particular, in individuals with non-malignant urological diseases, including those exhibiting hematuria. Detection of markers, for example the gene products (e.g. oligonucleotides such as mRNA) and proteins and peptides translated from the oligonucleotides, therefore are indicative of the presence of a tumor, especially a bladder tumor.

It can be appreciated that the level of a particular marker or set of markers can depend upon the amount of urine produced compared to the amount of the marker present. Thus, in conditions characterized by reduced urine production (e.g., reduced urine volume), the concentration of a marker may be increased, yet may not reflect bladder cancer. Therefore, in some embodiments, the amount of a marker can be corrected for by total urine production over a given time. Alternatively, marker concentration can be corrected for by total cell number in the urine sample, and in other embodiments may be corrected for by total protein present in the urine. On the other hand, increased urine production may dilute a tumor marker, and thereby tend to mask the presence of bladder cancer. Such conditions can be associated with increased water intake, decreased salt intake, increased use of diuretics or suppression of antidiuretic hormone production or activity.

In some embodiments, one can measure renal function using methods known in the art. These include, by way of example, measurement of creatinine clearance. However, it can be appreciated that there are many suitable methods for measuring renal function. In conditions in which abnormal renal function is found, one can adjust the measured accumulation of a marker using appropriate corrections. Therefore, bladder cancer can be more accurately diagnosed.

Cancer markers can be detected in a sample using any suitable technique, and can include, but is not limited to, oligonucleotide probes, qPCR or antibodies raised against cancer markers.

It will be appreciated that the sample to be tested is not restricted to a sample of the tissue suspected of being a tumor. The marker may be secreted into the serum, sloughed from cell membranes or associated with cells lost into the urine. Therefore, a sample can include any bodily sample, and includes blood, serum, peritoneal washes, cerebrospinal fluid, urine and stool samples.

The detection of one cancer marker in a sample will be indicative of the presence of a tumor in that subject. However, it will be appreciated that by analyzing the presence and amounts of expression of a plurality of cancer markers, the sensitivity of diagnosis will be increased while decreasing the frequency of false positive and/or false negative results. Therefore, multiple markers according to the present invention can be used to increase the early detection and diagnosis of cancer.

General Approaches to Cancer Detection

The following approaches are non-limiting methods that can be used to detect cancer, including bladder cancer, using BTM or UBTM family members.

Hybridization Methods Using Nucleic Acid Probes Selective for a Marker

These methods involve binding the nucleic acid probe to a support, and hybridizing under appropriate conditions with RNA or cDNA derived from the test sample (Sambrook, J., E Fritsch, E. and T Maniatis, Molecular Cloning: A Laboratory Manual $3^{rd}$. Cold Spring Harbor Laboratory Press: Cold Spring Harbor (2001)). These methods can be applied to BTM or UBTM as appropriate derived from a tumor tissue or fluid sample. The RNA or cDNA preparations are typically labeled with a fluorescent or radioactive molecule to enable detection and quantification. In some applications, the hybridizing DNA can be tagged with a branched, fluorescently labeled structure to enhance signal intensity (Nolte, F. S., Branched DNA signal amplification for direct quantitation of nucleic acid sequences in clinical specimens. Adv. Clin. Chem. 33, 201-35 (1998)). Unhybridized label is removed by extensive washing in low salt solutions such as 0.1×SSC, 0.5% SDS before quantifying the amount of hybridization by fluorescence detection or densitometry of gel images. The supports can be solid, such as nylon or nitrocellulose membranes, or consist of microspheres or beads that are hybridized when in liquid suspension. To allow washing and purification, the beads may be magnetic (Haukanes, B-I and Kvam, C, Application of magnetic beads in bioassays. Bio/Technology 11, 60-63 (1993)) or fluorescently-labeled to enable flow cytometry (see for example: Spiro, A., Lowe, M. and Brown, D., A Bead-Based Method for Multiplexed Identification and Quantitation of DNA Sequences Using Flow Cytometry. Appl. Env. Micro. 66, 4258-4265 (2000)).

A variation of hybridization technology is the QuantiGene Plex® assay (Genospectra, Fremont) which combines a fluorescent bead support with branched DNA signal amplification. Still another variation on hybridization technology is the Quantikine® mRNA assay (R&D Systems, Minneapolis). Methodology is as described in the manufacturer's instructions. Briefly the assay uses oligonucleotide hybridization probes conjugated to Digoxigenin. Hybridization is detected using anti-Digoxigenin antibodies coupled to alkaline phosphatase in colorometric assays.

Additional methods are well known in the art and need not be described further herein.

Quantitative PCR (qPCR)

Quantitative PCR (qPCR) can be carried out on tumor samples, on serum, plasma and urine samples using BTM specific primers and probes. In controlled reactions, the amount of product formed in a PCR reaction (Sambrook, J., E Fritsch, E. and T Maniatis, Molecular Cloning: A Laboratory Manual $3^{rd}$. Cold Spring Harbor Laboratory Press: Cold Spring Harbor (2001)) correlates with the amount of starting template. Quantification of the PCR product can be carried out by stopping the PCR reaction when it is in log phase, before reagents become limiting. The PCR products are then electrophoresed in agarose or polyacrylamide gels, stained with ethidium bromide or a comparable DNA stain, and the intensity of staining measured by densitometry. Alternatively, the progression of a PCR reaction can be measured using PCR machines such as the Applied Biosystems' Prism 7000 or the Roche LightCycler which measure product accumulation in real-time. Real-time PCR measures either the fluorescence of DNA intercalating dyes such as Sybr Green into the synthesized PCR product, or the fluorescence released by a reporter molecule when cleaved from a quencher molecule; the reporter and quencher molecules are incorporated into an oligonucleotide probe which hybridizes to the target DNA molecule following DNA strand extension from the primer oligonucleotides. The oligonucleotide probe is displaced and degraded by the enzymatic action of the Taq polymerase in the next PCR cycle, releasing the reporter from the quencher molecule.

In some embodiments, a forward primer, reverse primer and probe set includes SEQ ID NO:1, SEQ ID NO:14, and SEQ ID NO:27 respectively. Alternatively sets include SEQ ID NO:2, SEQ ID NO:15 and SEQ ID NO:28, respectively. In other embodiments, sets include SEQ ID NO:3, SEQ ID NO:16, and SEQ ID NO:29 respectively, SEQ ID NO:4, SEQ ID NO:17, and SEQ ID NO:30 respectively, SEQ ID NO:5, SEQ ID NO:18, and SEQ ID NO:31 respectively, SEQ ID NO:6, SEQ ID NO:19, and SEQ ID NO:32 respectively, SEQ ID NO:7, SEQ ID NO:20, and SEQ ID NO:33 respectively, SEQ ID NO:8, SEQ ED NO:21, and SEQ ID NO:34 respectively, SEQ ID NO:9, SEQ ID NO:22, and SEQ ID NO:35 respectively, SEQ ID NO:10, SEQ ID NO:23, and SEQ ID NO:36 respectively, SEQ ID NO:11, SEQ ID NO:24, and SEQ ID NO:37 respectively, SEQ ID NO:12, SEQ ID NO:25, and SEQ ID NO:38 respectively and SEQ ID NO:13, SEQ ID NO:26, and SEQ ID NO:39 respectively.

Enzyme-Linked Immunological Assays (ELISA)

Briefly, in sandwich ELISA assays, a polyclonal or monoclonal antibody against the BTM/UBTM is bound to a solid support (Crowther, J. R. The ELISA guidebook. Humana Press: New Jersey (2000); Harlow, E. and Lane, D., Using antibodies: a laboratory manual. Cold Spring Harbor Laboratory Press: Cold Spring Harbor (1999)) or suspension beads. Other methods are known in the art and need not be described herein further. Monoclonal antibodies can be hybridoma-derived or selected from phage antibody libraries (Hust M. and Dubel S., Phage display vectors for the in vitro generation of human antibody fragments. Methods Mol Biol. 295:71-96 (2005)). Non-specific binding sites are blocked with non-target protein preparations and detergents. The capture antibody is then incubated with a preparation of urine or tissue containing the BTM/UBTM antigen. The mixture is washed before the antibody/antigen complex is incubated with a second antibody that detects the target BTM/UBTM. The second antibody is typically conjugated to a fluorescent molecule or other reporter molecule that can either be detected in an enzymatic reaction or with a third antibody conjugated to a reporter (Crowther, Id.). Alternatively, in direct ELISAs, the preparation containing the BTM/UBTM can be bound to the support or bead and the target antigen detected directly with an antibody-reporter conjugate (Crowther, Id.).

Methods for producing monoclonal antibodies and polyclonal antisera are well known in the art and need not be described herein further.

Immunohistochemistry

Identification and localization of tumor markers can be carried out using anti-marker antibodies on bladder tumors, lymph nodes or distant metastases. Such methods can also be used to detect, for example, colorectal, pancreatic, ovarian, melanoma, liver, esophageal, stomach, endometrial, and brain.

In general, BTMs can be detected in tissues using immunohistochemistry (Harlow, E. and Lane, D., Using antibodies: a laboratory manual. Cold Spring Harbor Laboratory Press: Cold Spring Harbor (1999)). Briefly, paraffin-embedded or frozen OCT-embedded tissue samples are cut into 4-8 um sections onto glass slides, fixed and permeabilized, then incubated with a primary monoclonal or polyclonal antibody against the BTM. The primary antibody can either be conjugated to a detection molecule or reporter for direct antigen detection or, alternatively, the primary antibody can itself be detected with a second antibody conjugated to a reporter or detection molecule. Following washing and activation of any reporter molecules, the presence of the BTM can be visualized microscopically.

The methods can also be used for immunodetection of marker family members in sera or plasma from bladder cancer patients taken before and after surgery to remove the tumor, immunodetection of marker family members in patients with other cancers, including but not limited to, colorectal, pancreatic, ovarian, melanoma, liver, oesophageal, stomach, endometrial, and brain and immunodetection of marker family members in urine and stool from bladder cancer patients.

BTMs and UBTMs can also be detected in tissues or urine using other standard immunodetection techniques such as immunoblotting or immunoprecipitation (Harlow, E. and Lane, D., Using antibodies: a laboratory manual. Cold Spring Harbor Laboratory Press: Cold Spring Harbor (1999)). In immunoblotting, protein preparations from tissue or fluid containing the BTM/UBTM are electrophoresed through polyacrylamide gels under denaturing or non-denaturing conditions. The proteins are then transferred to a membrane support such as nylon. The BTM/UBTM is then reacted directly or indirectly with monoclonal or polyclonal antibodies as described for immunohistochemistry. Alternatively, in some preparations, the proteins can be spotted directly onto membranes without prior electrophoretic separation. Signal can be quantified by densitometry.

In immunoprecipitation, a soluble preparation containing the BTM or UBTM is incubated with a monoclonal or polyclonal antibody against the BTM/UBTM. The reaction is then incubated with inert beads made of agarose or polyacrylamide with covalently attached protein A or protein G. The protein A or G beads specifically interact with the antibodies forming an immobilized complex of antibody-BTM/UBTM-antigen bound to the bead. Following washing the bound BTM/UBTM can be detected and quantified by immunoblotting or ELISA.

Analysis of Array or qPCR Data Using Computers

Primary data is collected and fold change analysis is performed by comparison of levels of bladder tumor gene expression with expression of the same genes in non-tumor tissue. A threshold for concluding that expression is increased is provided (e.g., 1.5× increase, 2-fold increase, and in alternative embodiments, 3-fold increase, 4-fold increase or 5-fold increase). It can be appreciated that other thresholds for concluding that increased expression has occurred can be selected without departing from the scope of this invention. Further analysis of tumor gene expression includes matching those genes exhibiting increased expression with expression profiles of known bladder tumors to provide diagnosis of tumors.

Use of BTMs and UBTMs to Monitor the Progression of TCC Therapies

In addition to the rapid diagnosis and early detection of TCC, BTM and UBTM markers detected in either tissue, serum or urine can be used to monitor a patient's response to therapy. In these applications, urine and/or serum samples can be taken at intervals following the initiation of systemic, intravesicular or intravascular chemotherapy, radiotherapy or immunotherapy. A decline in marker accumulation can indicate a reduction in tumor size, indicative of effective treatment. The rate of decline can be used to predict the optimum therapeutic dose for each patient or treatment.

Figure 4:
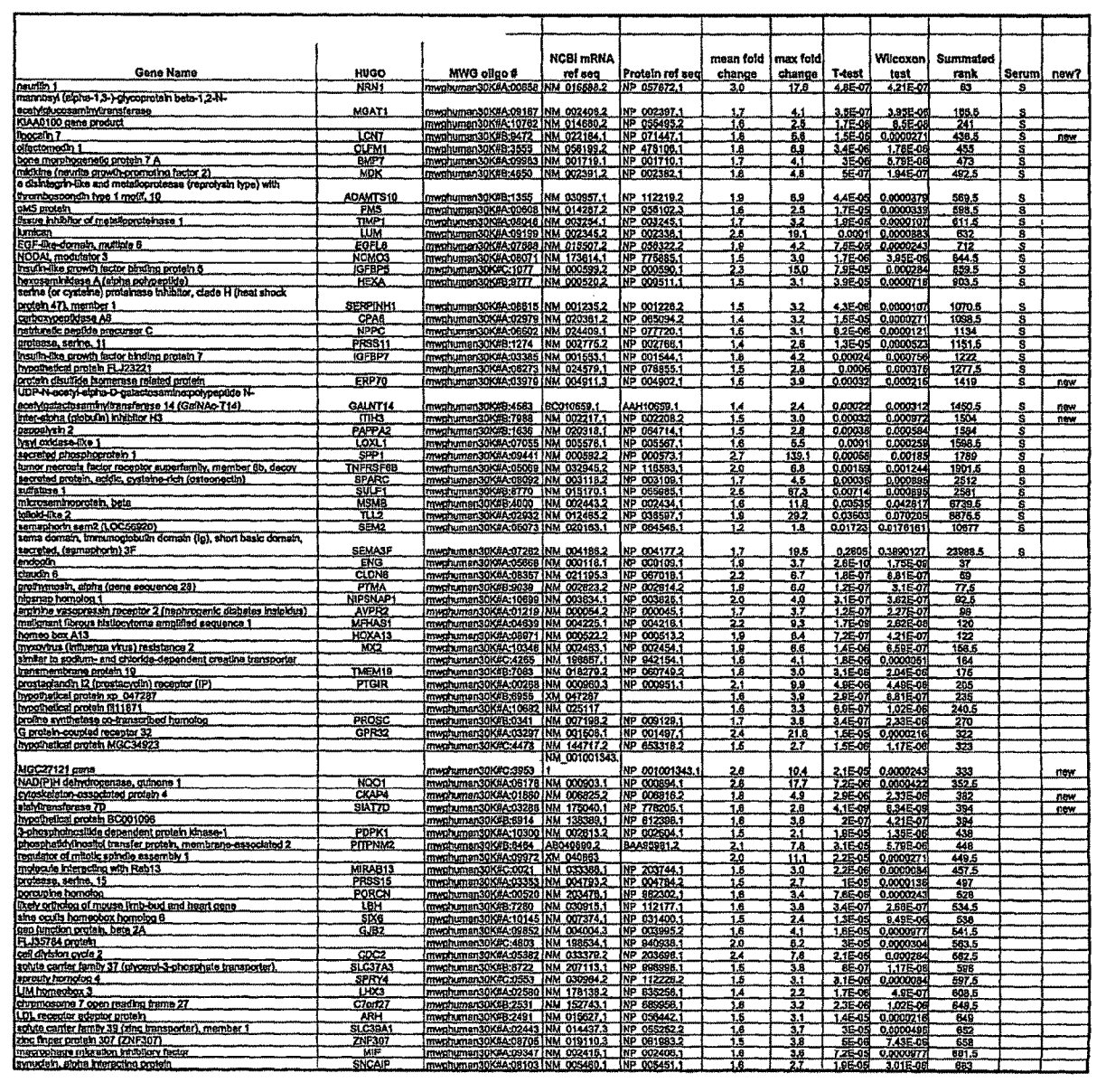
Figure 4:
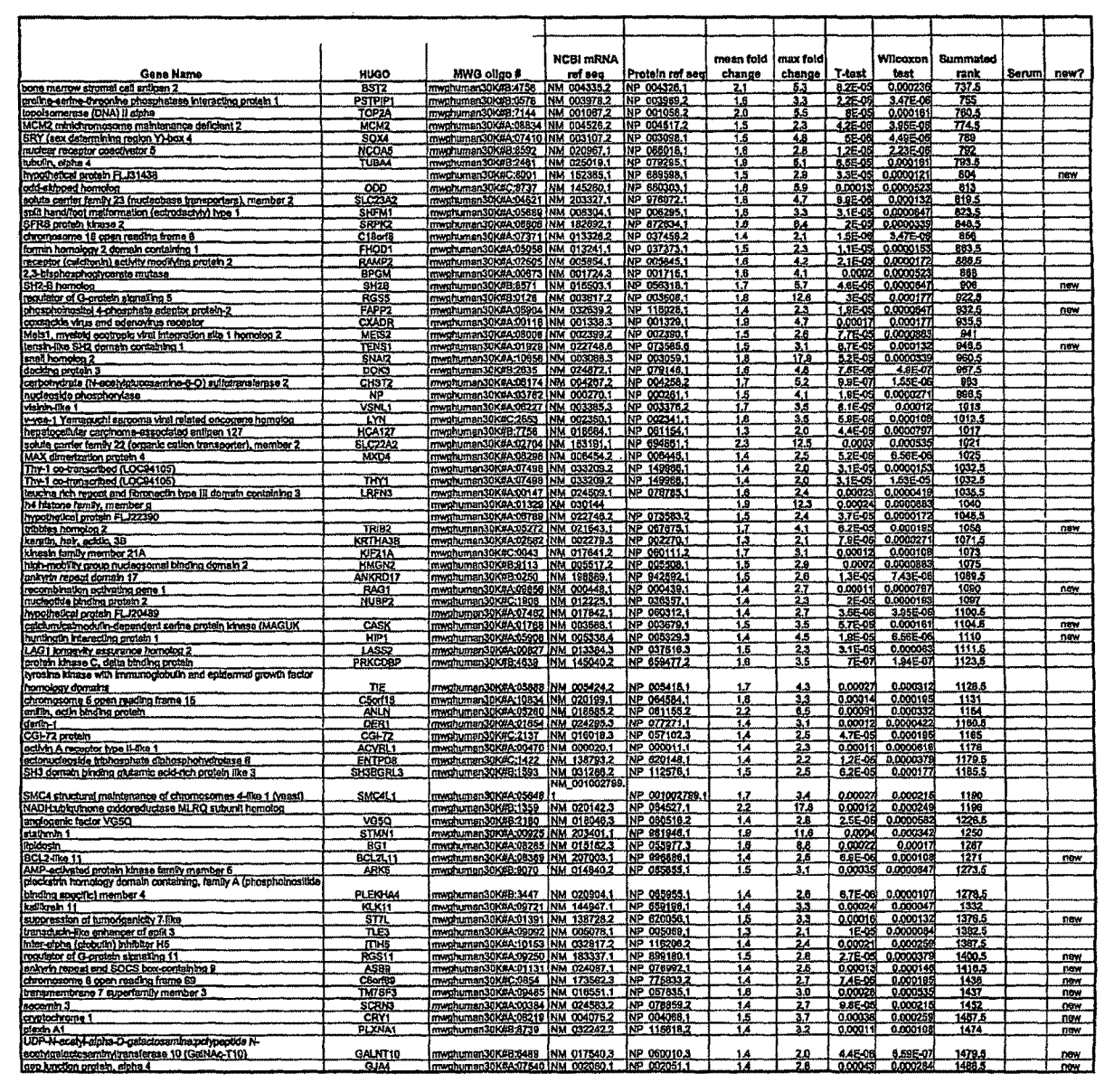

Markers evaluated are selected from known human genes. The genes evaluated are indicated in FIGS. 3 and 4. Included in FIGS. 3 and 4 are the name of the gene, the HUGO identifier, MWG oligo number, NCBI mRNA reference sequence number and the protein reference number. The full length sequences can be found at the ncbi nlm nih gov website.

The markers identified as useful for diagnosing and evaluating bladder cancer are identified in FIG. 2 and in the Sequence Listing appended to this application.

Aspects of the Invention

Thus, in certain aspects, this invention includes methods for detecting bladder cancer, comprising detecting the accumulation of a UBTM family member in the urine.

In other aspects, the UBTM family member is not associated with blood to a substantial extent.

In additional aspects, the UBTM is selected from the group shown in FIG. 3 or 4.

Additionally, in certain aspects, the step of detecting is carried out by detecting accumulation of BTM or UBTM mRNA.

In some aspects, the step of detecting is carried out using a microarray.

In other aspects, the step of detecting is carried out using quantitative polymerase chain reaction or hybridization methods.

In further aspects, the step of detecting is carried out by detecting accumulation of a UBTM protein.

In still further aspects, the step of detecting is carried out by detecting accumulation of a UBTM peptide.

In some of these aspects, the step of detecting is carried out using a UBTM antibody that may be either polyclonal or monoclonal.

In additional aspects, a method includes detection of accumulation of two or more UBTM family members in said sample.

In certain of these additional aspects, a methods involves detecting TOP2A, MDK or BIRC5.

Yet further aspects include detecting one or more pairs of markers selected from the group consisting of TOP2A-HOXA13, TOP2A-IGFBP5 and TOP2A-SEMA3F.

In other aspects of this invention, a method for detecting bladder cancer, comprises detecting the accumulation of a combination of two or more BTM family members selected from FIG. 14a or 14b in a biological sample from a patient suspected of having bladder cancer.

In some of these aspects, the biological sample is selected from the group consisting of blood, serum, plasma, tissue, urine, stool, cerebrospinal fluid and peritoneal wash.

Still further aspects include antibodies specific for a BTM or UBTM and methods for their production, either as polyclonal or as monoclonal antibodies.

In certain of these aspects a monoclonal antibody can be directed towards a BTM or UBTM is selected from the group shown in FIG. 3 or 4.

In other of these aspects, a method further comprises another antibody directed against another BTM or UBTM.

Additional aspects of this invention include devices for detecting a BTM, comprising a substrate having a combination of BTM or UBTM capture reagents thereon, the combination selected from FIG. 14a or 14b; and a detector associated with said substrate, the detector capable of detecting said combination of BTM or UBTM associated with said capture reagents.

In certain of these aspects, a capture reagent comprises an oligonucleotide.

In additional aspects, a capture reagent comprises an antibody.

In some aspects, a BTM or UBTM is selected from the group specified in FIG. 3 or 4.

This invention also includes kit for detecting cancer, comprising a substrate; a combination of at least two BTM or UBTM capture reagents thereon, the combination selected from FIG. 14a or 14b; and instructions for use.

Some kits include capture reagents that are BTM- or UBTM-specific oligonucleotides or BTM-specific antibodies.

In some kits, the BTMs or UBTMs are selected from the group depicted in FIG. 3 or 4.

In certain kits, a marker is selected from the group consisting of IGFBP5, MGP, SEMA3F and HOXA13.

Additional aspects include methods for detecting the presence of bladder cancer, comprising determining the presence in a urine sample, one or more markers selected from the group consisting of BIRC2, CDC2, HOXA13, IGFBP5, MDK, MGP, NOV, NRP1, SEMA3F, SPAG5, TOP2A, and wherein said marker is not substantially present in blood.

Other aspects of this invention include methods for distinguishing malignant bladder disease from non-malignant bladder disease, comprising determining the accumulation in said patient's urine of one or more marker selected from the group consisting of HOXA13, IGFBP5, MDK, MGP, NRP1, SEMA3F, SMC4L1, TOP2A and UBE2C; and determining the ratios of said markers in said sample, the ratio being associated with the presence of bladder cancer.

In certain of these aspects, methods comprise measuring accumulation of at least a second BTM in the urine.

In some of these embodiments, a first marker is TOP2A and a second marker is selected from the group consisting of HOXA13, IGFBP5 and SEMA3F.

In additional aspects, this invention includes correlating a ratio of accumulation of markers as indicative of superficial bladder cancer, invasive stage 1 bladder cancer or invasive stage 2-3 bladder cancer.

In yet further aspects, this invention includes methods for determining efficacy of therapy for bladder cancer, comprising comparing the presence of one or more markers selected from FIG. 3 or 4 in a first sample from a patient with the presence of one or more markers selected from FIG. 3 or 4 in a second sample from a patient after a period of treatment.

As described herein, detection of tumors can be accomplished by measuring expression of one or more tumor markers. It has unexpectedly been found that the association between increased expression of either a plurality of BTMs or UBTMs and the presence of diagnosed bladder cancer is extremely high. The least significant association detected had a p value of about 0.018. Many of the associations were significant at p values of less than $10^{-10}$. With such a high significance, it may not be necessary to detect increased expression or accumulation in more than one BTM or UBTM. However, the redundancy in the BTMs of this invention can permit detection of bladder cancers with an increased reliability.

The methods provided herein also include assays of high sensitivity. qPCR is extremely sensitive, and can be used to detect gene products in very low copy number (e.g., 1-100) in a sample. With such sensitivity, very early detection of events that are associated with bladder cancer is made possible.

Methods

Tumor Collection

Bladder tumor samples and non-malignant urothelium samples were collected from surgical specimens resected at Kyoto University Hospital, Japan and other collaborating Japanese hospitals.

Urine Collection

Urine samples from non-malignant controls and bladder cancer patients were obtained from Kyoto University Hospital, Japan (FIG. 1). Healthy control samples were obtained from Caucasian and Japanese volunteers.

RNA Extraction

Tumor tissues were homogenized in a TriReagent:water (3:1) mix, then chloroform extracted. Total RNA was then purified from the aqueous phase using the RNeasy™ procedure (Qiagen). RNA was also extracted from 16 cancer cell lines and pooled to serve as a reference RNA.

RNA was extracted from urine by mixing the urine sample with an equal volume of lysis buffer (5.64M guanidine-HCl, 0.5% sarkosyl, 50 mM sodium acetate (pH 6.5) and 1 mM β-mercaptoethanol; pH adjusted to 7.0 with 1.5M Hepes pH 8). Total RNA was then extracted using Trizol and the RNeasy™ procedure. RNA preparations were further purified prior to cDNA synthesis using the Qiagen QIAquick™ PCR purification kit.

RNA was extracted from the blood of three healthy volunteers by performing a Trizol/RNeasy™ extraction on cells enriched from whole blood using sedimentation in 3.6% dextran.

Microarray Slide Preparation

Epoxy coated glass slides (MWG Biotech) were printed with ~30,000 50mer oligonucleotides (MWG Biotech) using a Gene Machines microarraying robot, according to the manufacturer's protocol.

RNA Labeling and Hybridization cDNA was transcribed from 5 μg total RNA using Superscript II™ reverse transcriptase (Invitrogen) in reactions containing 5-(3-aminoallyl)-2' deoxyuridine-5'-triphosphate. The reaction was then de-ionised in a Microcon column before being incubated with Cy3 or Cy5 in bicarbonate buffer for 1 hour at room temperature. Unincorporated dyes were removed using a Qiaquick column (Qiagen) and the sample concentrated to 15 μl in a SpeedVac. Cy3 and Cy5 labeled cDNAs were then mixed with Ambion ULTRAhyb™ buffer, denatured at 100° C. for 2 min and hybridized to the microarray slides in hybridisation chambers at 42° C. for 16 hours. The slides were then washed and scanned twice in an Axon 4000A™ scanner at two power settings.

Microarray Analysis of Cancer Marker Genes

RNA from 53 bladder tumors and 20 non-malignant ("normal") bladder tissue samples were labeled with Cy5 and hybridized in duplicate or triplicate with Cy3 labeled reference RNA. After normalization, the change in expression in each of 29,718 genes was then estimated by fold change and statistical probability.

Normalization Procedure

Median fluorescence intensities detected by Genepix™ software were corrected by subtraction of the local background intensities. Spots with a background corrected intensity of less than zero were excluded. To facilitate normalization, intensity ratios and overall spot intensities were log-transformed. The logged intensity ratios were corrected for dye and spatial bias using local regression implemented in the LOCFIT™ package. Logged intensity ratios were regressed simultaneously with respect to overall spot intensity and location. The residuals of the local regression provided the corrected logged fold changes. For quality control, ratios of each normalized microarray were plotted in respect to spot intensity and localization. The plots were subsequently visually inspected for any remaining artifacts. Additionally, an ANOVA model was applied for the detection of pin-tip bias. All results and parameters of the normalization were inserted into a Postgres-database for statistical analysis.

Statistical Analysis

To improve the comparison of measured fold changes between arrays, log2 (ratios) were scaled to have the same overall standard deviation per array. This standardization reduced the average within-tissue class variability. The log2 (ratios) were further shifted to have a median value of zero for each oligonucleotide to facilitate visual inspection of results. A rank-test based on fold changes was then used to improve the noise robustness. This test consists of two steps: (i) calculation of the rank of fold change (Rfc) within arrays and ii) subtraction of the median (Rfc) for normal tissue from the median (Rfc) for tumor tissue. The difference of both median ranks defines the score of the fold change rank. Three additional statistical tests were also performed on standardized data: 1) Two sample student's t-test, 2) the Wilcoxon test and 3) Statistical Analysis of Microarrays (SAM). The 300 most significantly up-regulated genes determined by each of the statistical methods (rank fold change, t-test, Wilcoxon test, and SAM) were given a rank score for each test. If a gene appeared on one list, but not one or more of the others, a weighting factor of 500 was added to its score. All rank scores were then added into one summated rank score.

Statistical Analysis of Marker Combinations

To determine the value of using combinations of two or three of the markers to discriminate between tumor and non-malignant samples, the qPCR data from tumor and non-malignant samples were subjected to the following analysis. Normal distributions for the non-malignant and tumor samples were generated using the sample means and standard deviations. The probability that values taken from the tumor expression data would exceed a defined threshold (e.g., greater than 50%, 70%, 75%, 80%, 90%, 95%, or 99%) in the non-malignant distribution was then determined (i.e., sensitivity). For combinations of markers, the probability that at least one marker exceeded the threshold was determined.

To demonstrate the value of analyzing marker combinations in urine samples, as well as tumor samples, the analysis of the normal distribution was also carried out on qPCR data obtained using urine samples from the TCC patients and non-malignant controls described in FIG. 1, series 2. The probability that values taken from the TCC patient qPCR data would exceed a defined threshold (e.g., greater than 50%, 70%, 75%, 80%, 90%, 95%, or 99%) in the non-malignant sample distribution was determined.

Methods for Detecting Bladder Cancer Markers in Urine

In several embodiments, assays for BTM can be desirably carried out on urine samples. In general, methods for assaying for oligonucleotides, proteins and peptides in these fluids are known in the art. However, for purposes of illustration, urine levels of a BTM can be quantified using a sandwich-type enzyme-linked immunosorbent assay (ELISA). For plasma or serum assays, a 5 µL aliquot of a properly diluted sample or serially diluted standard BTM and 75 µL of peroxidase-conjugated anti-human BTM antibody are added to wells of a microtiter plate. After a 30-minute incubation period at 30° C., the wells are washed with 0.05% Tween 20 in phosphate-buffered saline (PBS) to remove unbound antibody. Bound complexes of BTM and anti-BTM antibody are then incubated with o-phenylendiamine containing $H_2O_2$ for 15 minutes at 30° C. The reaction is stopped by adding 1 M $H_2SO_4$, and the absorbance at 492 nm is measured with a microtiter plate reader. It can be appreciated that anti-BTM antibodies can be monoclonal antibodies or polyclonal antisera.

Because many proteins are either (1) secreted by cells, (2) cleaved from cell membranes, (3) lost from cells upon cell death or (4) contained within sloughed cells, it will be appreciated that BTMs may also be detected in the urine. Additionally, diagnosis of bladder cancer can be determined by measuring either expression of BTMs in a sample, or accumulation of BTMs in a sample. Prior art methods of diagnosis include cystoscopy, cytology and examination of cells extracted during these procedures. Such methods have relied upon identification of tumor cells in the urine or in a brush sample of urothelium, or in other cases, in biopsy specimens of the bladder wall. These methods suffer from several types of errors, including sampling error, errors in identification between observers, and the like.

Quantitative Real-Time PCR

Real-time, or quantitative PCR (qPCR) is used for absolute or relative quantitation of PCR template copy number. Taqman™ probe and primer sets were designed using Primer Express V 2.0™ (Applied Biosystems). Where possible, all potential splice variants were included in the resulting amplicon, with amplicon preference given to regions covered by the MWG-Biotech-derived microarray oligonucleotide. Primer and probe sequences are shown in FIG. 2. Alternatively, if the target gene was represented by an Assay-on-Demand™ expression assay (Applied Biosystems) covering the desired amplicons, these were used. In the in-house designed assays, primer concentration was titrated using a SYBR green labeling protocol and cDNA made from the reference RNA. Amplification was carried out on an ABI Prism™ 7000 sequence detection system under standard cycling conditions. When single amplification products were observed in the dissociation curves, standard curves were generated over a 625 fold concentration range using optimal primer concentrations and 5'FAM-3'TAMRA phosphate Taqman™ probe (Proligo) at a final concentration of 250 nM. Assays giving standard curves with regression coefficients over 0.98 were used in subsequent assays.

Assays can be performed over two 96 well plates with each RNA sample represented by a single cDNA. Each plate contained a reference cDNA standard curve, over a 625-fold concentration range in duplicate. Analysis consisted of calculating the $\Delta CT$ (target gene CT−mean reference cDNA CT). The $\Delta CT$ is directly proportional to the negative log2 fold change. Log 2 fold changes relative to the median non-malignant log2 fold change were then calculated (log2 fold change−median normal log2 fold change). The fold changes can then be clustered into frequency classes and graphed or portrayed in box and whisker plots.

Selection of Serum and Urine Markers for Bladder Malignancy

Putative serum markers can be selected from the array data based on (i) likelihood that the encoded protein is secreted from the cell or cleaved from the membrane; the likelihood of secretion was based on analysis with TargetP™ (Emanuelsson et al; J. Mol. Biol. 300, 1005-1006 (2000)) and (ii) its summated rank score. However, variation in the degree of over-expression in the tumor samples reflects not only tumor heterogeneity but also variations in the extent of contamination of the tumor samples with "normal" tissue including smooth muscle, connective tissue, submucosal cells (see U.S. Pat. No. 6,335,170), stromal cells and non-malignant epithelium. In many situations, "normal" contamination ranged from 5 to 70% with a median of approximately 25%.

We have therefore been able to decrease these "false positive" results by analyzing BTM in samples of urine, which are not highly contaminated with normal bladder cells. Moreover, by using qPCR methods, we have been able to more accurately determine the levels of mRNA in a urine sample, compared to use of microarray methods, as in the prior art. Therefore, we have been able to avoid major contamination with other bladder cell types, and therefore have avoided one of the more intractable problems in the art of microarray analysis of clinical samples.

By measuring the accumulation of markers in the urine, and not relying upon the rate of expression in tumors, we unexpectedly found a number of BTM that are useful in detecting bladder cancer and determining its stage and/or its type. Moreover, because one of the primary signs that can cause a patient to see a physician about possible bladder cancer is the presence of blood in the urine, we have determined that BTMs that are not highly expressed in the blood can be of great value in diagnosis. These markers include IGFBP5, MGP, SEMA3F and HOXA13 (see FIG. 9).

Measuring accumulation provides advantages over defining "over expression." As noted above, increased accumulation may reflect true over expression or increased rate of expression in a molecular biological sense (i.e., increased numbers of heteronuclear RNA (hnRNA) molecules, mRNA molecules or proteins per cell per unit time. However, accumulation also can mean an increased amount of marker in a given volume, such as in urine, even if the rate of expression is not increased. For example, even if a tumor cell produces a normal amount of a marker, an observed increase in the number of such cells in the sample can indicate the presence of cancer. In addition, accumulation may reflect free or soluble RNA in a sample. In some cases, tumor cells that produced a marker may die and the cellular contents released into the surrounding tissue. If cellular contents can reach the urine, then free marker RNA can be detected there. These phenomena may be particular useful in diagnosing superficial bladder cancer, which has typically been difficult to accomplish with selectivity and specificity. Measuring an accumulation of marker in the urine may be one of the first signs of superficial bladder cancer. Therefore, using the methods and devices of this invention, it can be possible to detect early-stage bladder cancer.

We also note that in measuring accumulation, care may be needed to correct for changes in sample volume. For example, in urine, the amount of a marker per unit volume can depend upon the renal function of the subject. Thus, in conditions of decreased urine production, cells in the urine (including tumor cells) may be concentrated, thereby giving an artificially higher measure of accumulation (per unit volume). Such artifacts can be decreased by making independent measurements of urine production (e.g, urinary output per unit time), urinary clearance (e.g., measuring creatinine or BUN). Conversely, in situations in which urine output is increased, such as in diuresis, cells containing markers may be diluted and produce an artificially low measure of accumulation. However, one can control the use of diuretics, water intake and other factors that may produce variations in marker accumulation that are not related to the true accumulation or mass of the marker in a sample. In these situations, one can correct the amount of a marker for the rate of urine production.

Therefore, by measuring BTMs in the urine, we have been able to reduce the incidence of false positive results, compared to prior art methods, indicating that these methods are superior to prior art methods.

Urine markers were selected from the array data as described above except the criteria of secretion or cleavage from the membrane was not applied. Therefore, intracellular and membrane-bound markers that were not predicted to be useful serum markers are included as urine markers.

EXAMPLES

The examples described herein are for purposes of illustrating embodiments of the invention and are not intended to limit the scope of the invention. Other embodiments, methods and types of analyses are within the scope of persons of ordinary skill in the molecular diagnostic arts and need not be described in detail hereon. Other embodiments within the scope of the art that are based on the teachings herein are considered to be part of this invention.

Example 1

Identification of Markers for Superficial and Invasive Malignancy of the Bladder Hierarchal clustering of microarray data from the gene expression patterns of invasive and superficial bladder cancer showed large numbers of significant differences. As a result, these cancer types were treated separately in the following analyses. Nevertheless, a high proportion of genes are over-expressed in both cancer types. FIG. 3 depicts a table that shows results of microarray studies for markers for invasive bladder malignancy. Thirty-one of the 199 invasive markers meet the above-stated criteria for serum markers (Denoted by "S" in figure). FIG. 4 depicts a table that shows results of microarray studies for superficial bladder malignancy. Thirty-four of the 170 superficial markers meet the above criteria for serum markers. FIGS. 3 and 4 include the HUGO symbol for the gene ("symbol"), the MWG Biotech oligonucleotide number, the NCBI mRNA reference sequence number, the protein reference sequence number, the mean fold change between tumor and non-malignant gene expression, the maximum fold change between the expression in individual tumor samples and the median expression in non-malignant samples, the results of an original unadjusted Student's t-test, the results of the 2-sample Wilcoxon test and the summated rank score.

The mean fold change (tumor: non-malignant tissue) for the 199 genes in the invasive bladder cancer marker analysis ranged from 1.3 to 5.3 and the maximum fold change ranged from 2.1 to 60.9. For the superficial bladder cancer analyses, the 170 markers ranged from mean over-expression of 1.1.3 to 3.0 and maximum over-expression ranged from 1.9 to 144. For each of the markers shown, the statistical significance of their specificity as cancer markers was found to be extremely high. The student t-test values were, with few exceptions, all below $10^{-3}$, indicating that diagnosis using these markers is very highly associated with bladder cancer. It should be noted that the fold changes generated by microarray studies tend to underestimate the actual expression changes observed using more precise techniques such as qPCR. However, for reasons described elsewhere, microarray analyses can suffer from one or more serious artifacts. Therefore, we developed a qPCR-based method for more accurately detecting the presence and the stage of bladder cancer.

Example 2 qPCR Analysis

More sensitive and accurate quantitation of gene expression was obtained for a subset of the genes shown in FIGS. 3 & 4 using qPCR. Messenger RNA from up to 30 invasive bladder tumors, 25 superficial bladder tumors, and 18 samples of normal urothelium were analyzed for 18 genes identified by the microarray analysis (FIGS. 3 & 4), with the results shown in FIG. 5. Data for both invasive and superficial type bladder cancer is shown for markers SPAG5, TOP2a, CDC2, ENG, NRP1, EGFL6, SEM2, CHGA, UBE2C, HOXA13, MDK, THY1, BIRC5 and SMC4L1. Markers SEMA3F, IGFBP5, and NOV were only over-expressed compared to normal urothelium in the superficial type alone, and MGP was only over-expressed in the invasive type alone; these markers maintained similar expression to normal urothelium in the tumor samples that were not over-expressed. FIG. 5 includes the gene name, gene aliases, the gene symbol, the median fold change between tumor (T) and non-malignant (N) tissue, the maximum fold change between individual tumor samples and the median non-malignant tissue expression and the % of tumor samples with expression levels greater than the $95^{th}$ percentile of expression levels in non-malignant samples.

The median fold change (tumor tissues compared to the median non-malignant tissue expression) for the markers in FIG. 5, except CHGA, ranged from 2 to 128 fold for invasive bladder tumors and 2 to 39 fold for superficial bladder tumors. The maximum fold change for invasive tumors ranged from 24 to 2526 fold, and for superficial tumors from 6 fold to 619 fold. The expression pattern of CHGA was notable because it had very high expression in a proportion of tumors (FIG. 6s-6t), but undetectable expression in the remainder. Expression was undetectable in 15/25 superficial tumors, 15/29 invasive tumors and 9/10 normal samples. The low expression in normal samples precludes accurate quantification of the level of over-expression in tumors as a ratio compared to normal, but when accumulation of BTM mRNA can be measured and quantified and used as a basis for diagnosis of bladder cancer. For invasive tumors, the level of expression of genes SPAG5, TOP2A and CDC2 was greater in tumors than the 95$^{th}$ percentile of the 'normal' range for ≥90% of cases. With the exception of BIRC5, the remaining genes from FIG. 5 that were examined in invasive tumors had expression greater than the 95$^{th}$ percentile of normal in >45% of samples. In superficial rumors, the level of expression of genes SPAG5, TOP2A, CDC2, ENG and NRP1 was greater in tumors than the 95$^{th}$ percentile of the non-malignant range for ≥80% of cases. With the exception of CHGA, UBE2C and BIRC5, the remaining genes from FIG. 5 that were examined in superficial tumors had expression greater than the 95$^{th}$ percentile of normal in >40% of samples.

Figure 6C:
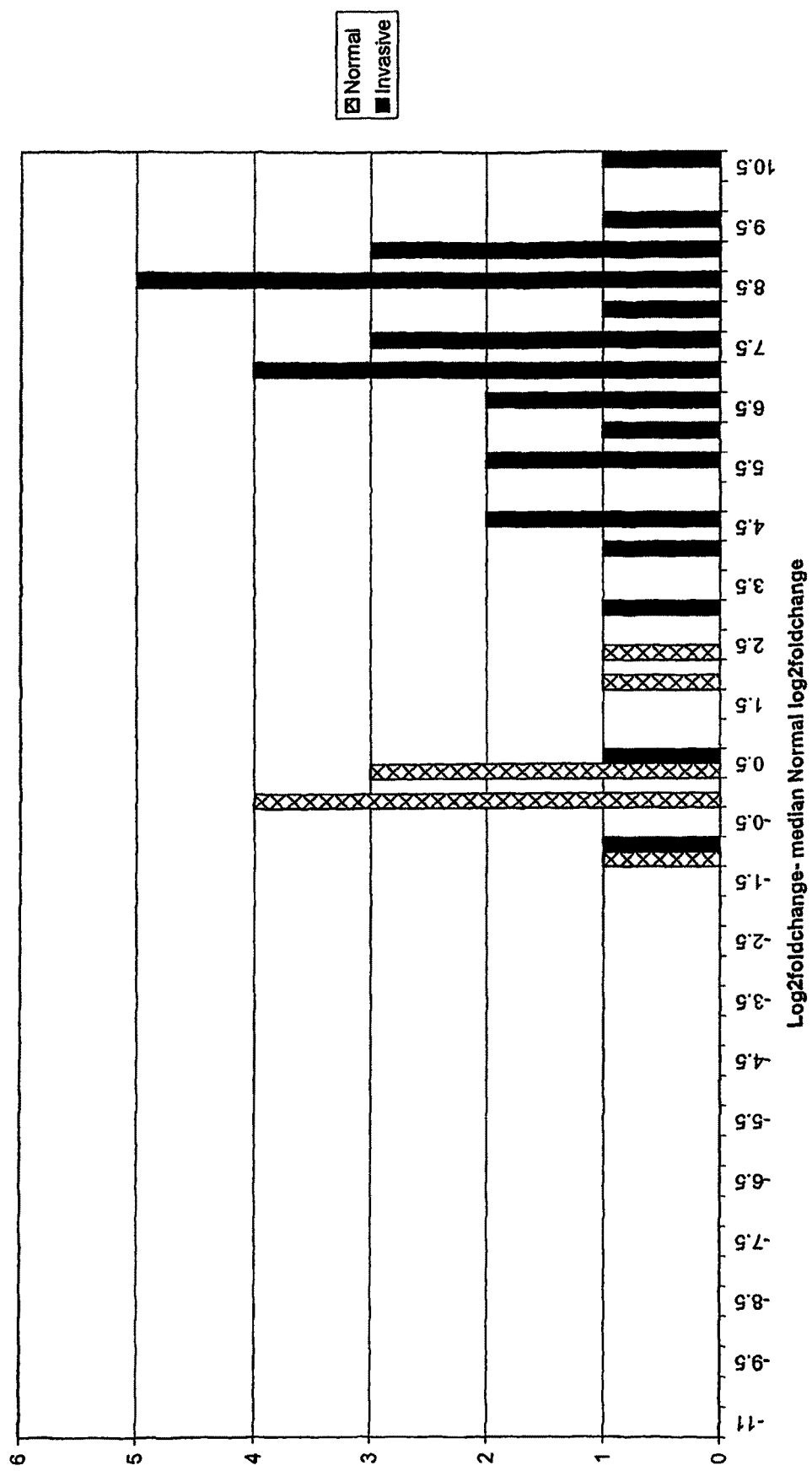
FIG. 6c: TOP2a, invasive.
Figure 6D:
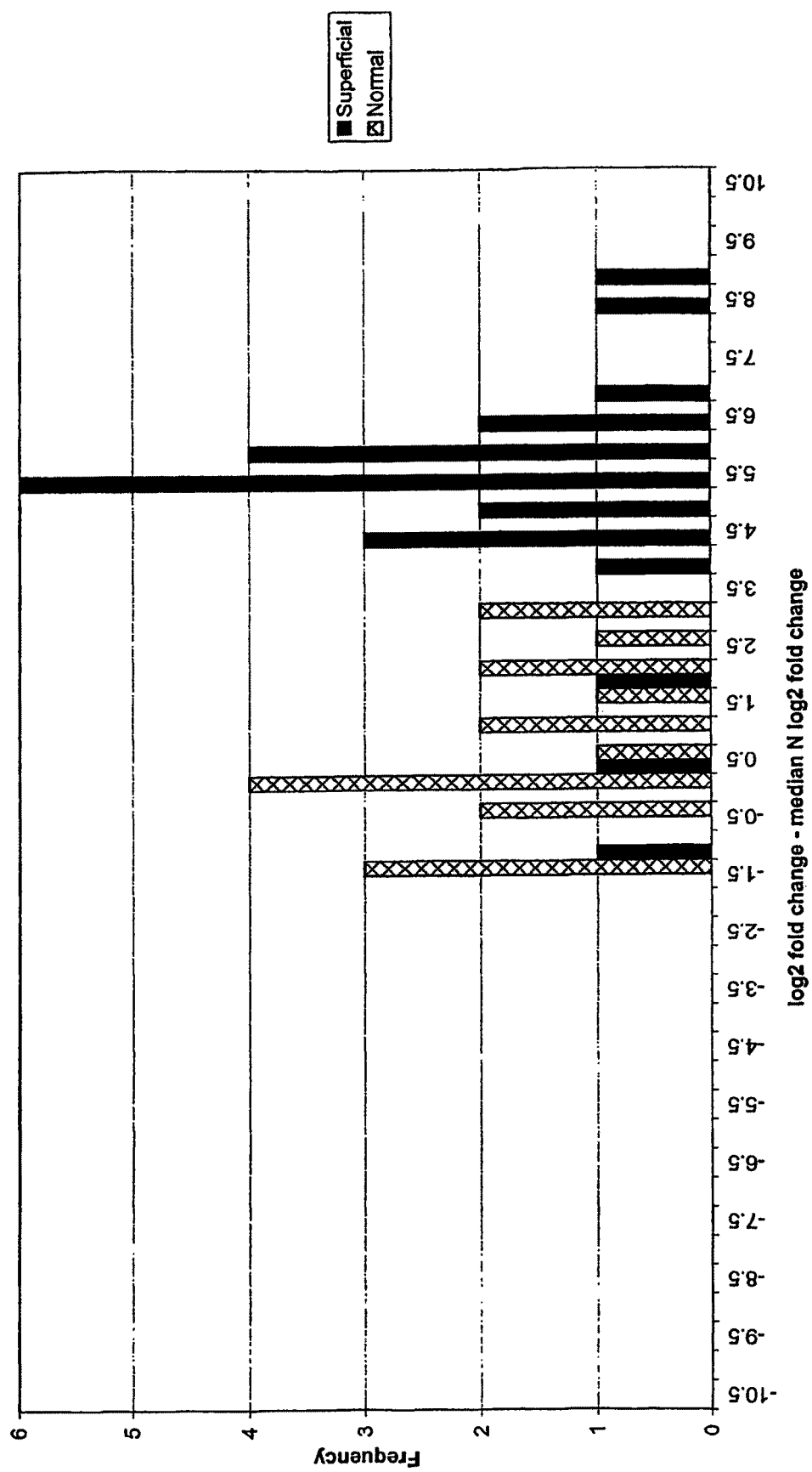
FIG. 6d: TOP2a, superficial.
Figure 6E:
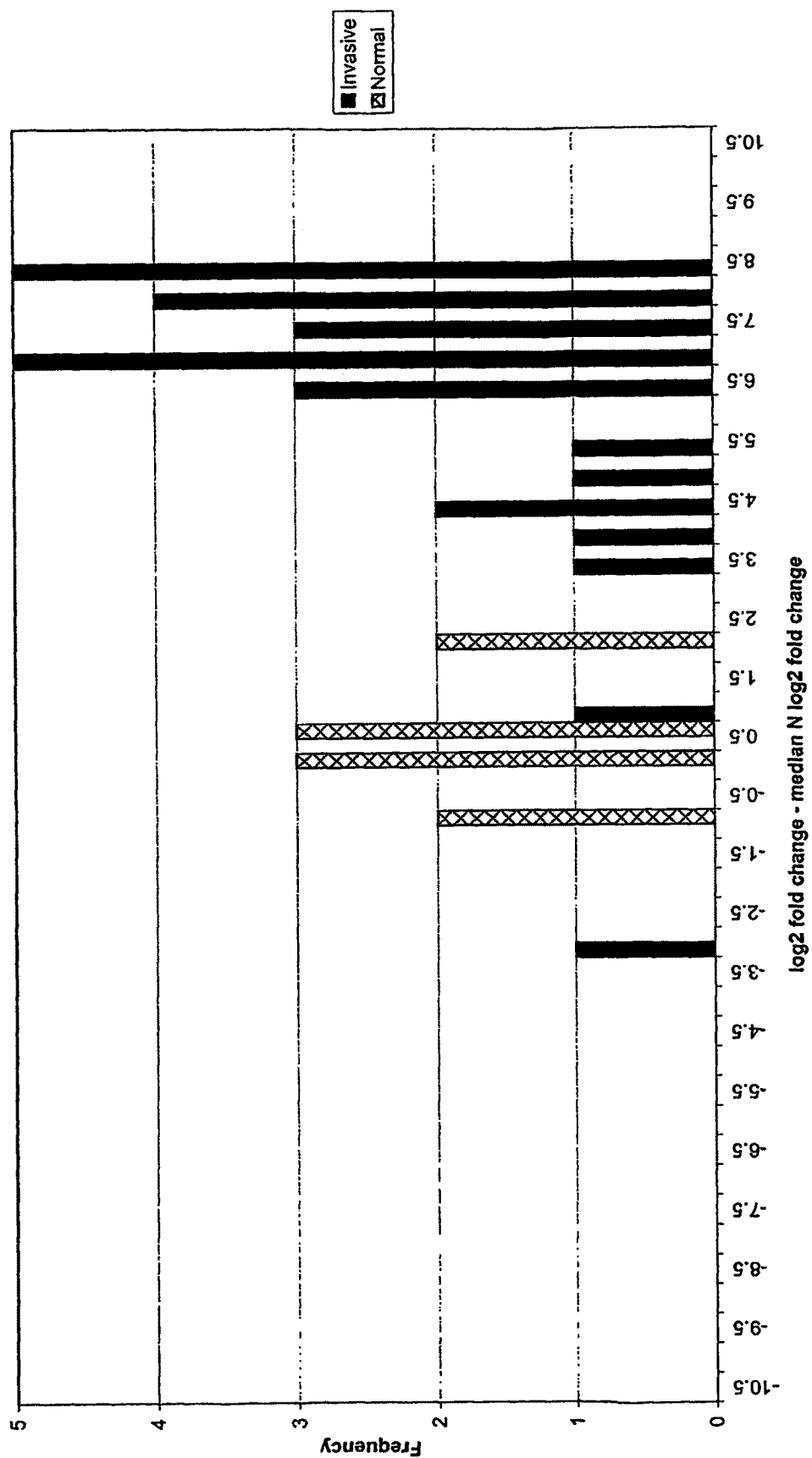
FIG. 6e: $CDCl_2$, invasive.
Figure 6F:
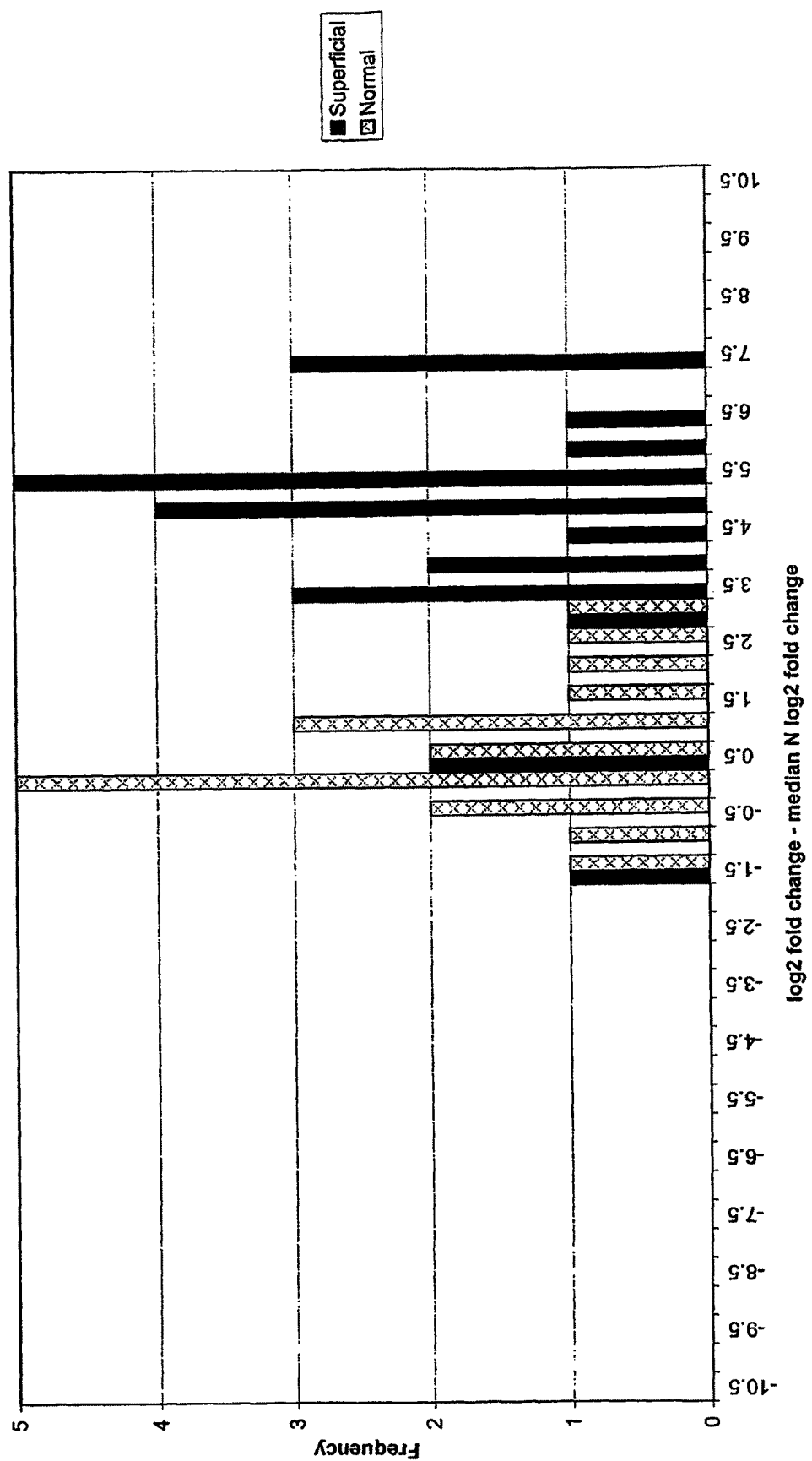
FIG. 6f: $CDCl_2$, superficial.
Figure 6G:
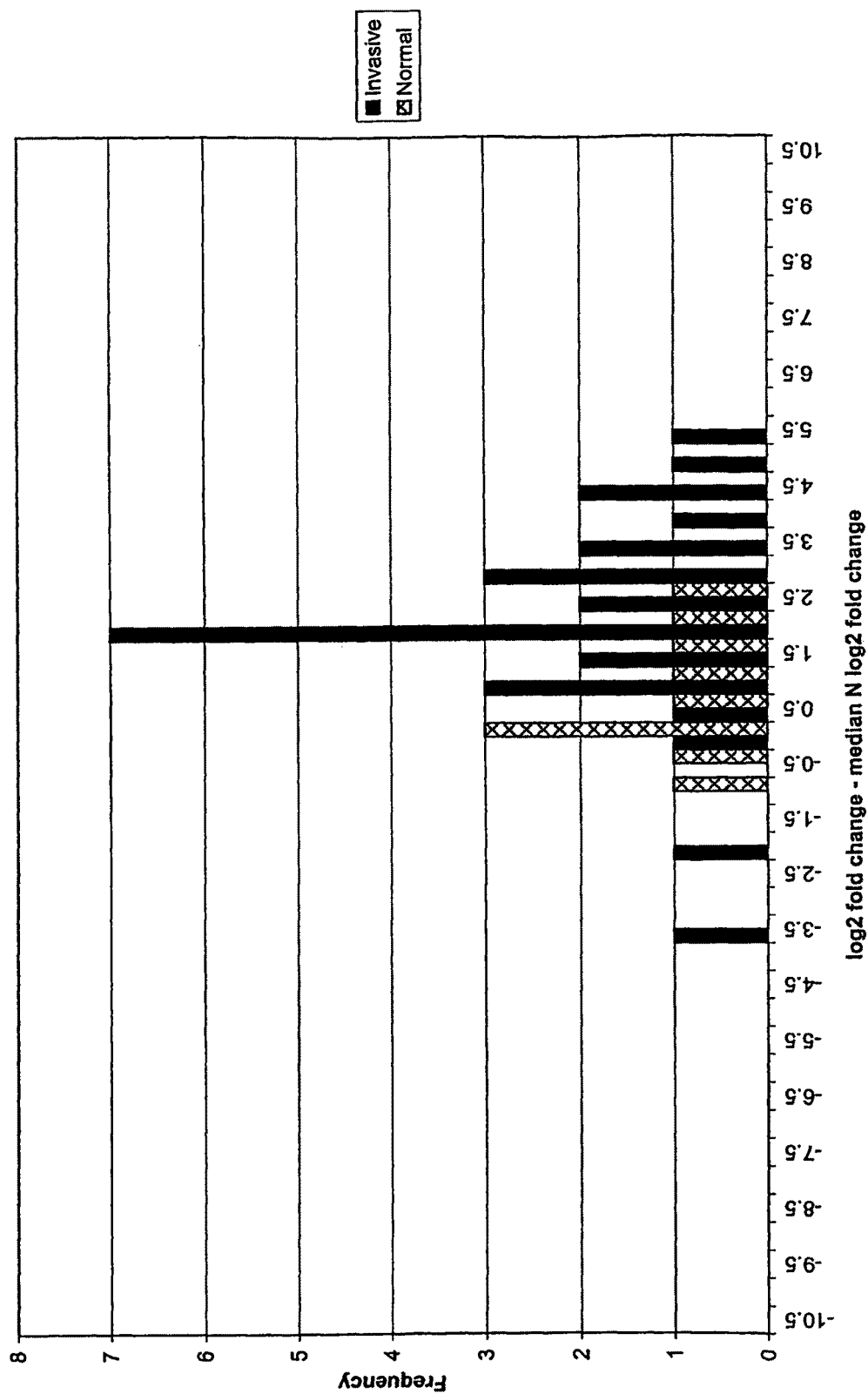
FIG. 6g: ENG, invasive.
Figure 6J:
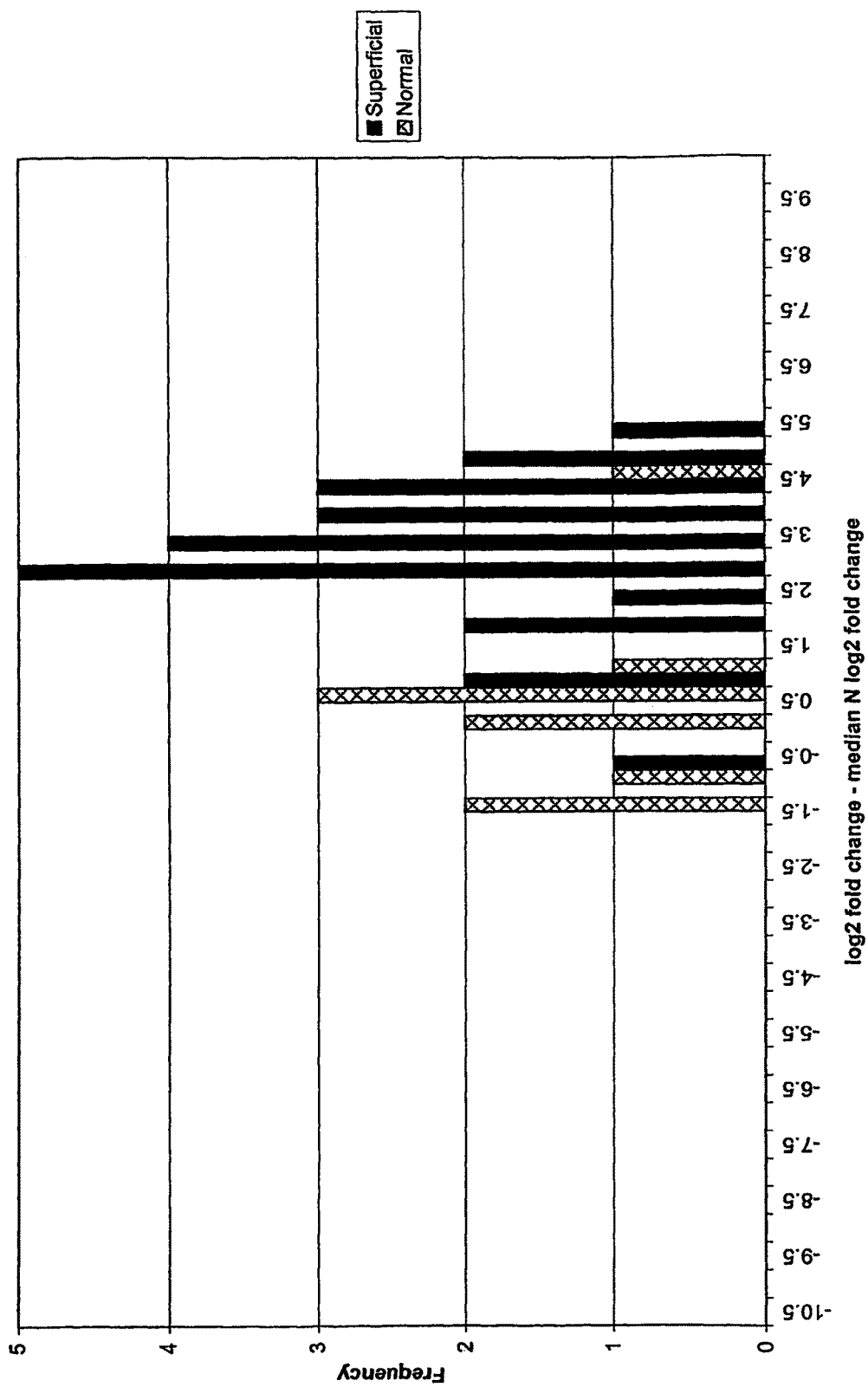
FIG. 6j: NOV, superficial.
Figure 61:
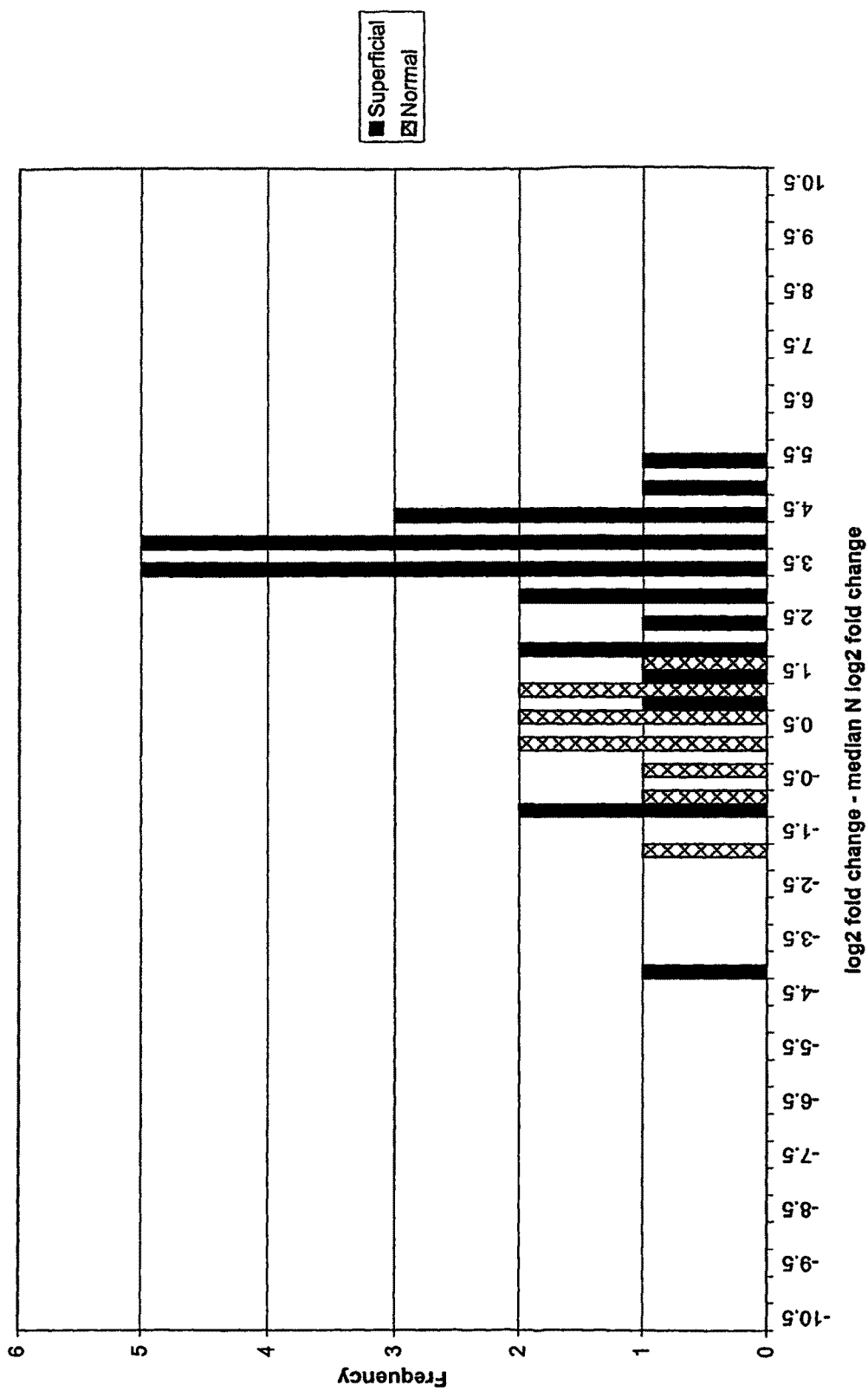
Figure 6M:
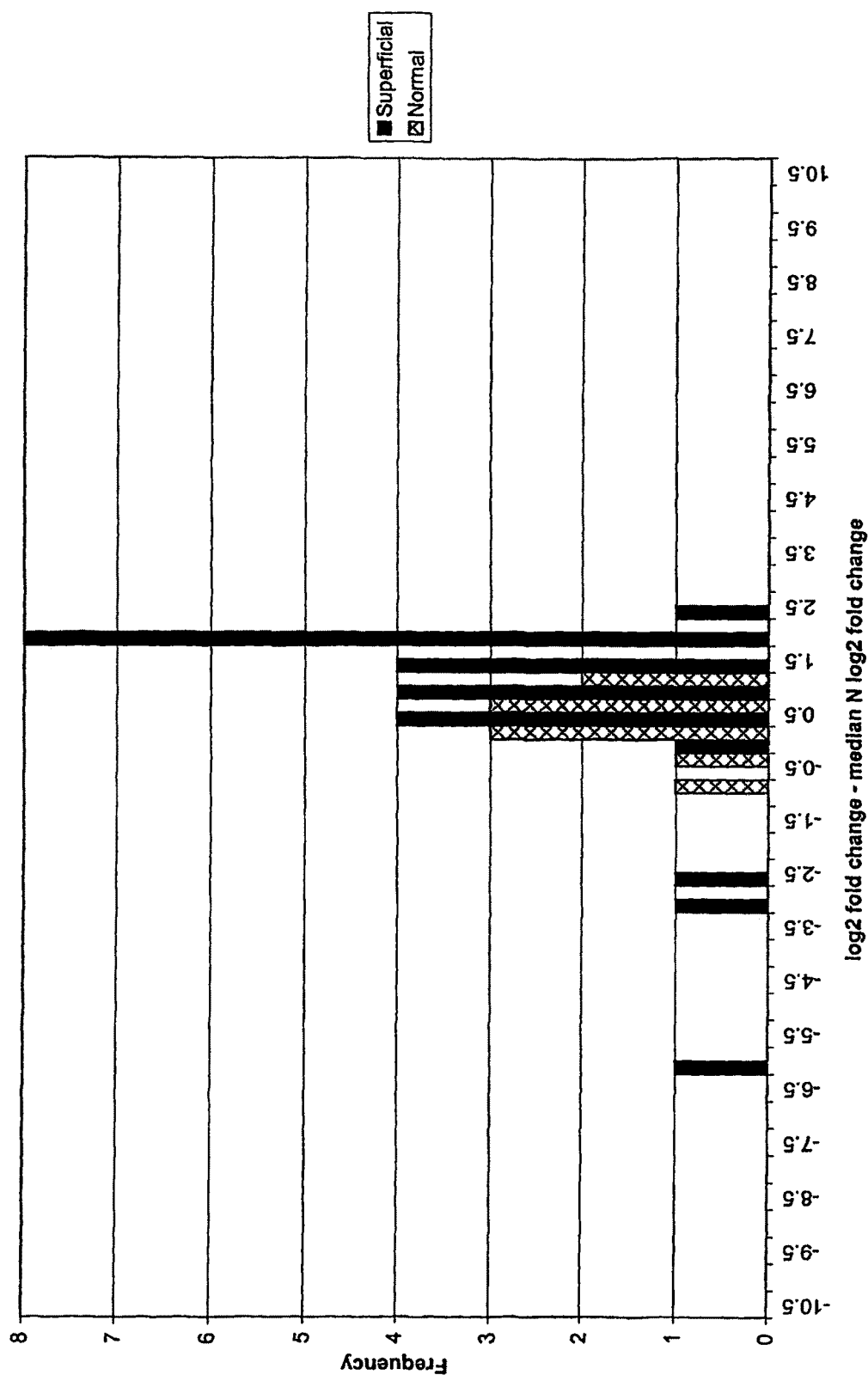
FIG. 6m: SEMA3F, superficial.
Figure 6N:
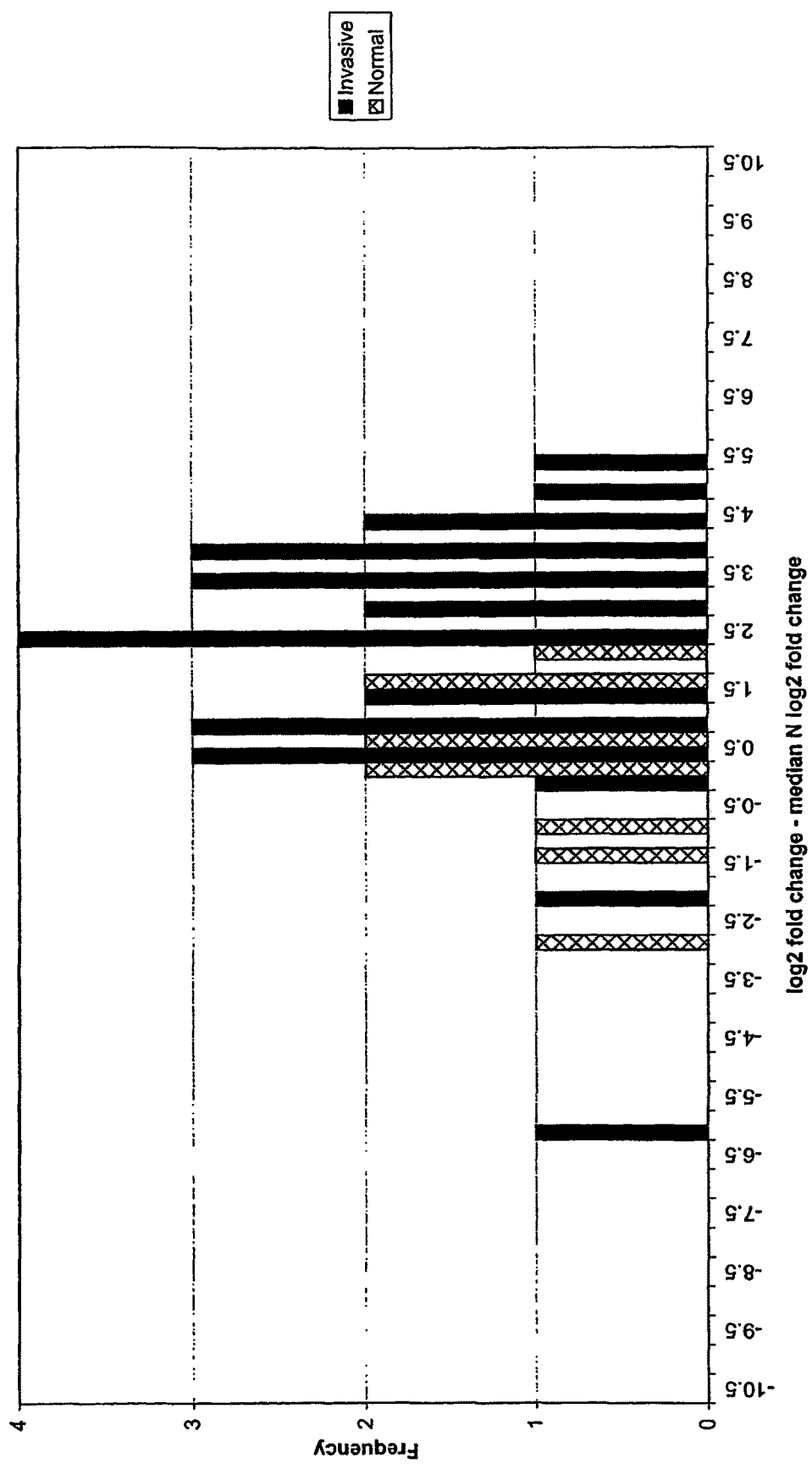
FIG. 6n: EGFL6, invasive.
Figure 60:
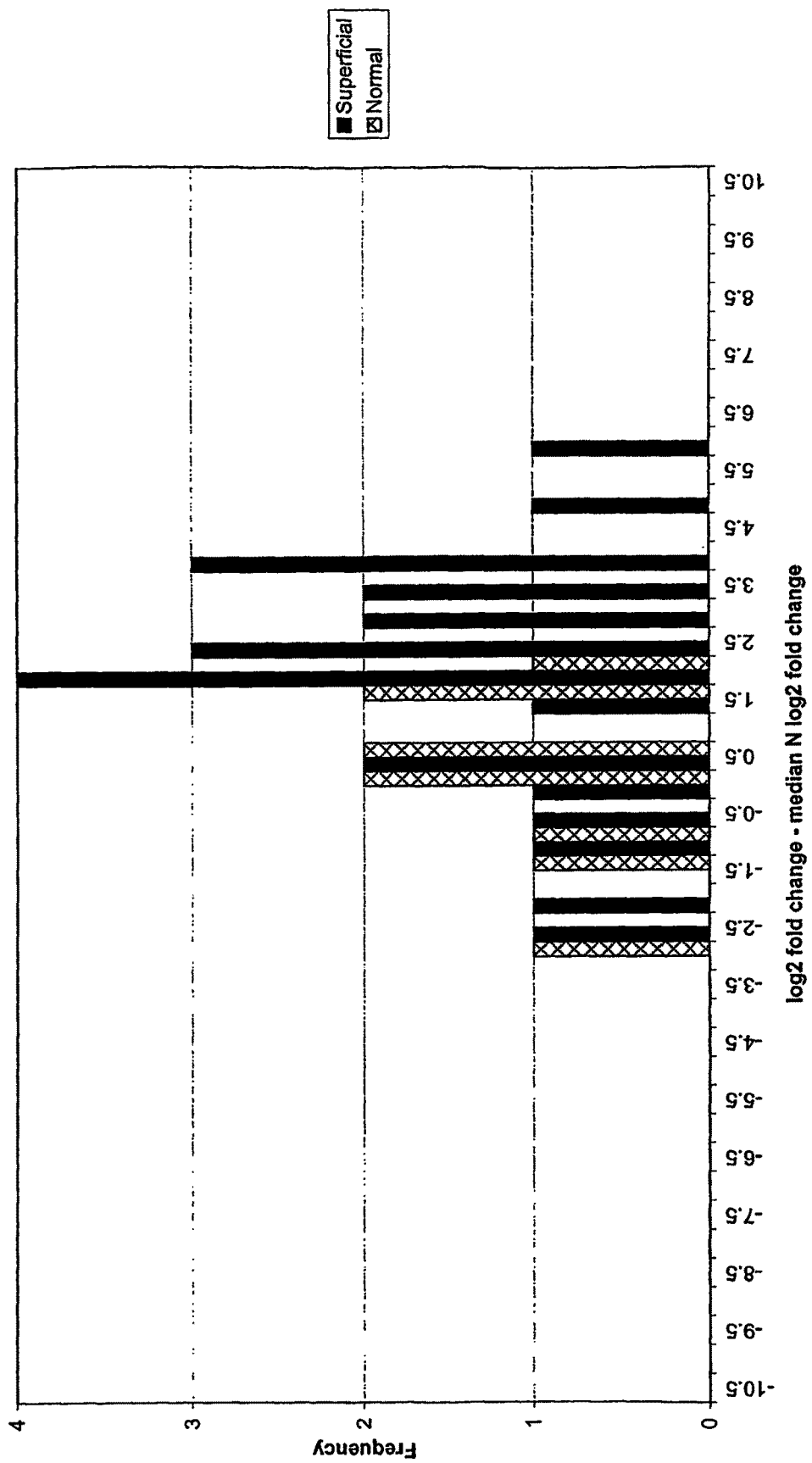
Figure 6P:
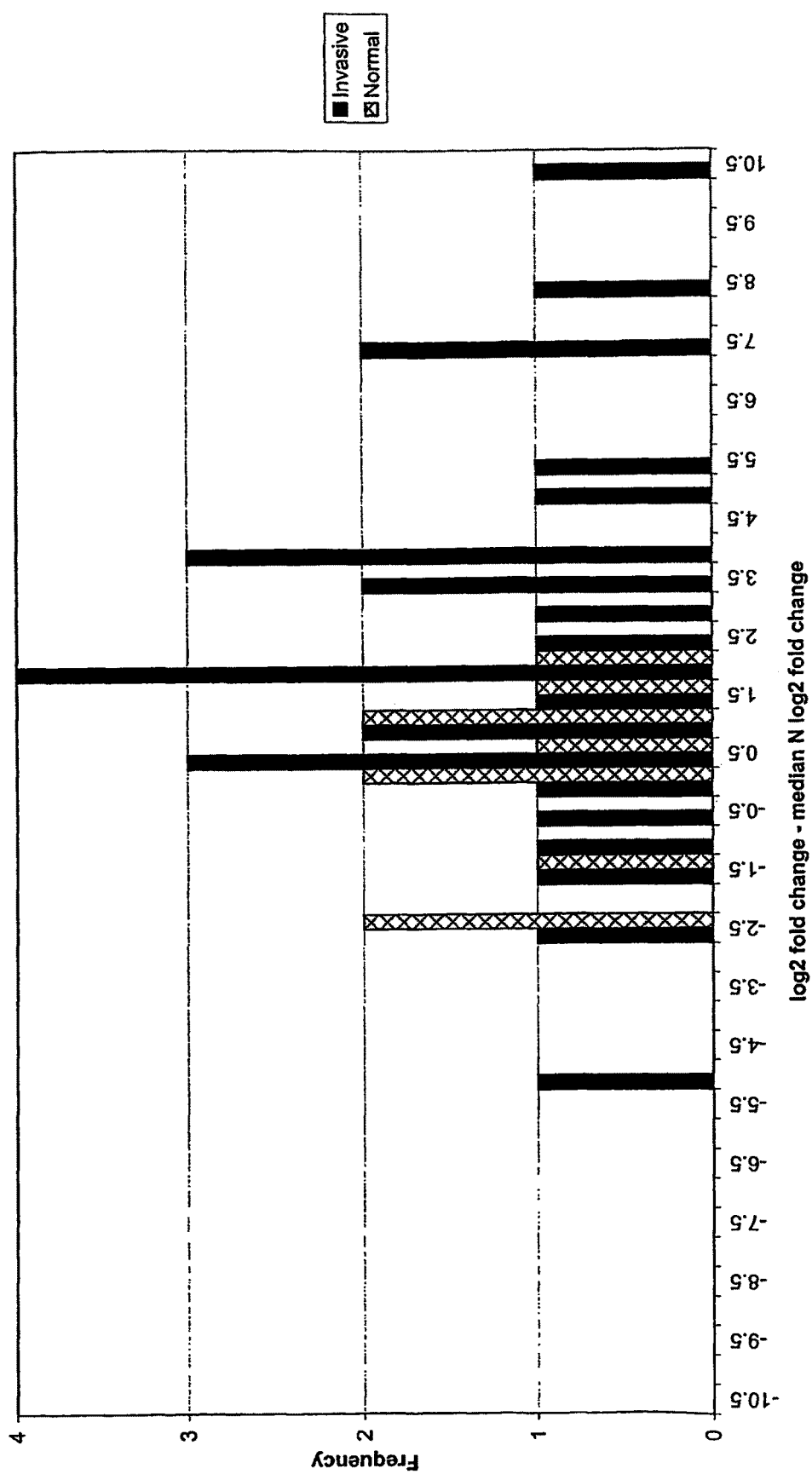
FIG. 6p: MGP, invasive.
Figure 6Q:
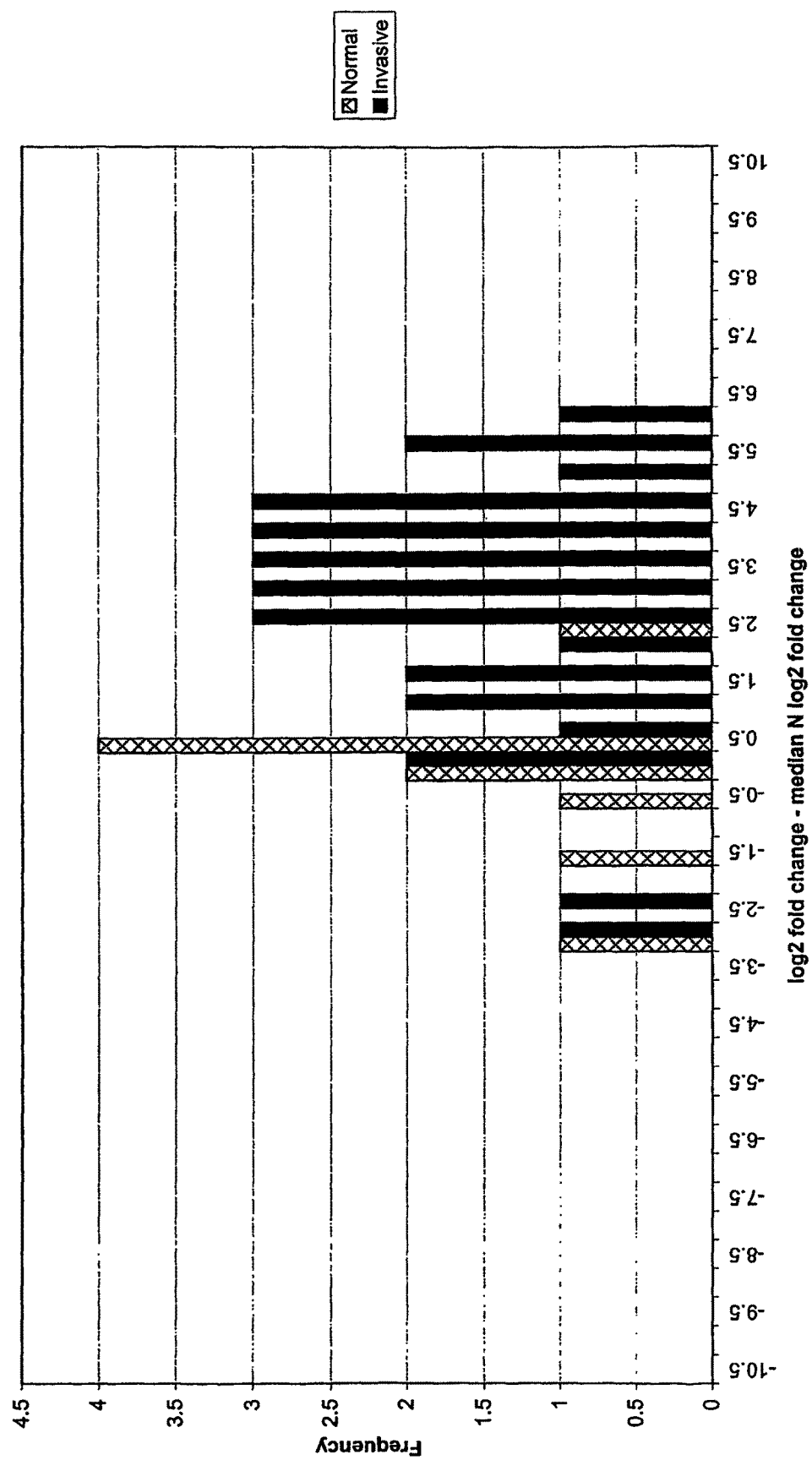
FIG. 6q: SEM2, invasive.
Figure 6R:
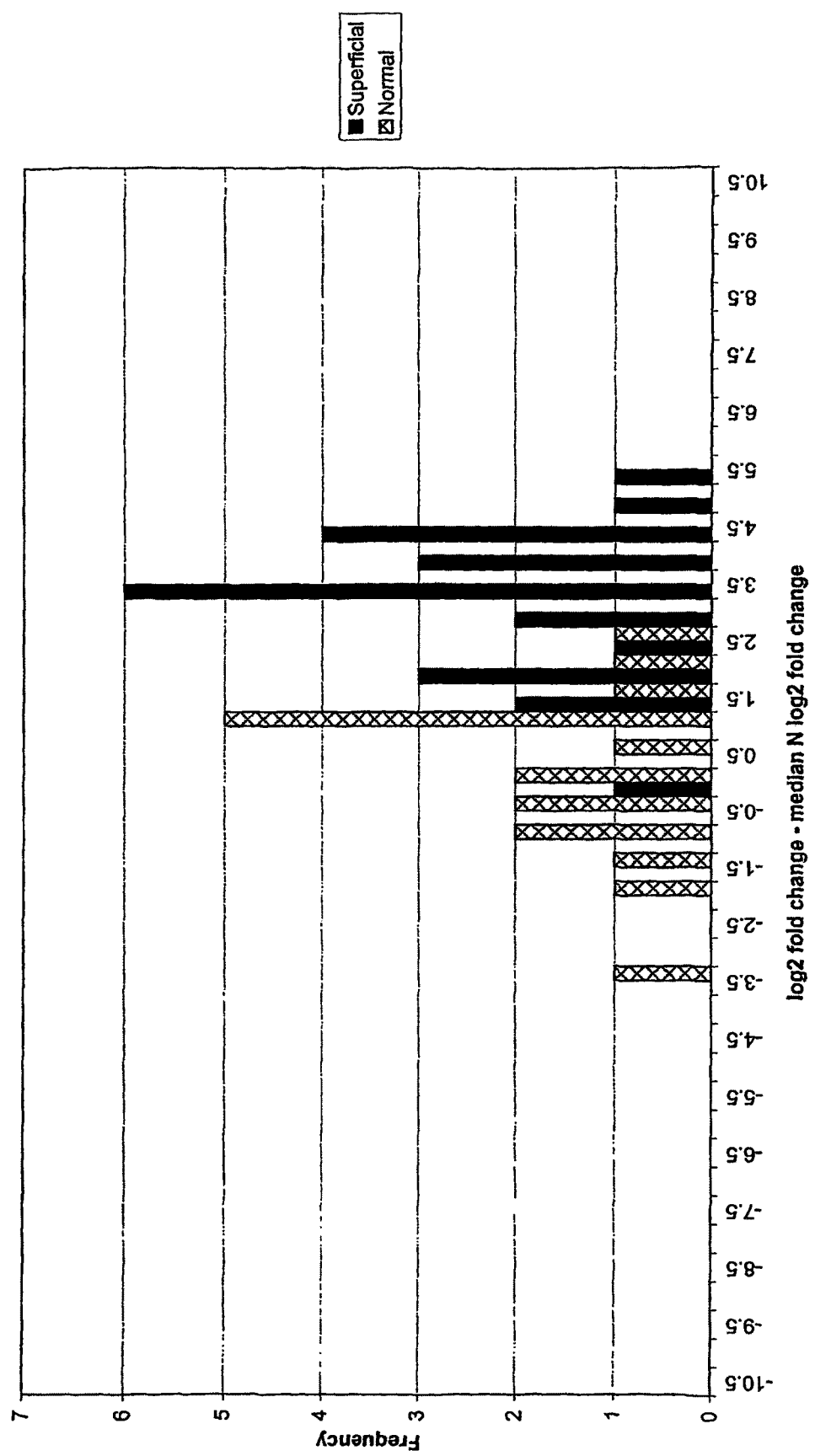
FIG. 6r: SEM2, superficial.
Figure 6S:
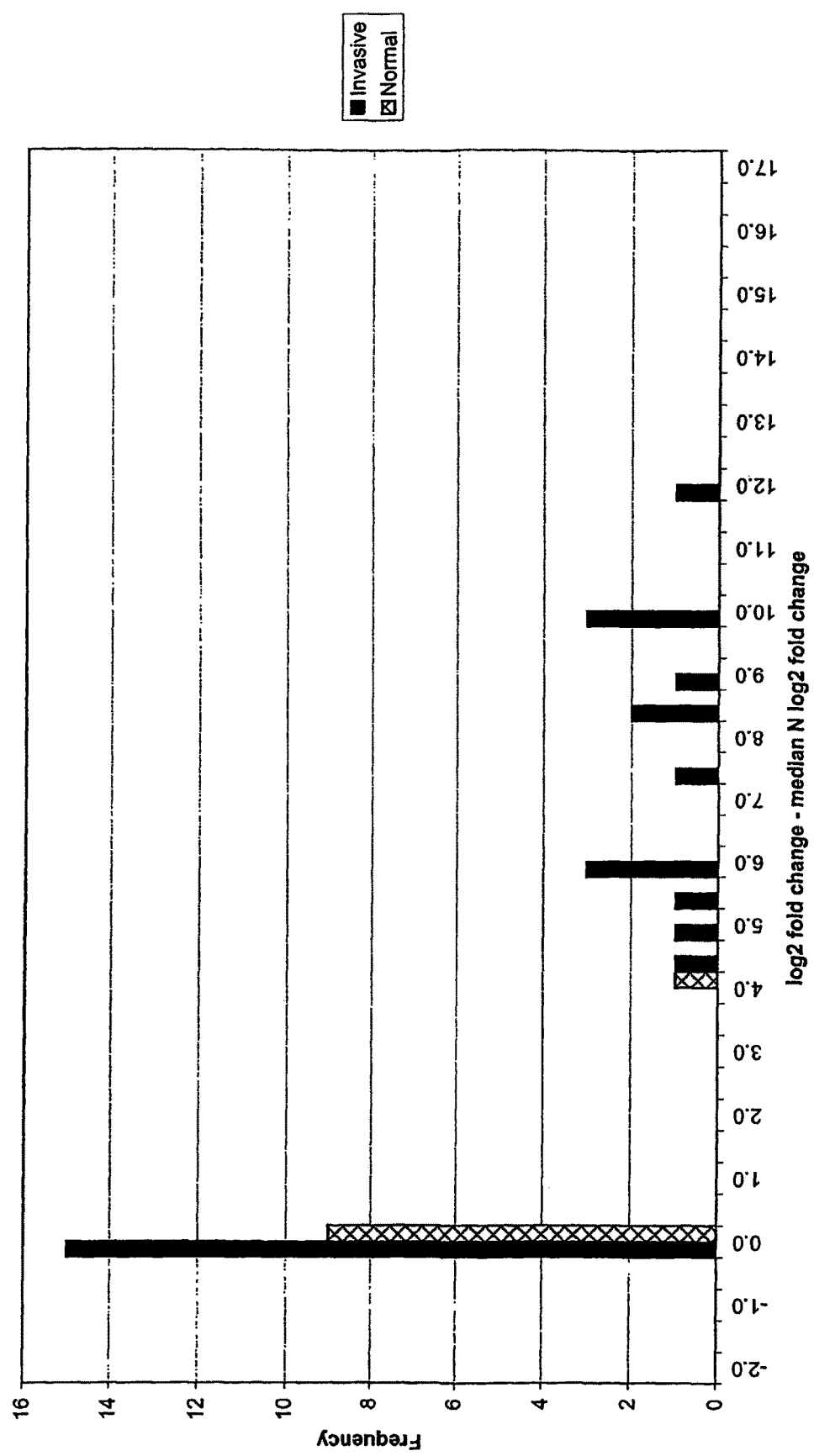
FIG. 6s: CHGA, invasive.
Figure 6T:
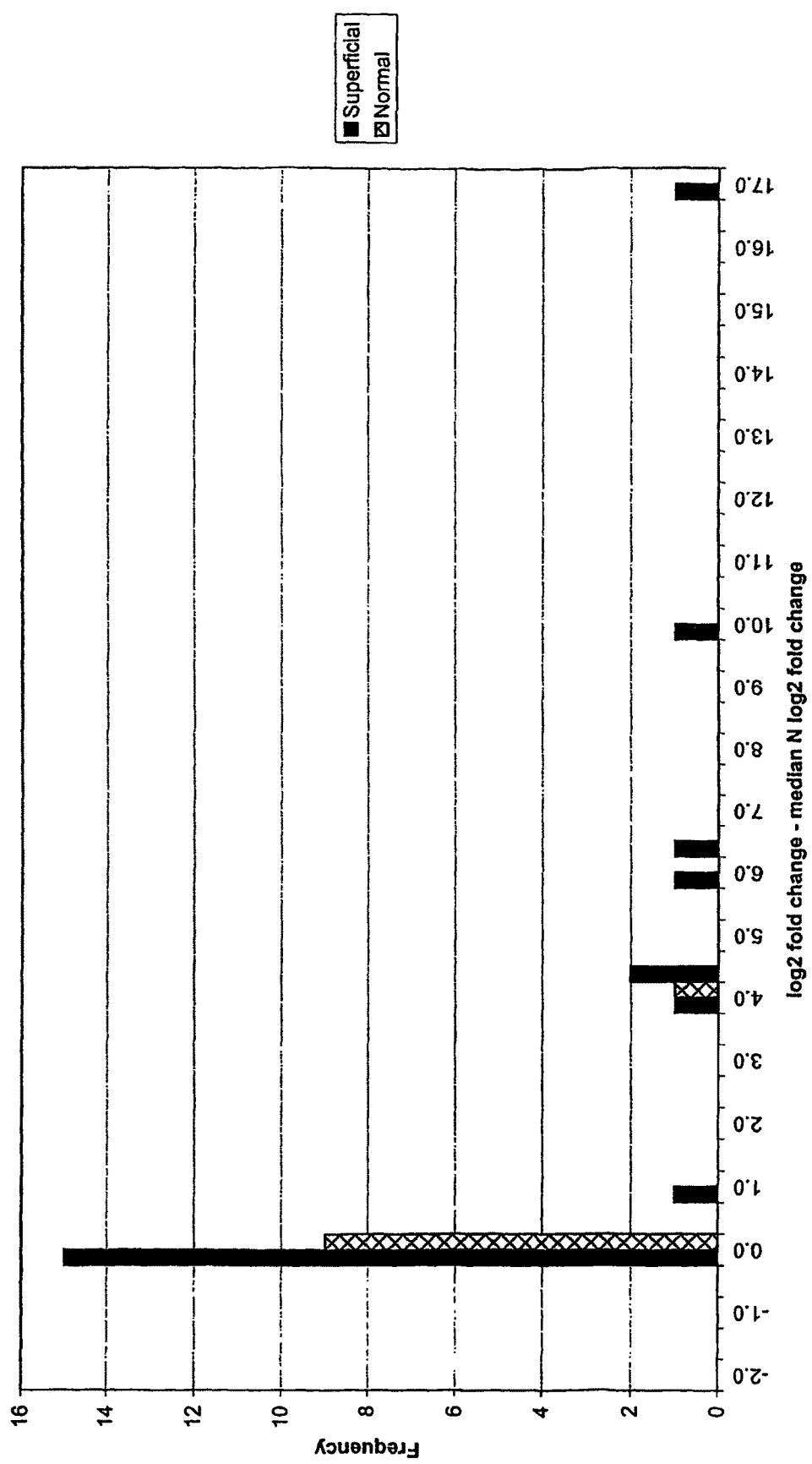
FIG. 6t: CHGA, superficial.
Figure 6U:
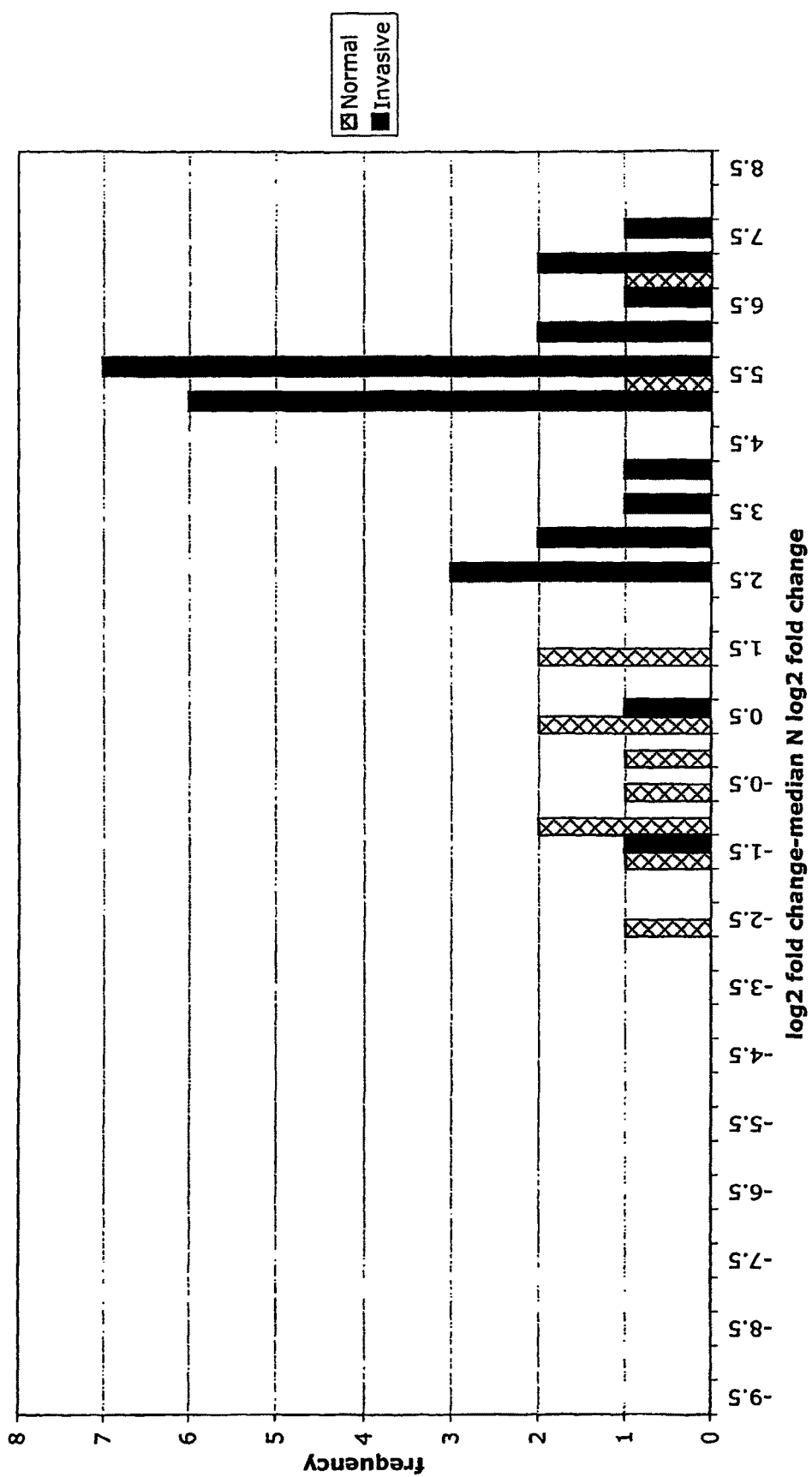
FIG. 6u: BIRC5, invasive.
Figure 6V:
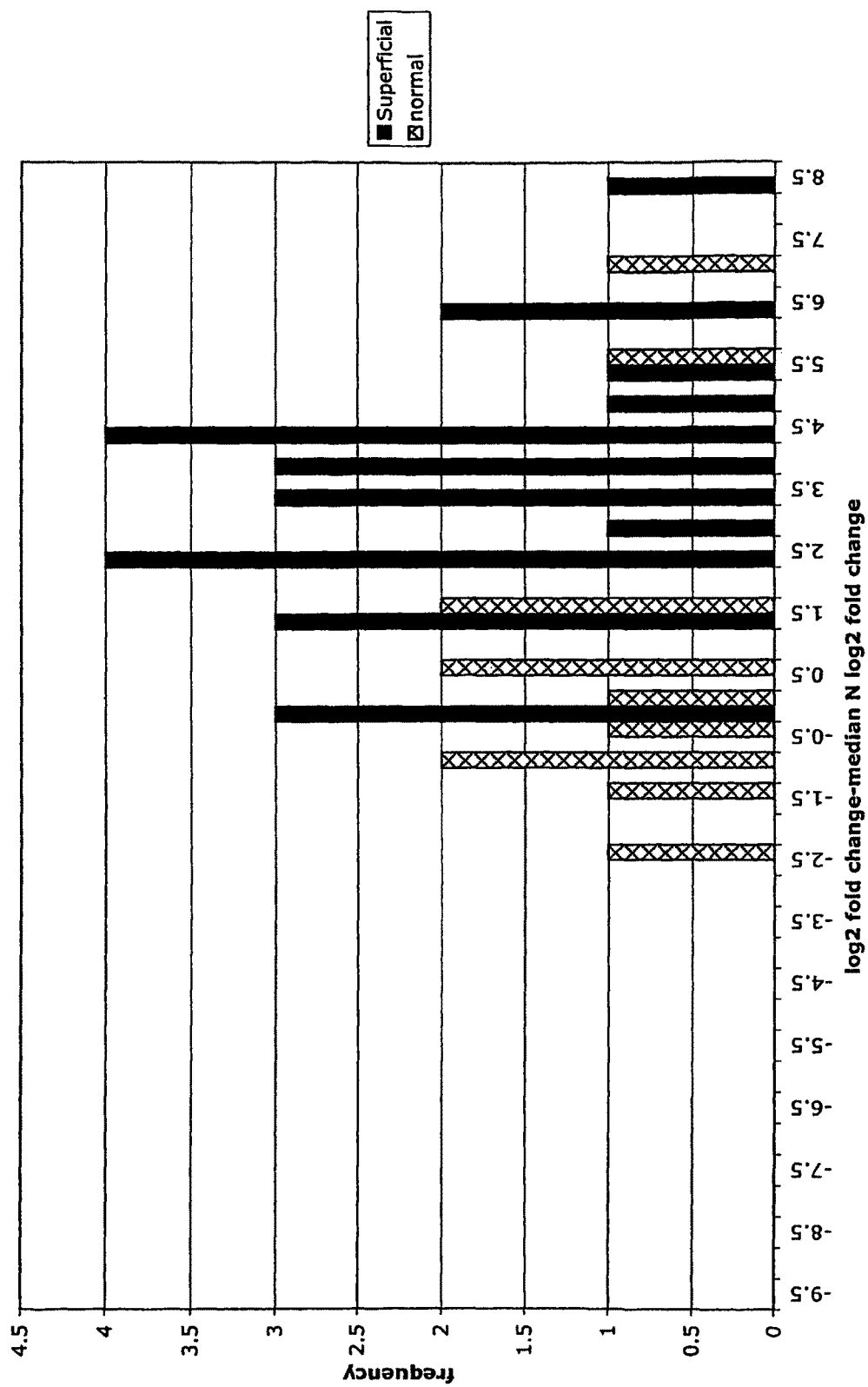
FIG. 6v: BIRC5, superficial.
Figure 6W:
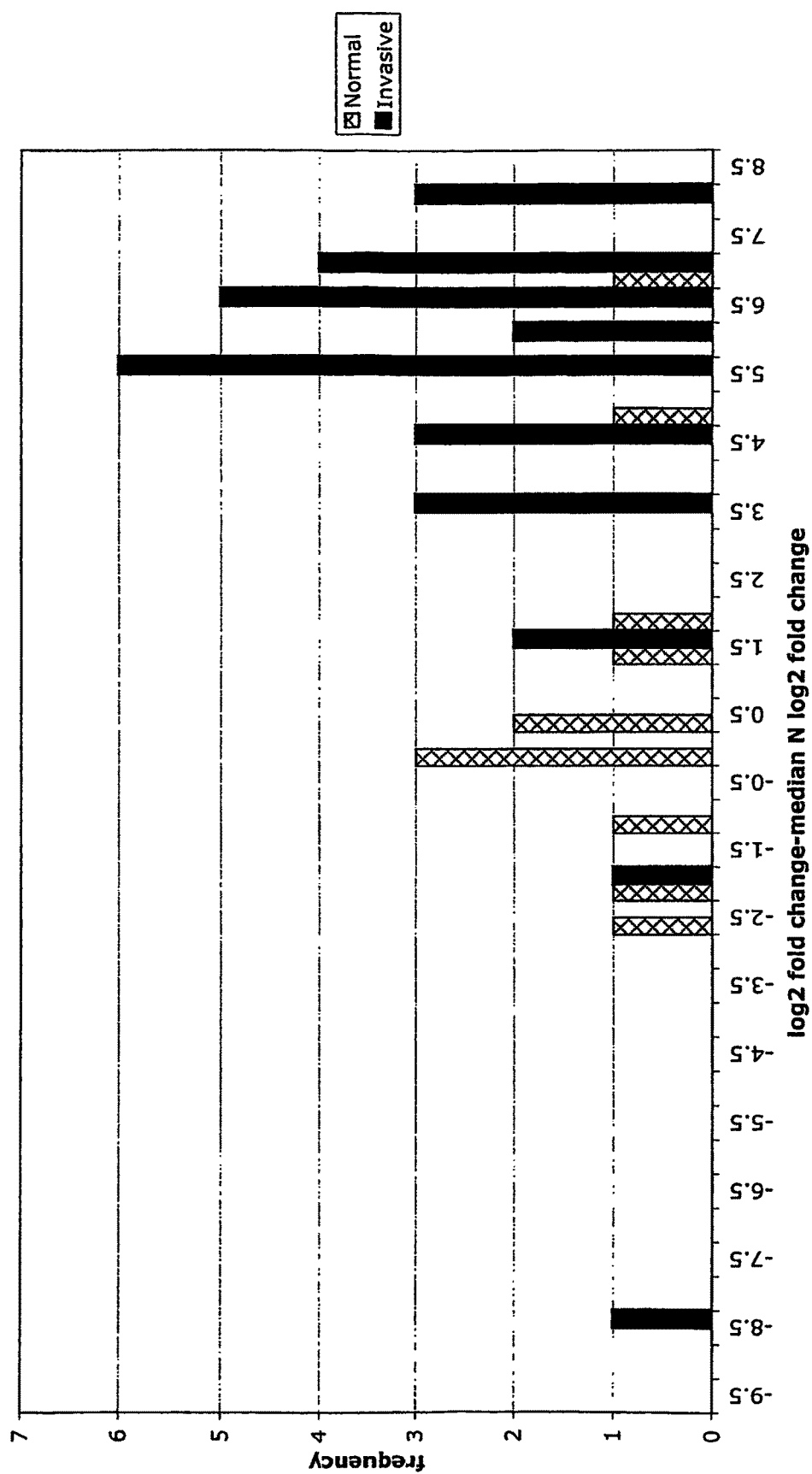
FIG. 6w: UBE2C, invasive.
Figure 6Y:
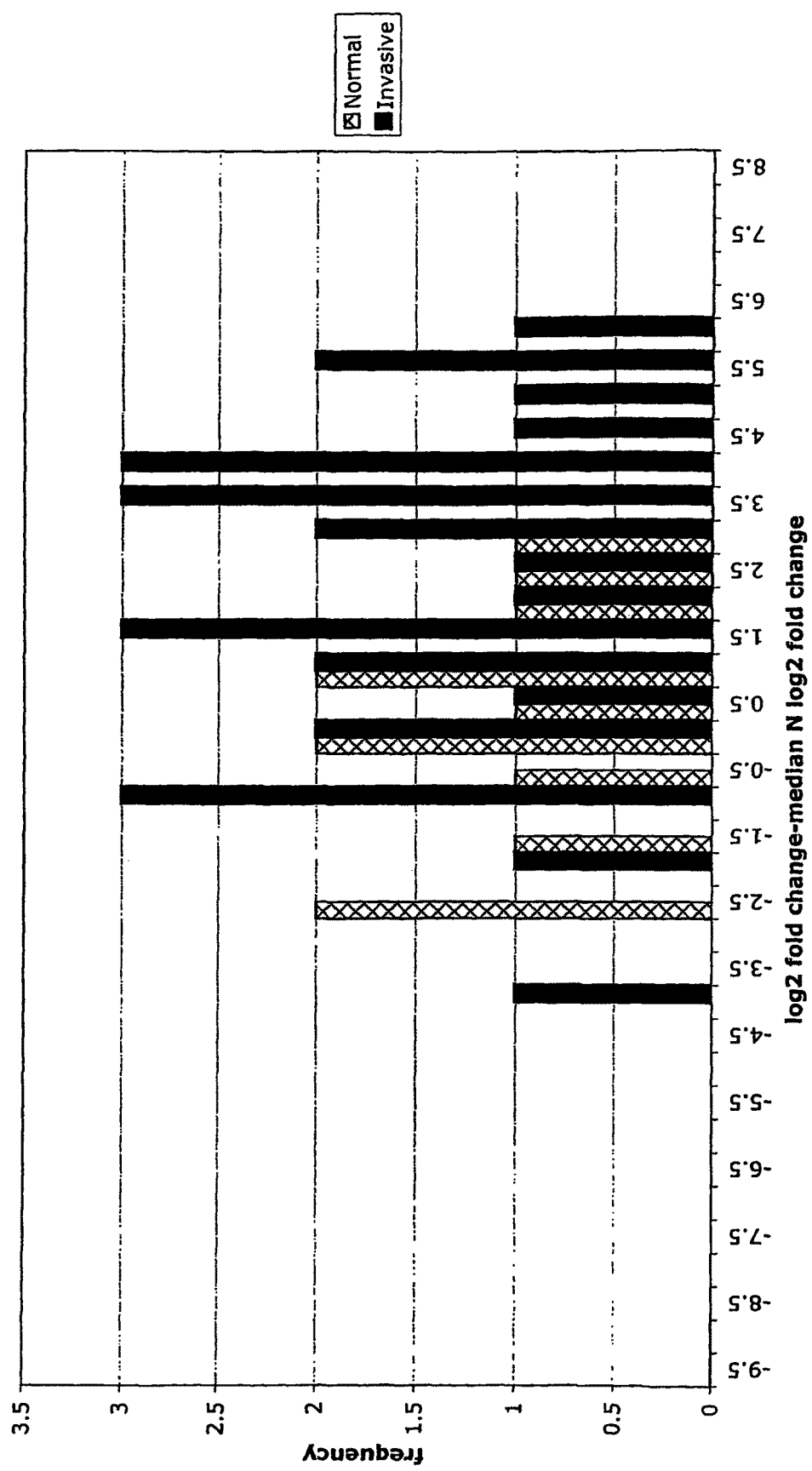
FIG. 6y: HoxA13, invasive.
Figure 6A:
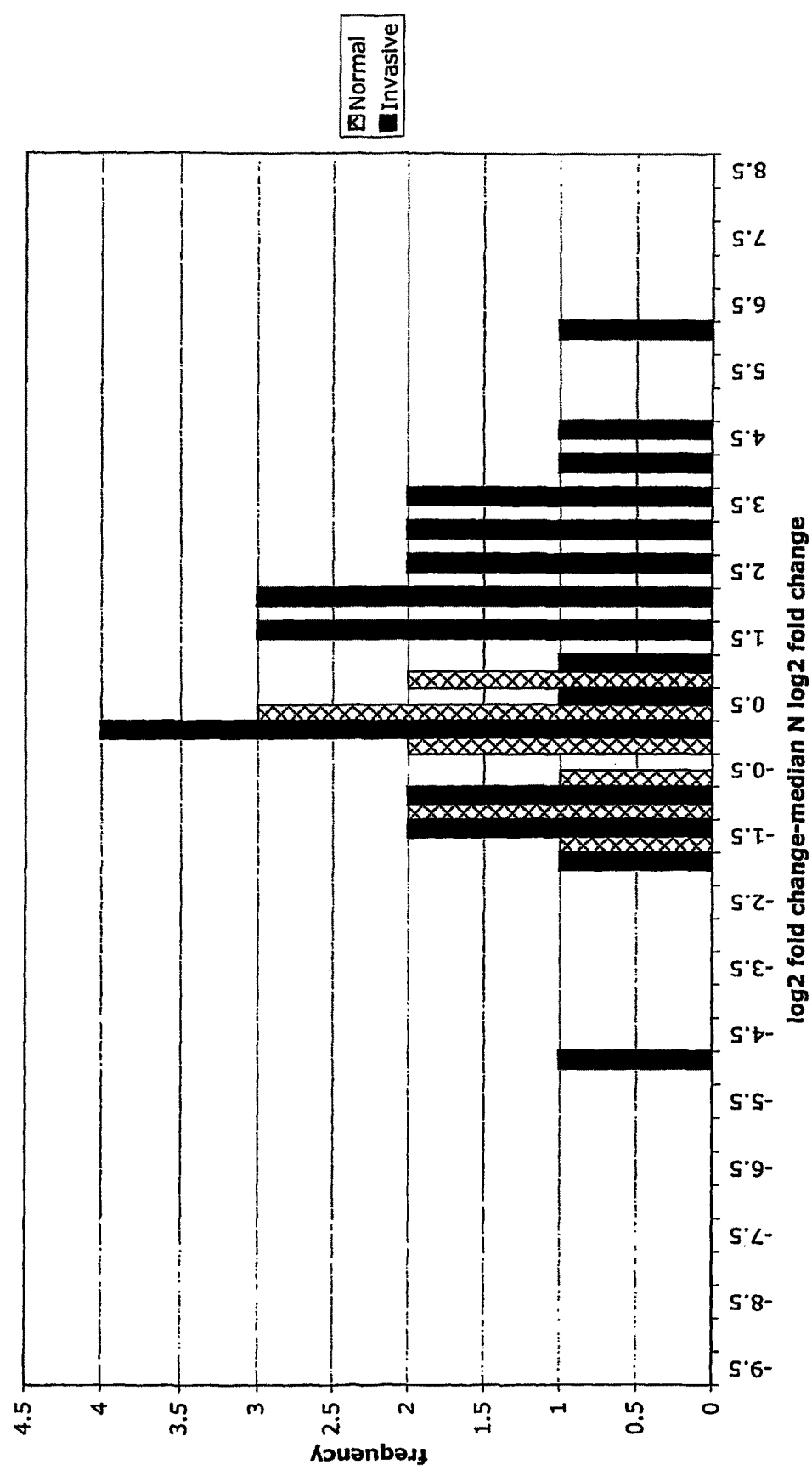
Figure 6A:
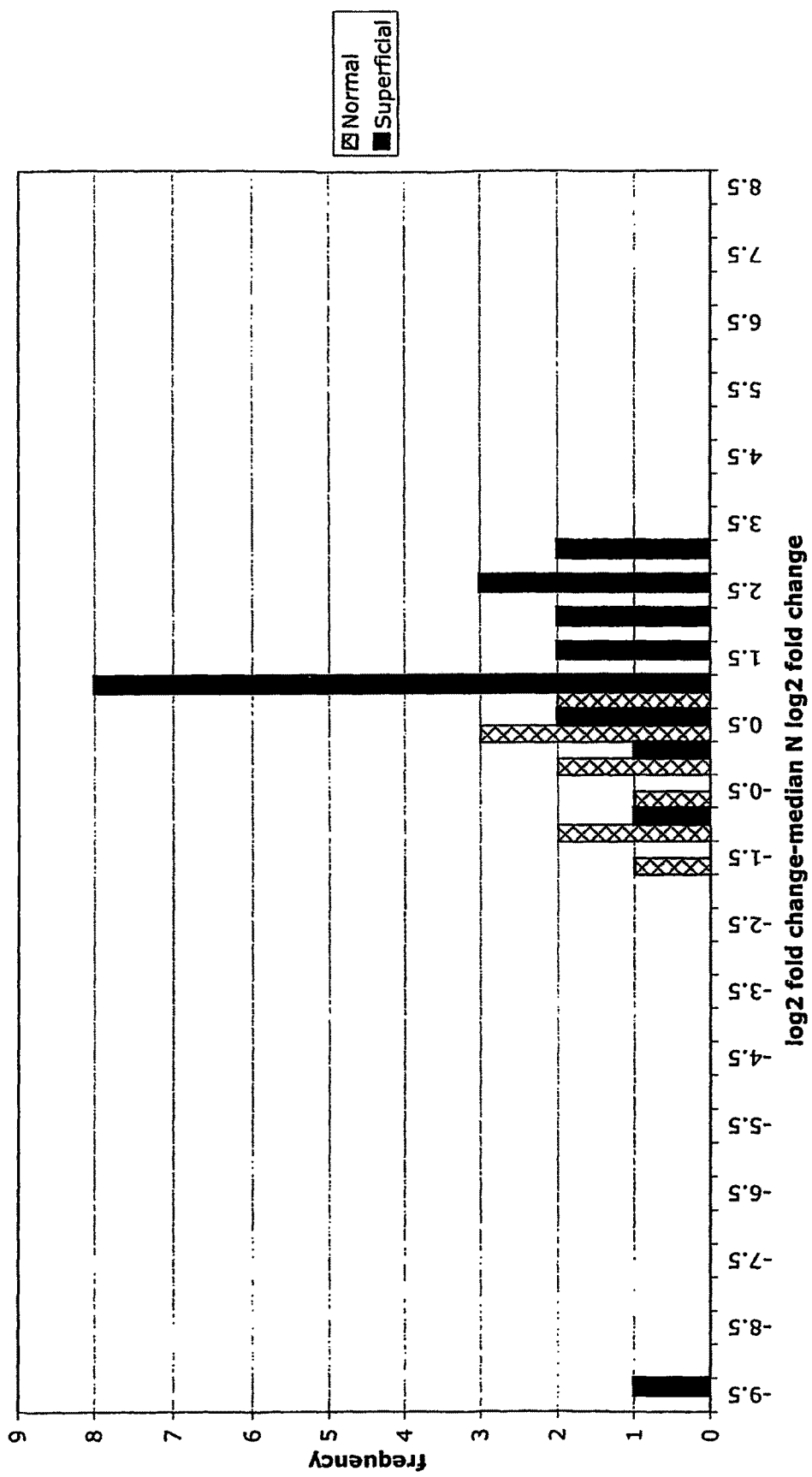
Figure 6A:
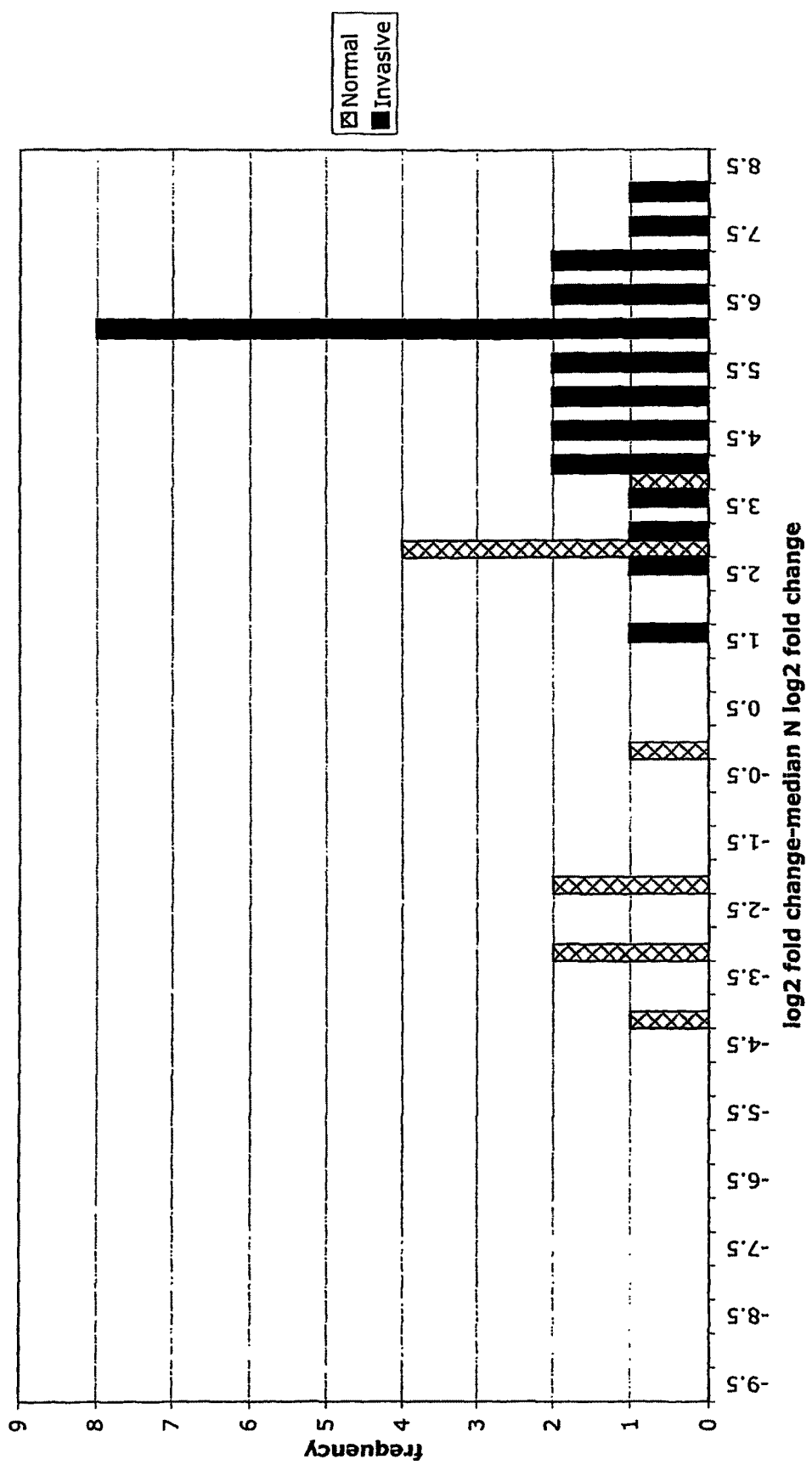
Figure 6:
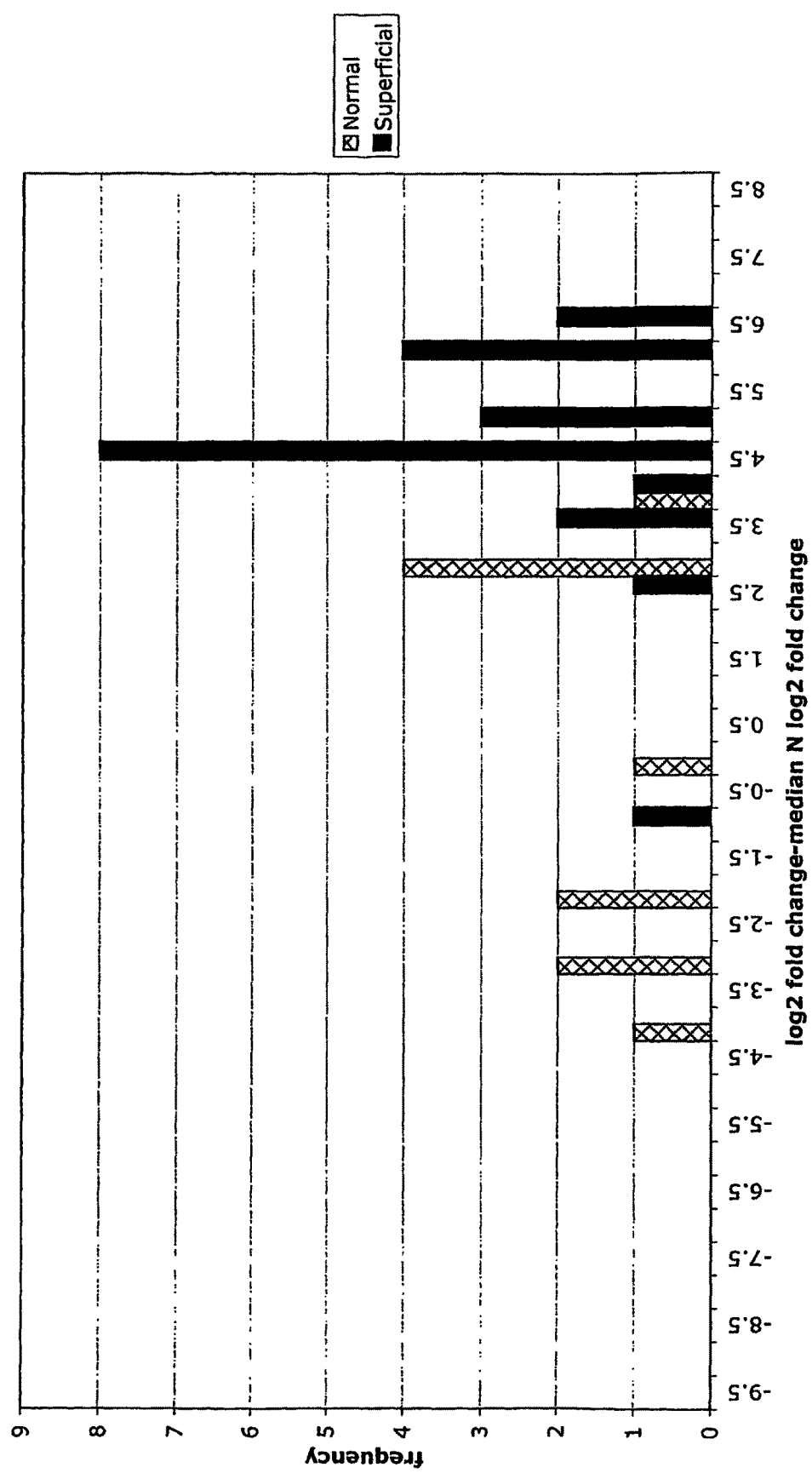
FIG. 6h: ENG, superficial.
FIG. 6i: IGFBP5, superficial.
FIG. 6k: NRP1, invasive.
FIG. 6l: NRP1, superficial.
FIG. 6o: EGFL6, superficial.
FIG. 6x: UBE2C, superficial.
Figure 6A:
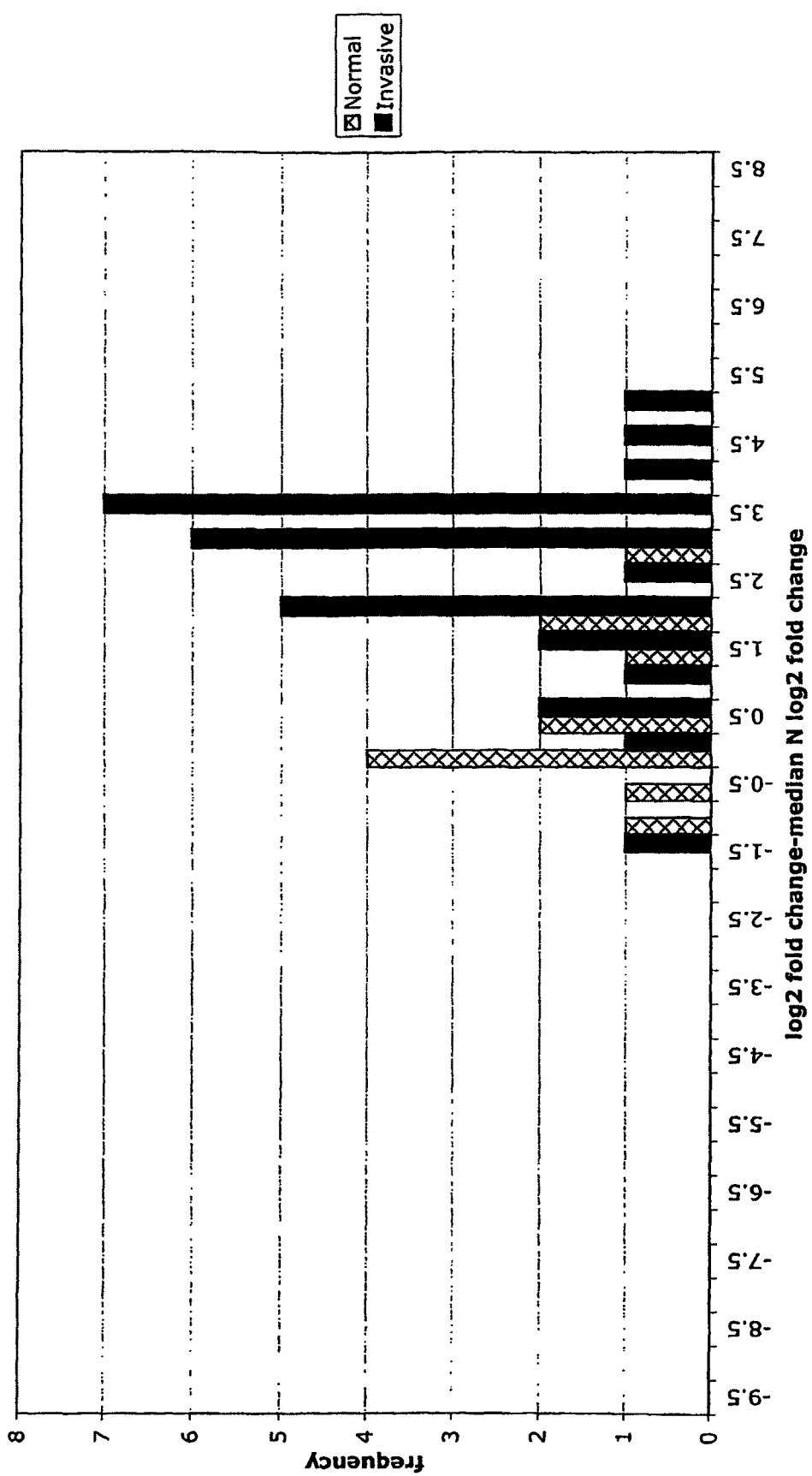
Figure 6A:
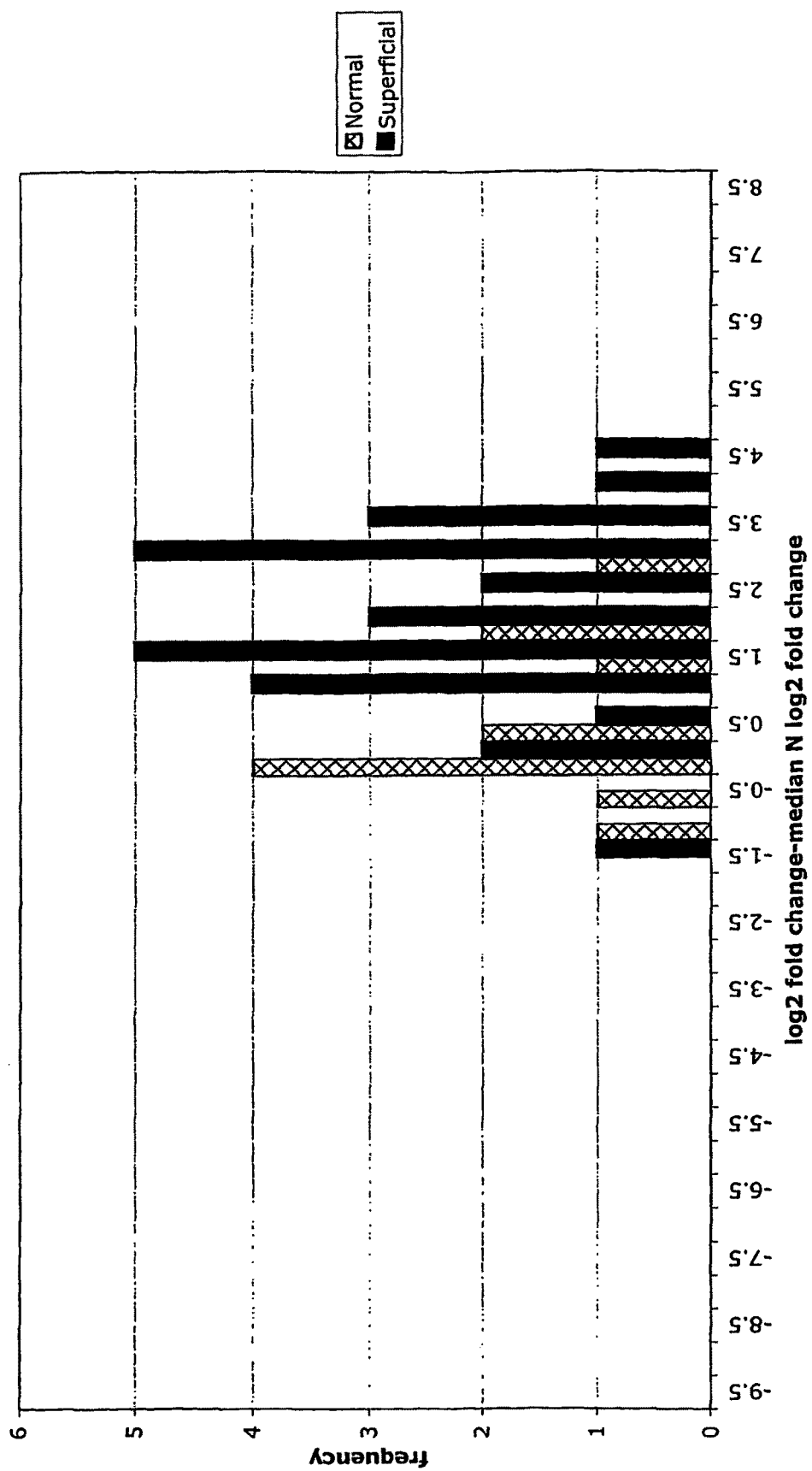

FIGS. 6a-6af depict histograms comparing frequency of observation of expression of each of a series of 18 genes (vertical axis) and the log2 fold change in expression for that gene (horizontal axis), for both normal tissue (open bars) and either superficial or invasive tumor tissues (black bars). We found surprisingly that for each of these 18 genes, there was substantial separation in the frequency distributions between normal and tumor tissue. For example, FIG. 6c depicts the results for TOP2a expression in invasive tumors. Only two tumor samples were observed to have an expression level in the normal range.

The accumulation of 18 BTMs-SPAG5, TOP2A, CDC2, ENG, IGFBP5, NOV, NRP1, SEMA3F, EGFL6, MGP, SEM2, CHGA, UBE2C, HOXA13, MDK, THY1, BIRC5 and SMC4L1, in the urine of patients and controls (FIG. 1: sample series 1) was determined using qPCR on total RNA extracted from equal volumes of urine. 17 of the BTMs showed greater accumulation in the urine of patients compared to the control urine samples, with EGFL6 being the exception (FIG. 7). The median fold difference for the 17 BTM ranged from 2 fold to 265 fold. The maximum difference between a single patient sample and the median level in controls ranged from 26 fold to >10,000 fold.

Figure 8:
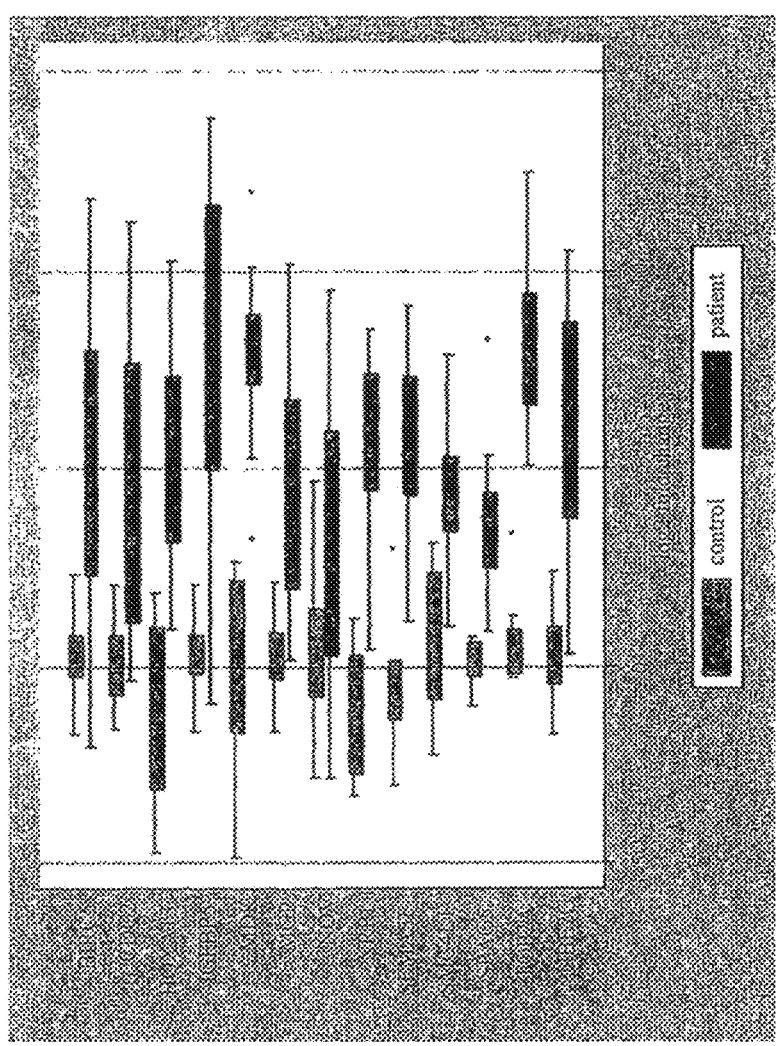
FIG. 8 depicts box and whisker plots showing the relative accumulation of bladder cancer markers in the urine of patients and healthy controls. Data are shown in pairs for each of twelve BTMs; the upper box in each pair represents urine samples from healthy control patients and the lower box represents urine samples from patients with bladder cancer. The boxes define the 25th, 50th and $75^{th}$ percentiles. All data is log2 fold change relative to the median healthy control. Dots represent outliers.

FIG. 8 shows the differences in BTM transcript accumulation for 13 BTMs depicted as box and whisker plots, and standardized to the median expression in control samples. FIG. 8 shows that MDK, SEMA3F and TOP2A have no overlap in urine from cancer patients and controls. Additionally, high levels of accumulation of transcripts for IGFBP5, HOXA13, MGP, NRP1, SMC4L1, SPAG4 and UBE2C are nearly always associated with bladder cancer. For the remainder of the BTM depicted in FIG. 8, BIRC5, NOV and CDC2, their expression in urine of patients with bladder cancer is increased by at least about 3-fold compared to normal control samples.

Figure 9:
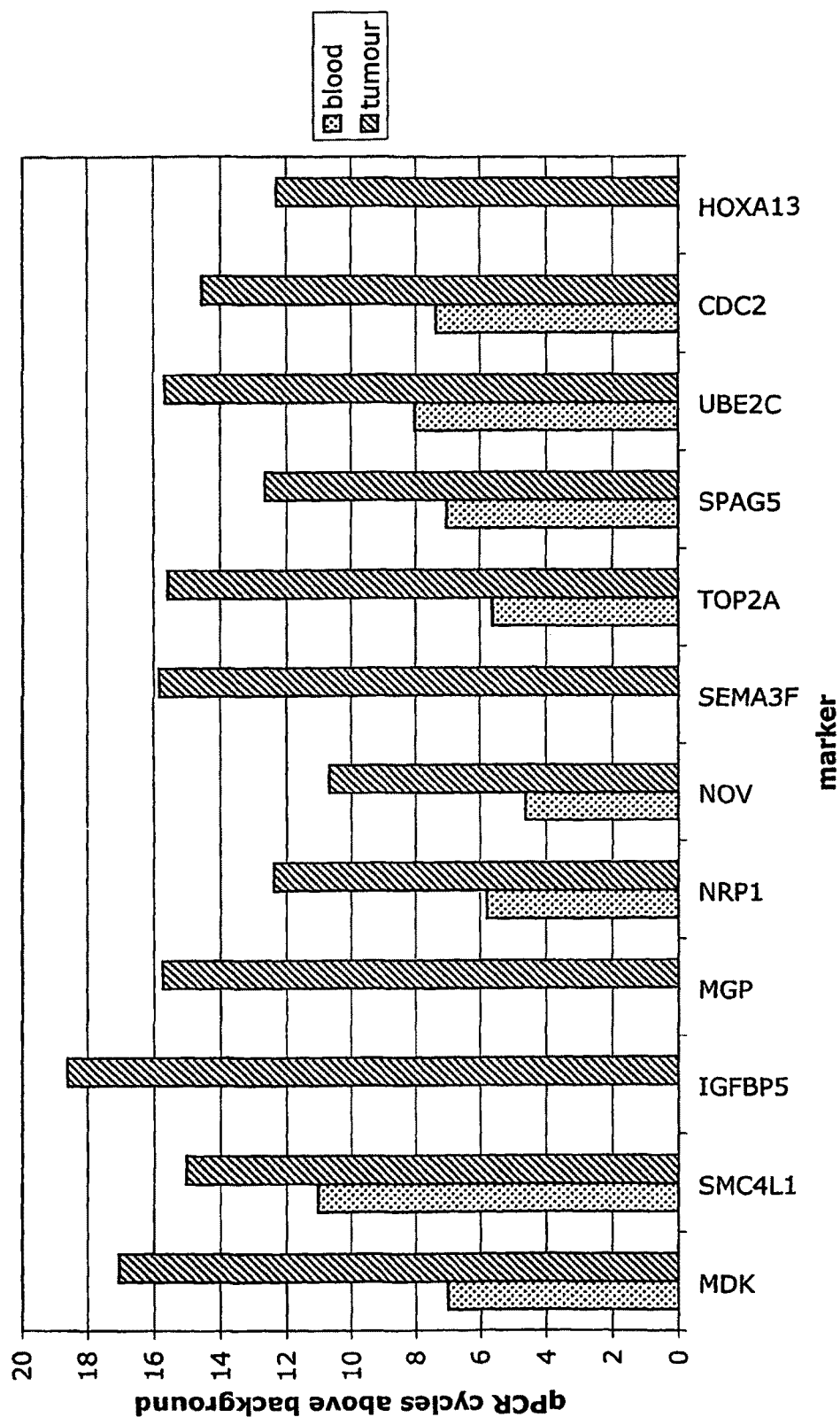
FIG. 9 depicts a bar graph of the quantitative PCR analysis of total RNA extracted from whole blood compared to RNA from bladder cancer tissue.

The principle clinical symptom that provokes testing for the presence of bladder cancer is hematuria (i.e. the presence of macroscopic or microscopic levels of blood in the urine). The blood is typically detected visually or by the chemical detection of haemoglobin using urine "dipsticks." Only approximately 15% and 4% of cases of macroscopic and microscopic hematuria, respectively, are associated with bladder cancer. Consequently, for a bladder cancer test to have high specificity, it is important that the levels of marker expression in whole blood are low or, in some cases, undetectable. Therefore, to enhance the identification of markers that have high specificity, the expression of twelve of the thirteen markers in FIG. 8 was determined in blood RNA using qPCR. QPCR was carried out on 5 ug total RNA extracted from blood and bladder tumor tissue using the primers and probes described in FIG. 2. FIG. 9 shows the number of cycles above background for each of the markers. For markers MGP, IGFBP5, SEMA3F and HoxA13, transcripts could not be detected in blood, but markers SMC4L1 and UBE2c, in particular, were expressed in blood. We note that the data, showing the number of PCR cycles, is inherently a log2-plot, whereby an increase in the number of cycles by 1 indicates a doubling of the signal. Thus, in evaluating the differences between marker presence in tumor tissue and blood, a difference of two (2) cycles, indicates a 4-fold difference in expression. Similarly, a difference of 5 cycles (e.g., for TOP2A) indicates a difference of expression of $2^5$, or 32 fold. Other markers such as TOP2A and MDK have detectable blood expression, but remain reasonable markers due to the large difference between the blood expression and the bladder tumor expression.

Figure 11:
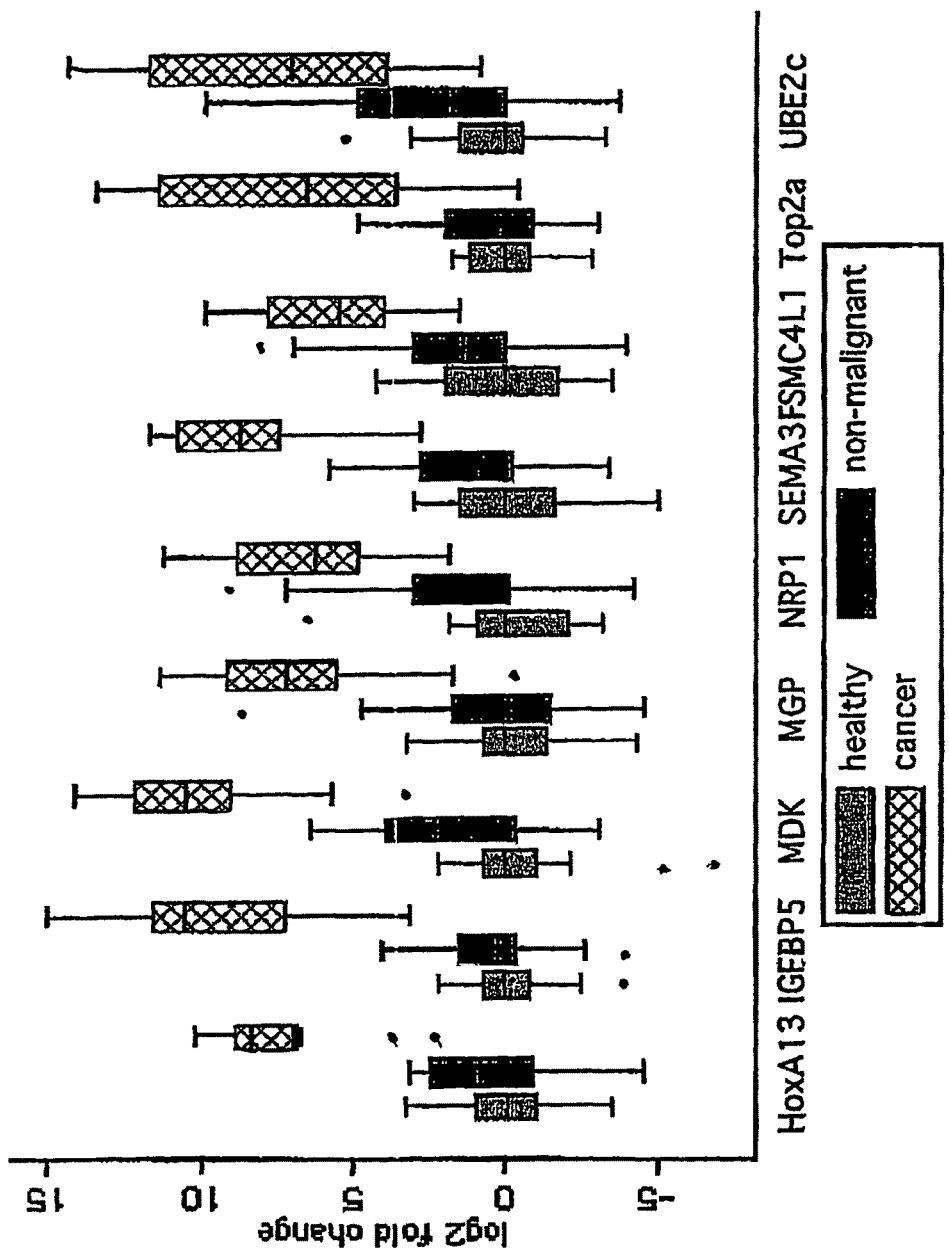
FIG. 11 depicts box and whisker plots showing the over-representation of marker transcripts in the urine of cancer patients compared to healthy and non-malignant controls. The boxes define the $25^{th}$, $50^{th}$ and $75^{th}$ percentiles. All data is relative to the median healthy control. The boxes with the spotted filling correspond to samples from healthy subjects. Boxes with shaded filling correspond to samples from patients with non-malignant urological disease, and boxes with the hashed filling correspond to samples from patients with bladder cancer, a. HOXA13; b. IGFBP5; c. MDK; d. MGP; e NRP1; f. SEMA3F; g. SMC4L1; h. TOP2A; i. UBE2C. Dots represent outliers.

To examine the differential between marker expression in whole blood and bladder tumors further, and to refine the selection of bladder cancer urine markers, nine markers were selected for further analysis using urine RNA from an additional 20 patients, 13 normal controls and 26 non-malignant controls (FIG. 1: sample series 2). The non-malignant controls included 20 samples with either occult blood or white blood cells detected in their urine by cytology. All nine markers showed differentiation between the controls and the cancer patient samples, with median log2 over-representation in the cancer patient samples ranging from 5.4 to 10.4 and 4.0 to 10.1 compared to the healthy samples and the non-malignant samples, respectively (FIG. 10). Box and whisker plots illustrating this data are shown in FIG. 11.

As predicted by the blood qPCR data, markers UBE2C and SMC4L1 showed marked increases in accumulation in the urine of non-malignant controls compared to healthy controls. NRP1 was also significantly elevated in the urine samples from non-malignant samples compared to healthy control urine samples, and showed considerable overlap between the cancer patients' samples and the non-malignant patients' samples, TOP2A and MDK also showed increases, but, because of their very high expression in TCC cells maintained a strong difference between the RNA accumulation in the non-malignant patient urine samples and the cancer patient samples. In contrast, HOXA13, IGFBP5, SEMA3F and MGP only showed small increases in the non-malignant urine samples compared to the healthy control samples.

Overall, six markers (SEMA3F, HOXA13, MDK, IGFBP5, MGP and TOP2A) showed minimal overlap between the cancer patient samples and the non-malignant controls. The remaining three markers (NRP1, UBE2C, SMC4L1) showed significant elevation in a subset of the non-malignant controls and overlap with the cancer patient samples. The increased accumulation of RNA markers in the urine of non-malignant controls compared to the healthy controls is consistent with the expression of these markers in cells of haemopoietic or endothelial origin that are present in the urine of patients with non-malignant disease. Therefore, use of individual markers for diagnosing bladder cancer using urine samples demonstrates increased sensitivity and specificity compared to prior art methods which do not account for marker expression in blood. This result was completely unexpected based on the prior art.

The data illustrates the surprising finding that the utility of using urine markers for bladder cancer that show high sensitivity and specificity cannot be accurately predicted using microarray analysis of tumor gene expression data alone. It is necessary to take into account the expression of putative markers in cells of haemopoietic and/or endothelial origin. This can be achieved by: (i) qPCR analysis of blood RNA, (ii) expression database analysis (e.g., EST libraries of blood and vascular/endothelial cell RNA) and/or (iii) qPCR analysis of RNA extracted from unfractionated urine.

Sensitivity and Specificity

Based on the two series of samples analysed and disclosed herein, the sensitivity for the detection of bladder cancer exceeds 95%. The specificity in series 2, which included the samples from patients with non-malignant disease, also exceeds 95%.

Example 3

Use of Multiple Markers in Detection of Bladder Cancer

Figure 12A:
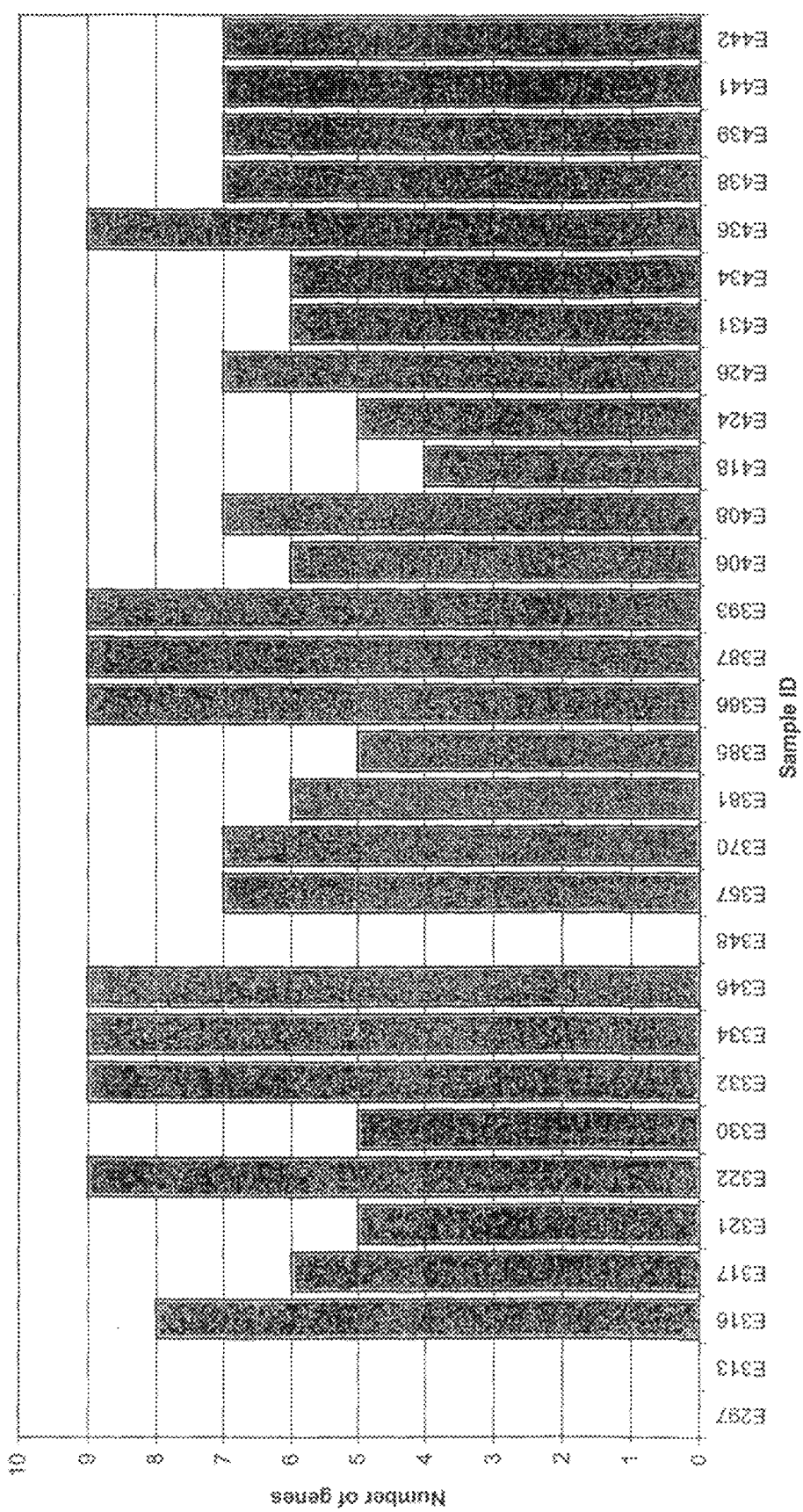
FIGS. 12a-12b depict histograms showing the number of markers with a higher expression than the $95^{th}$ percentile of the median normal expression for invasive and superficial type tumors, respectively. Results are based on qPCR data for 12 markers and are shown separately for each tumor sample.
Figure 12B:
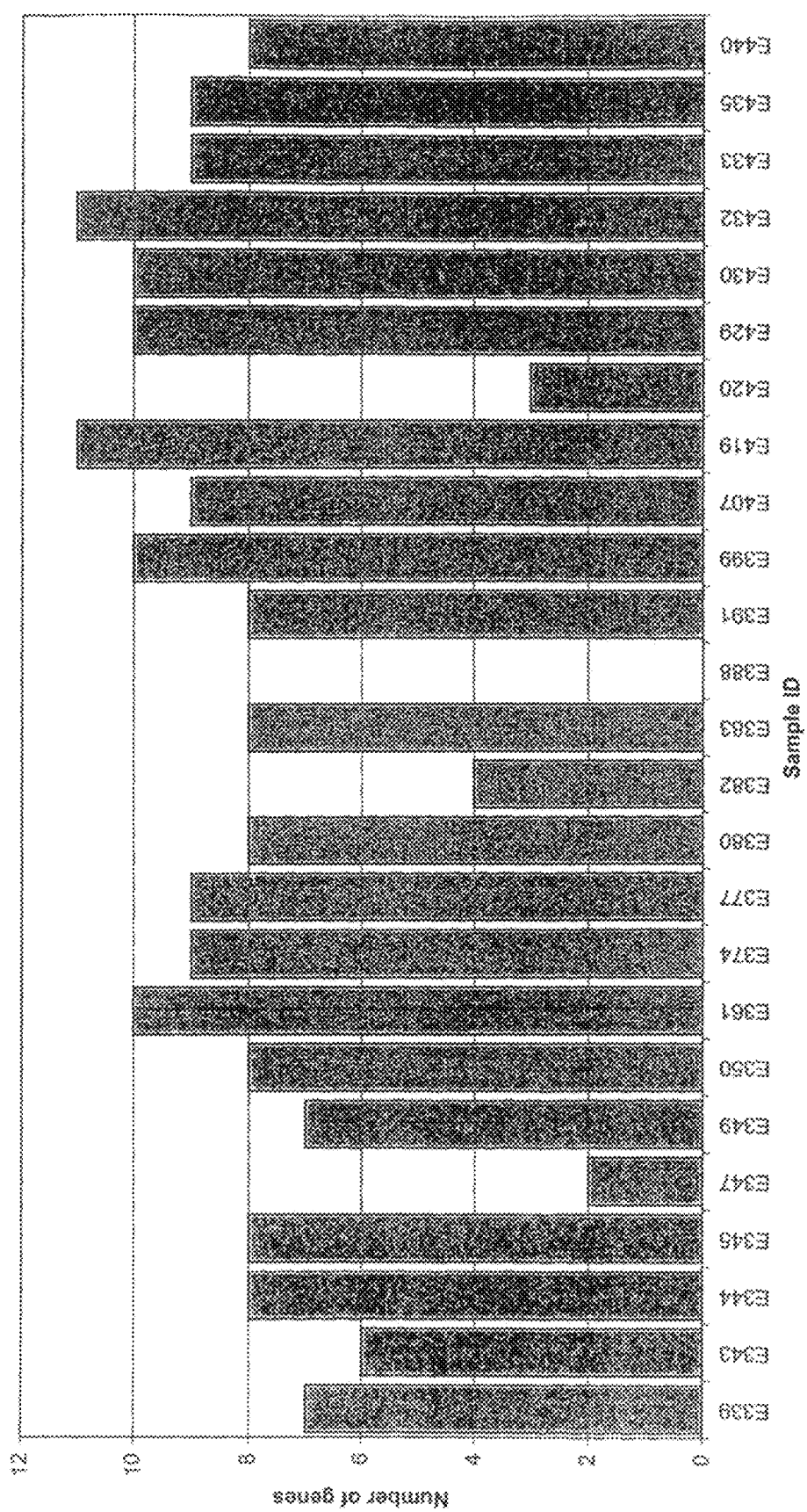

FIGS. 12a-12b depict histograms of the number of genes exhibiting a significantly increased expression ("over-expression") in individual tumor samples compared to normal samples. The histograms were based on qPCR data obtained from the first twelve markers shown in FIG. 5. Of the 30 invasive tumors in the PCR analysis, 27 (90%) over-expressed at least four genes greater than the $95^{th}$ percentile (FIG. 12a). Of the 25 superficial tumors in the analysis, 23 (92%) over-expressed at least four genes greater than the $95^{th}$ percentile (FIG. 12b). These findings indicates that, in situations in which multiple genes are over-expressed relative to normal tissue, the reliability of cancer detection can be very high, making diagnosis of cancer more certain. However, in some cases, elevation of expression of a single marker gene is sufficient to lead to the diagnosis of cancer.

The reliability of successful discrimination of tumor and non-tumor samples using marker combinations is further illustrated by a statistical analysis depicted in FIG. 13. This analysis compared the normal distributions of qPCR gene expression data from tumor and non-malignant samples. The qPCR data has been summarized in FIG. 5. The analysis shows the effect of increasing the numbers of markers used to discriminate between tumor and non-malignant samples on test sensitivity (with a fixed specificity of 95%). Although few of the 18 markers have a sensitivity of greater than 90, 95, or 99% when used alone in this analysis, the combination of two or three markers enabled high sensitivity to be reached with large numbers of combinations of two or three markers (FIGS. 14a and 14b).

FIGS. 14a and 14b show the sensitivity of specific markers and marker combinations for detecting invasive and superficial transitional cell carcinoma (TCC), when the specificity has been fixed at 95%. Only combinations with a sensitivity of >90% have been shown. Of the 15 markers shown in FIG. 14a, invasive bladder cancer can be detected with sensitivity of about 95% for TOP2A, SPAG5 and CDC2 singly. Other markers shown have lesser sensitivity when used singly.

However, combinations of two of the above markers dramatically improve sensitivity of detection of invasive bladder cancer (FIG. 13a and FIG. 14a). Sensitivity of greater than 95% can be found using 13 of the 105 combinations of two markers. In fact, using two markers results in a minimum sensitivity of 90% in 42 of 105 marker combinations.

For superficial bladder cancer (FIG. 13b and FIG. 14b), sensitivity of greater than 90% was not found with any markers singly, however, this threshold was reached with 11 of 136 two-marker combinations. Sensitivity of >95% was reached with 22 three-marker combinations.

The use of marker combinations also can dramatically improve the sensitivity of detection of bladder cancer using urine samples. FIGS. 15 and 16 shows the sensitivity of detection of individual markers and marker combinations using the urine qPCR data.

As seen in FIG. 16, although only IGFBP5 alone had a sensitivity of >95%, eight two-marker combinations and 37 three-marker combinations reached this threshold.

Example 4

Differential Transcript Accumulation in Patients with Superficial and Invasive Bladder Cancer It can be seen from FIG. 5 that several BTMs, including SEMA3F, HOXA13, TOP2A and SPAG5, show a differential expression between invasive bladder cancers and superficial bladder cancers. To extend this observation, the accumulation of these transcripts in urine from patients with invasive and superficial bladder cancer was compared.

RNA was extracted from equal volumes of urine derived from the patients described in FIG. 1 and the accumulation of BTMs determined by qPCR. The accumulation of specific BTM combinations were then expressed as ratios. BTM combinations consisted of one BTM with higher over-expression in invasive bladder tumors compared to superficial bladder tumors, and one BTM with higher over-expression in superficial tumors compared to invasive tumors.

Figure 17:
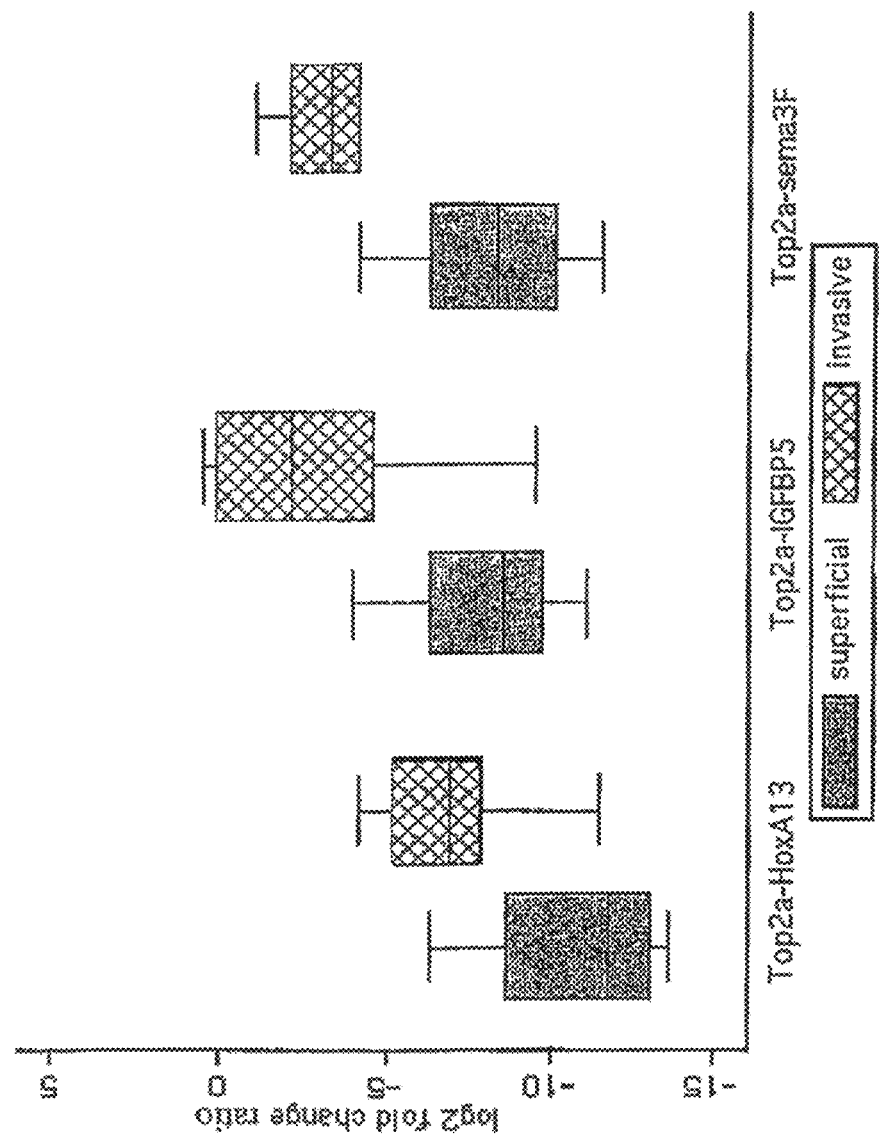
FIG. 17 depicts box and whisker plots showing the ratios of BTMs in RNA extracted from the urine of patients with both superficial and invasive bladder cancer. The boxes define the 25$^{th}$, 50$^{th}$ and 75$^{th}$ percentiles. The gray shaded boxes represent samples from patients with superficial bladder cancer, and the hatched boxes represent samples from patients with invasive bladder cancer, a. TOP2A/HOXA13 combination; b. TOP2A/IGFBP5 combination; and c. TOP2A/SEMA3F combination. Dots represent outliers.

FIG. 17 shows three marker combinations analysed on urine samples from 20 superficial and 14 invasive TCC patients. The three combinations shown are: (i) TOP2A and HOXA13, (ii) TOP2A and IGFBP5, and (iii) TOP2A and SEMA3F. It can be seen that these marker combinations are able to differentiate between the urine samples of patients with superficial and invasive TCC. Other markers in FIG. 5 that show a difference in expression between superficial and invasive types of TCC are also able to determine the type of TCC, based on a urine sample analysis.

Figure 18:
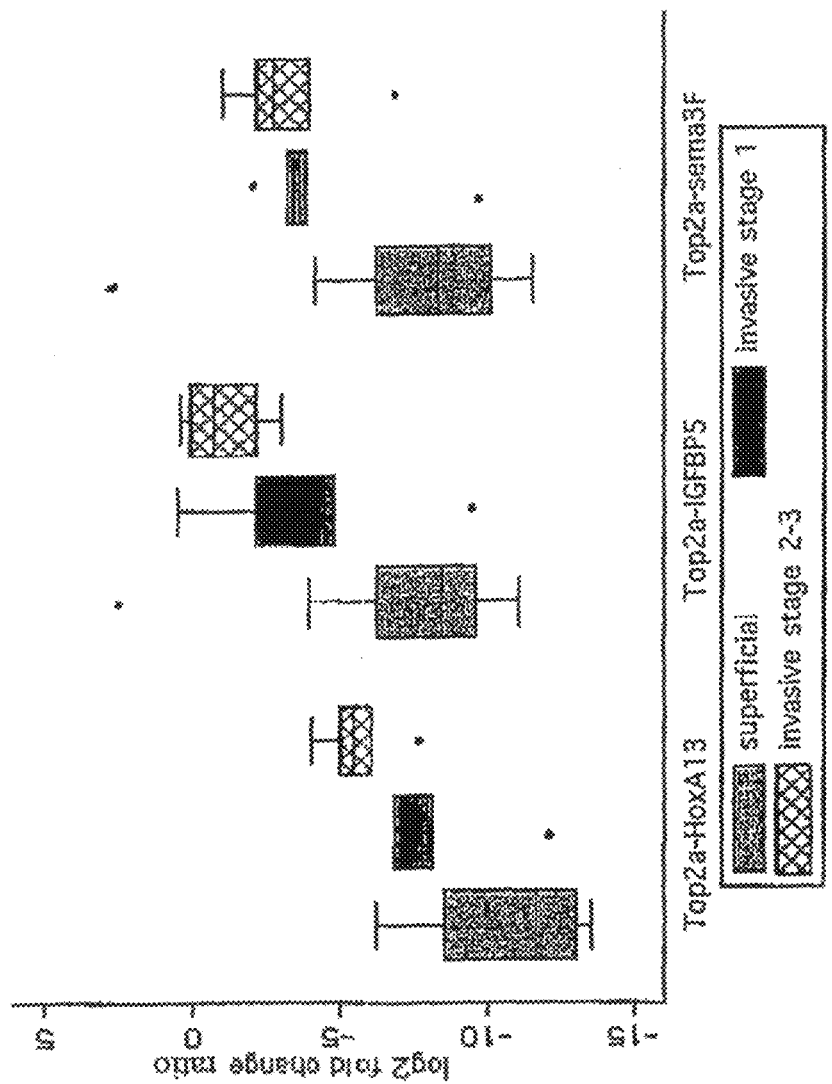
FIG. 18 depicts box and whisker plots showing the ratios of BTMs in the urine of patients with bladder cancer of different stages. The boxes define the 25$^{th}$, 50$^{th}$ and 75$^{th}$ percentiles. The boxes with the spotted filling correspond to samples from patients with superficial tumors, the grey shaded boxes correspond to samples from patients with stage 1 invasive tumors and the hatched boxes correspond to samples from patients with stage 2-3 tumors: a. TOP2A/HOXA13 combination; b. TOP2A/IGFBP5 combination; and c. TOP2A/SEMA3F combination. Dots represent outliers.

In addition, FIG. 18 shows that use of two-marker combinations including TOP2A can be used to distinguish invasive bladder cancer into stage 1-2 and stage 3 tumors.

Figure 19:
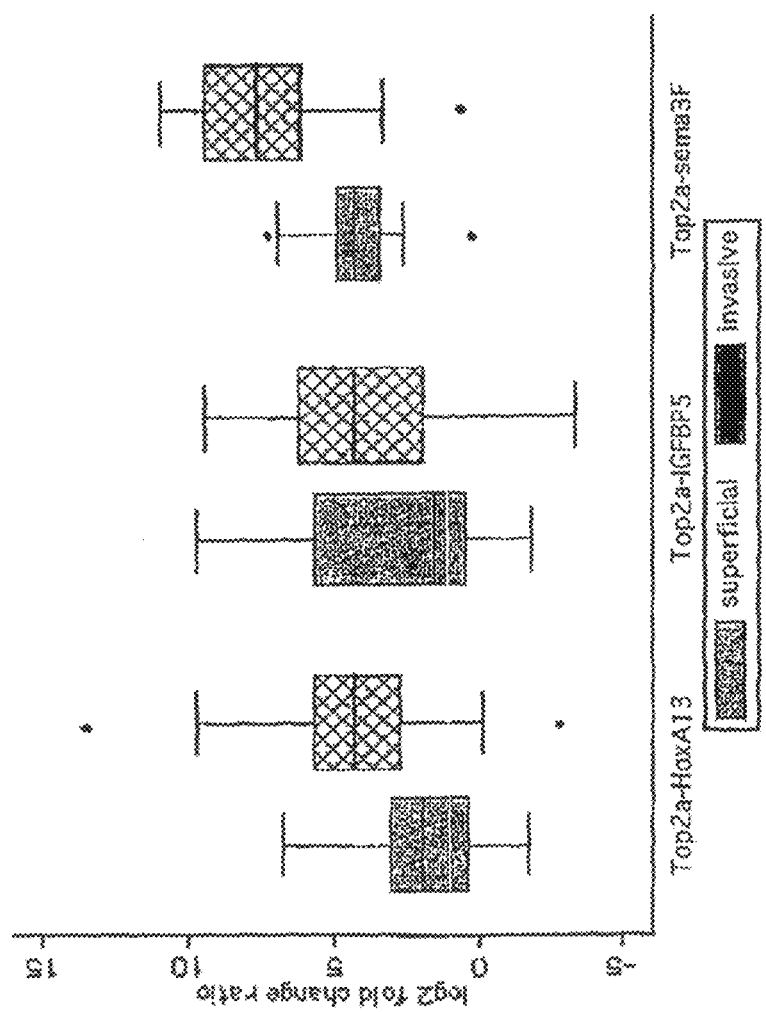
FIG. 19 depicts box and whisker plots showing the ratios of BTMs in RNA extracted from both superficial and invasive bladder tumors. The boxes define the 25$^{th}$, 50$^{th}$ and 75$^{th}$ percentiles. The gray shaded boxes represent superficial bladder tumor samples, and the hatched boxes represent invasive bladder tumor samples: a. TOP2A/HOXA13 combination, b. TOP2A/IGFBP5 combination, and c. TOP2A/SEMA3F combination. Dots represent outliers.

These observations show that determination of the accumulation of several BTM transcripts in the urine enables distinction between the invasive and superficial forms of bladder cancer. What is more, the BTM ratios determined by qPCR of urine samples from bladder cancer patients enable stronger differentiation between the invasive and superficial types than the same analysis carried out on tumor RNA. This is illustrated by FIG. 19, which shows box and whisker plots for: (i) TOP2A and HOXA13, (ii) TOP2A and IGFBP5, and (iii) TOP2A and SEMA3F using qPCR data from approximately 23 superficial and 28 invasive bladder tumor RNA preparations; although the ratios of these BTMs still permit distinction between the superficial and invasive types of bladder cancer, there is greater overlap between the superficial and invasive ratios. This finding may reflect contamination of tumor RNA preparations with cell types such as muscle and fibroblasts that do not have the same BTM ratio as the malignant cells. Alternatively, it may reflect a stronger differential in BTM expression in the malignant cells that are sloughed into the urine than those cells which remain in the body of the tumor. Regardless of the reason for the observation, we conclude that detecting accumulation of BTM in urine has substantial advantages over conventional microarray analysis of tissue samples.

Example 5

Antibodies to Bladder Tumor Markers

In additional aspects, this invention includes manufacture of antibodies against BTMs. Using methods described herein, novel BTMs can be identified using microarray and/or qPCR methods. Once a putative marker is identified, it can be produced in sufficient amount to be suitable for eliciting an immunological response. In some cases, a full-length BTM can be used, and in others, a peptide fragment of a BTM may be sufficient as an immunogen. The immunogen can be injected into a suitable host (e.g., mouse, rabbit, etc) and if desired, an adjuvant, such as Freund's complete adjuvant, Freund's incomplete adjuvant can be injected to increase the immune response. It can be appreciated that making antibodies is routine in the immunological arts and need not be described herein further. As a result, one can produce antibodies against BTMs or UBTMs identified using methods described herein.

In yet further embodiments, antibodies can be made against the protein or the protein core of the tumor markers identified herein or against an oligonucleotide sequence unique to a BTM. Although certain proteins can be glycosylated, variations in the pattern of glycosylation can, in certain circumstances, lead to mis-detection of forms of BTMs that lack usual glycosylation patterns. Thus, in certain aspects of this invention, BTM immunogens can include deglycosylated BTM or deglycosylated BTM fragments. Deglycosylation can be accomplished using one or more glycosidases known in the art. Alternatively, BTM cDNA can be expressed in glycosylation-deficient cell lines, such as prokaryotic cell lines, including *E. coli* and the like.

Vectors can be made having BTM-encoding oligonucleotides therein. Many such vectors can be based on standard vectors known in the art. Vectors can be used to transfect a variety of cell lines to produce BTM-producing cell lines, which can be used to produce desired quantities of BTM for development of specific antibodies or other reagents for detection of BTMs or for standardizing developed assays for BTMs or UBTMs.

Example 6

Kits

Based on the discoveries of this invention, several types of test kits can be envisioned and produced. First, kits can be made that have a detection device pre-loaded with a detection molecule (or "capture reagent"). In embodiments for detection of BTM mRNA, such devices can comprise a substrate (e.g., glass, silicon, quartz, metal, etc) on which oligonucleotides as capture reagents that hybridize with the mRNA to be detected is bound. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Regardless of the detection method employed, comparison of test BTM expression with a standard measure of expression is desirable. For example, RNA expression can be standardized to total cellular DNA, to expression of constitutively expressed RNAs (for example, ribosomal RNA) or to other relatively constant markers. In embodiments that measure BTMs in bodily fluids, such as urine, the standard can be an equal volume of urine obtained for subjects without malignant disease, as shown herein.

Antibodies can also be used in kits as capture reagents. In some embodiments, a substrate (e.g., a multiwell plate) can have a specific BTM or UBTM capture reagent attached thereto. In some embodiments, a kit can have a blocking reagent included. Blocking reagents can be used to reduce non-specific binding. For example, non-specific oligonucleotide binding can be reduced using excess DNA from any convenient source that does not contain BTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect BTM associated molecules can be used and be considered within the scope of this invention.

In embodiments relying upon antibody detection, BTM proteins or peptides can be expressed on a per cell basis, or on the basis of total cellular, tissue, or fluid protein, fluid volume, tissue mass (weight). Additionally, BTM in serum can be expressed on the basis of a relatively high-abundance serum protein such as albumin.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Example 7

Combinations of BTMs Used for Detection of Bladder Cancer I

Figure 20:
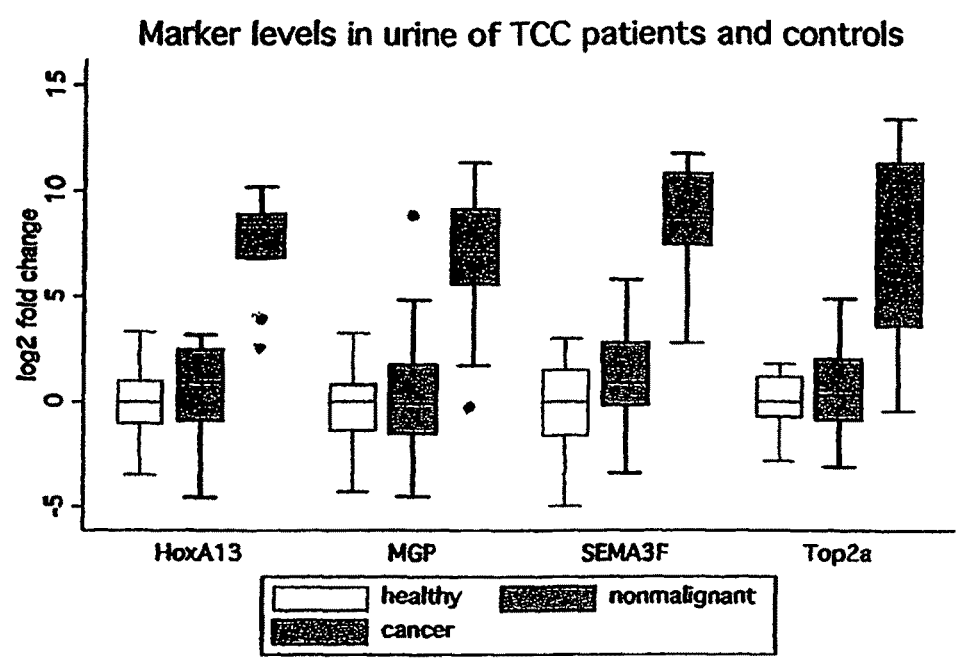
FIG. 20 depicts box and whisker plots showing one marker combination for application to bladder cancer detection. The plots show the over-representation of a group of four markers in the urine of cancer patients compared to healthy and non-malignant controls. The boxes define the 25$^{th}$, 50$^{th}$ and 75$^{th}$ percentiles. All data is relative to the median healthy control. The boxes with the spotted filling correspond to samples from healthy subjects. Boxes with gray shaded filling correspond to samples from patients with non-malignant urological disease, and boxes with the hashed filling correspond to samples from patients with bladder cancer a. HOXA13, b. MGP: c. SEMA3F, and d. TOP2A. Dots represent outliers.

In one series of embodiments, reagents for the testing the BTMs HOXA13, MGP, SEMA3F and TOP2A, alone or in combination, can be incorporated into a kit for the testing of unfractionated urine or urine cell sediments to detect bladder cancer. The range of accumulation of these BTMs in cancer patients and controls are shown in FIG. 20. The urine samples were collected from patients with diagnosed bladder cancer who required monitoring for disease progression or treatment response, individuals with urological symptoms including macroscopic or microscopic hematuria, or asymptomatic individuals. For patients or individuals being tested with a kit that measures the BTMs in unfractionated urine, approximately 2 mls of urine can be taken for testing. For tests on the urine pellet, >20 mls of urine can be collected.

A suitable kit includes: (i) instructions for use and result interpretation, (ii) reagents for the stabilization and purification of RNA from unfractionated urine or urine pellets, (iii) reagents for the synthesis of cDNA including dNTPs and reverse transcriptase, and (iv) reagents for the quantification of the BTM cDNA. In one form, these reagents would be used for quantitative PCR and would include specific exon-spanning oligonucleotide primers, a third oligonucleotide labeled with a probe for detection, Taq polymerase and the other buffers, salts and dNTPs required for PCR. The kit can also use other methods for detection of the transcripts such as direct hybridization of the BTM RNA with labeled probes or branched DNA technology; (v) oligonucleotides and probe for the detection of transcripts from a highly transcribed gene, such as β-actin, to serve as a quality control measure; and (vi) quantified samples of the BTM target sequence to act as an internal calibration standard and a reference for the upper limit of accumulation of the BTM transcript in healthy and non-malignant controls. The upper limit can be defined as the $95^{th}$ or $99^{th}$ percentile of the control range, although other limits could be applied. In particular, for diagnosing superficial bladder cancer, a convenient threshold is above about 50%, in other cases above about 60%, 70% or 80%.

Thus, using methods of this invention, one can detect bladder cancer, as well as the stage and type with increased sensitivity and specificity compared to prior art methods.

In some embodiments, renal function can be determined using conventional methods (e.g., creatinine measurements). In some of these embodiments, marker accumulation can be corrected for by a measure of renal function (e.g., urine volume, cell volume, cell number, or total cellular protein in the urine sample).

For tests involving qPCR, test samples that exceeded the pre-determined upper limit would be scored as positive if the accumulation of BTM in the test sample was more than one PCR cycle higher than the upper limit. For other detection methods, results greater than 2 fold higher than the upper-limit (e.g., $90^{th}$, $95^{th}$ or $97.5^{th}$ percentile) of normal would be scored as positive.

Example 8

Combinations of BTMs Used for Detection of Bladder Cancer II

In another series of embodiments, the accumulation in urine of either or both of the marker combinations TOP2A/SEMA3F and TOP2A/HOXA13 can be used to provide a strong prediction of the histological type of bladder cancer that is present in a patient with a diagnosis of bladder cancer made using a urine or blood test of any type. Thus, cystoscopy and histological examination may not be needed to diagnose the type of bladder cancer.

Figure 21:
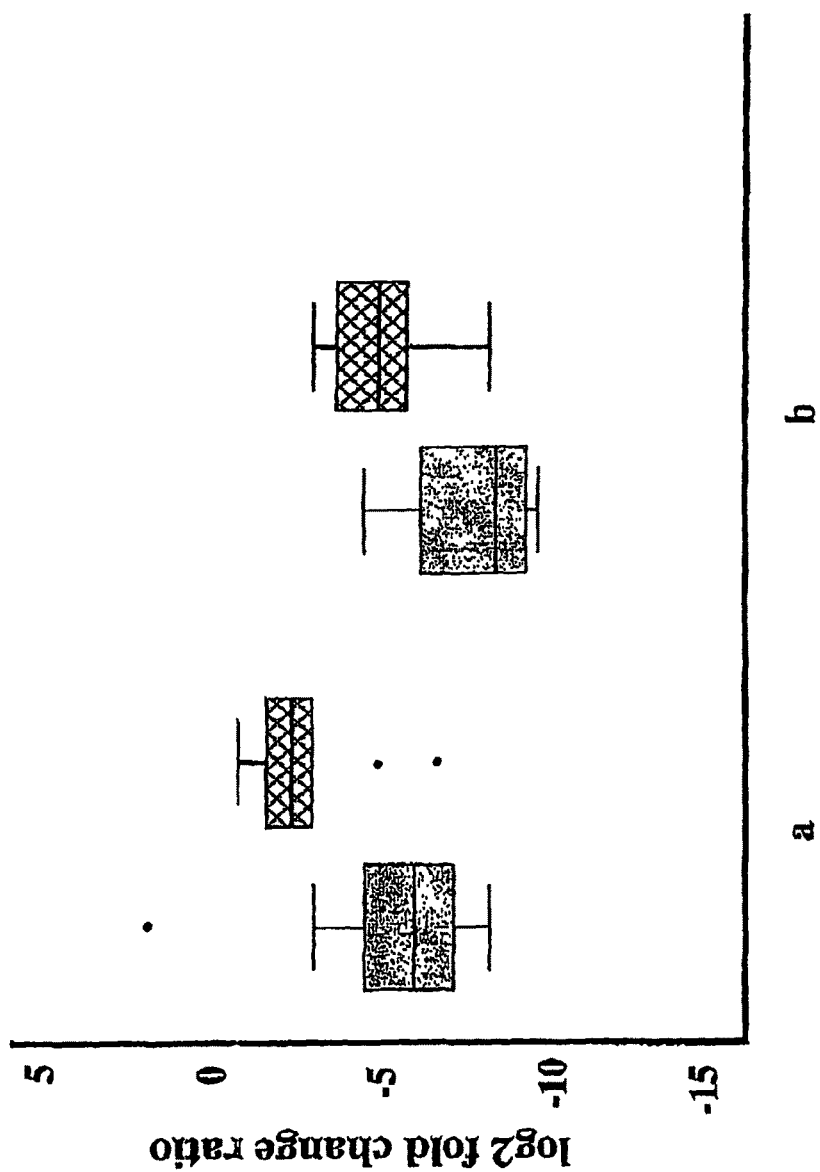
FIG. 21 depicts box and whisker plots showing marker combinations for determining the histological type of bladder cancer. The plots show the ratios of BTMs in RNA extracted from the urine of patients with both superficial and invasive bladder cancer. The boxes define the 25$^{th}$, 50$^{th}$ and 75$^{th}$ percentiles. The gray shaded boxes represent samples from patients with superficial bladder cancer, and the hatched boxes represent samples from patients with invasive bladder cancer: a. TOP2A/SEMA3F combination, b. TOP2A/HOXA13 combination. Dots represent outliers.

Kits used for testing these ratios contain (i) to (iv) of the components described in Example 7. Following quantification of the accumulation of the BTMs according to standard qPCR practice, the ratios of TOP2A/SEMA3F and TOP2A/HOXA13 were calculated. The ranges of these ratios in the urine of patients with superficial and invasive bladder cancer are shown in FIG. 21. Using a qPCR test, a difference less than five cycles between TOP2A and SEMA3F, with SEMA3F being the most abundant transcript, can predict invasive bladder cancer, and greater than five cycles can predict superficial bladder cancer. For TOP2A and HOXA13, a difference less than eight cycles, with HOXA13 being the most abundant transcript, can predict invasive bladder cancer, and greater than eight cycles can predict superficial bladder cancer.

Example 9

Evaluation of Progression of Bladder Cancer Using BTMs

To evaluate the progression of bladder tumors, samples of tissue are obtained by biopsy of bladder wall or samples of urine are collected over time from a patient having bladder cancer. Evaluation of accumulation of BTMs, UBTMs or combinations thereof are made for samples taken at different times. Increased accumulation of individual or combinations of BTMs or UBTMs are indicative of progression of bladder cancer.

Example 10

Evaluation of Therapy of Bladder Cancer Using BTMs

To evaluate the efficacy of therapy for bladder tumors, samples of tissue and/or urine are obtained before treatment is initiated. The baseline levels of one or more BTMs or UBTMs are determined, as are ratios of various BTMs and UBTMs with respect to each other. Treatment is initiated, and can include any therapy known in the art, including surgery, radiation therapy or chemotherapy as appropriate to the type and stage of the disease. During the course of therapy, samples of tissue and/or urine are collected and analyzed for the presence and amount of BTMs and/or UBTMs. Ratios of various BTMs and UBTMs are determined and results are compared to: (1) the patient's baseline levels before treatment or (2) normal values obtained from a population of individuals not having bladder cancer.

INCORPORATION BY REFERENCE

All of the publications and patents cited in this application are incorporated fully herein by reference. This application contains nucleotide and/or protein sequences. A Sequence Listing in computer-readable format and a diskette containing a Sequence Listing are included with this application and are incorporated herein fully by reference.

INDUSTRIAL APPLICABILITY

Methods for detecting BTM and UBTM family members include detection of nucleic acids, proteins and peptides using microarray and/or real time PCR methods. The compositions and methods of this invention are useful in diagnosis of disease, evaluating efficacy of therapy, and for producing reagents and test kits suitable for measuring expression of BTM family members or UBTM family members.

We claim:

1. A polymerase chain reaction (PCR) based kit for detecting bladder cancer, consisting of a forward primer, a reverse primer, and a labeled probe for each of the markers, sperm associated antigen 5 (SPAG5), topoisomerase (DNA) II alpha 170 kDa (TOP2A), cell division cycle 2, G1 to S and G2 to M (CDC2), endoglin (Osler-Rendu-Weber syndrome 1) (ENG), insulin-like growth factor binding protein 5 (IGFBP5), nephroblastoma overexpressed gene (NOV), neuropilin 1 (NRP1), sema domain, immunoglobulin domain (Ig), short basic domain, secreted, (semaphorin) 3F (SEMA3F), EGF-like-domain, multiple 6 (EGFL6), matrix Gla protein (MGP), semaphorin (SEM2), chromogranin A (parathyroid secretory protein 1) (CHGA), Thy-1 cell surface antigen (THY1), ubiquitin-conjugating enzyme E2C (USE2G), homeo box A13 (HOXA13), midkine (neurite growth-promoting factor 2) (MDK), baculoviral IAP repeat-containing 5 (survivin) (BIRC5), and SMC4 structural maintenance of chromosomes 4-like 1 (yeast) (SMC4L1); and
solutions for mixing reagents; and
reaction chambers for carrying out PCR amplification of each marker.

2. The polymerase chain reaction (PCR) based kit of claim 1, wherein:
(a) at least two of the following combinations of oligonucleotides (i-xiii) are selected from the group consisting of:
(i) SEQ ID NO.1, SEQ ID NO.14, and SEQ ID NO.27;
(ii) SEQ ID NO.2, SEQ ID NO.15, and SEQ ID NO.28;
(iii) SEQ ID NO.3, SEQ ID NO.16, and SEQ ID NO.29;
(iv) SEQ ID NO.4, SEQ ID NO.17, and SEQ ID NO.30;
(v) SEQ ID NO.5, SEQ ID NO.18, and SEQ ID NO.31;
(vi) SEQ ID NO.6, SEQ ID NO.19, and SEQ ID NO.32;
(vii) SEQ ID NO.7, SEQ ID NO.20, and SEQ ID NO.33;
(viii) SEQ ID NO.8, SEQ ID NO.21, and SEQ ID NO.34;
(ix) SEQ ID NO.9, SEQ ID NO.22, and SEQ ID NO.35;
(x) SEQ ID NO.10, SEQ ID NO.23, and SEQ ID NO.36;
(xi) SEQ ID NO.11, SEQ ID NO.24, and SEQ ID NO.37;
(xii) SEQ ID NO.12, SEQ ID NO.25, and SEQ ID NO.38;
(xiii) SEQ ID NO.13, SEQ ID NO.26, and SEQ ID NO.39; and
(b) reaction reagents and reaction chambers for carrying out PCR amplification each of said combinations of oligonucleotides.

3. A polymerase chain reaction (PCR) based kit for detecting bladder cancer, consisting of combinations of oligonucleotides being a forward primer, a reverse primer, and a labeled probe for each of the markers, said markers consisting of:
a) cell division cycle 2, G1 to S and G2 to M (CDC2), insulin-like growth factor binding protein 5 (IGFBP5), homeo box A13 (HOXA13), and midkine (neurite growth-promoting factor 2) (MDK); and
b) reaction reagents and reaction chambers for carrying out PCR amplification each of said combinations of oligonucleotides.

4. The kit of claim 3, said oligonucleotides selected from the group consisting of:
(i) SEQ ID NO.3 SEQ ID NO.16, and SEQ ID NO.29; and
(ii) SEQ ID NO.5, SEQ ID NO.18, and SEQ ID NO.31.

5. A polymerase chain reaction (PCR) based kit for detecting bladder cancer, consisting of combinations of oligonucleotides being a forward primer, a reverse primer, and a labeled probe for each of the markers, said markers consisting of
a) homeo box A13 (HOXA13), and midkine (neurite growth-promoting factor 2) (MDK); and
b) reaction reagents and reaction chambers for carrying out PCR amplification each of said combinations of oligonucleotides.

* * * * *